United States Patent
Brown et al.

(10) Patent No.: US 11,193,840 B1
(45) Date of Patent: Dec. 7, 2021

(54) WEARABLE USER INPUT DEVICE AND SENSOR SYSTEM FOR SPORTS TRAINING

(71) Applicant: Invent.ly, LLC, Malibu, CA (US)

(72) Inventors: Stephen J. Brown, Malibu, CA (US); Hector H. Gonzalez-Banos, Mountain View, CA (US)

(73) Assignee: Invent.ly, LLC, Malibu, CA (US)

( * ) Notice: Subject to any disclaimer, the term of this patent is extended or adjusted under 35 U.S.C. 154(b) by 0 days.

(21) Appl. No.: 16/950,341

(22) Filed: Nov. 17, 2020

Related U.S. Application Data

(63) Continuation of application No. 16/710,251, filed on Dec. 11, 2019, now Pat. No. 10,876,912, which is a continuation of application No. 14/547,293, filed on Nov. 19, 2014, now Pat. No. 10,520,378, which is a continuation-in-part of application No. 14/501,841, filed on Sep. 30, 2014, now abandoned, and a continuation-in-part of application No. 14/489,648, filed on Sep. 18, 2014, now abandoned, and a continuation-in-part of application No. 14/335,914, filed on Jul. 20, 2014, now abandoned, which is a continuation-in-part of application No. 14/220,378, filed on Mar. 20, 2014, now abandoned.

(51) Int. Cl.
*G01L 1/00* (2006.01)
*G01L 5/00* (2006.01)
*A61B 5/00* (2006.01)

(52) U.S. Cl.
CPC .......... *G01L 5/0052* (2013.01); *A61B 5/6801* (2013.01)

(58) Field of Classification Search
CPC ............................ G01L 5/0052; A61B 5/6801
USPC ........................................................ 702/41
See application file for complete search history.

(56) References Cited

U.S. PATENT DOCUMENTS 6,826,509 B2 * 11/2004 Crisco, III ........... A61B 5/6814
702/141

* cited by examiner

*Primary Examiner* — Caleb E Henry
(74) *Attorney, Agent, or Firm* — Christopher P. Maiorana, PC

(57) ABSTRACT

A system for monitoring injuries comprising a plurality of wearable user input devices and a wireless transceiver. Each of the plurality of wearable user input devices may be configured to detect motion patterns of a user. Each of the plurality of wearable user input devices may be configured as performance equipment. The wireless transceiver may be configured to communicate the motion patterns to a user device. The user device may be configured to (i) develop and store reference patterns related to impacts, (ii) compare the detected motion patterns with the reference patterns, (iii) estimate a location and direction of an impact based on the comparison, (iv) accumulate data from the estimated impact with previously suffered impact data, (v) aggregate results based on the accumulated impact data and context information and (vi) generate feedback for the user based on the aggregated results.

16 Claims, 26 Drawing Sheets

WEARABLE USER INPUT DEVICE AND SENSOR SYSTEM FOR SPORTS TRAINING

This application relates to U.S. Ser. No. 16/710,251, filed Dec. 11, 2019, which relates to U.S. Ser. No. 14/547,293, filed Nov. 19, 2014, which relates to U.S. Ser. No. 14/501,841, filed Sep. 30, 2014. U.S. Ser. No. 14/547,293 also relates to U.S. Ser. No. 14/489,648, filed Sep. 18, 2014. U.S. Ser. No. 14/547,293 also relates to U.S. Ser. No. 14/335,914, filed Jul. 20, 2014, which relates to U.S. Ser. No. 14/220,378, filed Mar. 20, 2014. U.S. Ser. No. 14/220,378 relates to co-pending U.S. Ser. No. 14/100,226, filed Dec. 9, 2013. Each of the mentioned applications are hereby incorporated by reference in their entirety.

FIELD OF THE INVENTION

The present invention relates to sensor systems generally and, more particularly, to a wearable user input device and sensor system to detect injury.

BACKGROUND OF THE INVENTION

There are many situations where user input into a computing system is useful to gather large amounts of information about a user. Accurate information about users is useful for training and safety in many industries. Gathering information should be discreet, unobtrusive, and should not negatively impact performance. In some contexts, similar information patterns might need a different interpretation. In other situations, the user may be limited in ability to input information into a computing system or to use and control an electronic device. It would be a further advantage if such input systems could be ubiquitous so that they become second nature and automatic as the brain of the user adapts to the input and control mechanisms.

A brain computer interface would be the ideal, but would require inconvenient or cumbersome wearable devices and is not precise enough. Biometric identification is used for many applications including unlocking mobile phones as well as access to digital and physical spaces. However, biometric identification is limited in what it can do. For example, biometric identification can only identify the user, not the intentions of the user or help the user to achieve a goal other than entry.

"Smart textiles" have been developed that are laden with sensors to capture data automatically from the user continuously and without the user thinking about it. However, smart textiles have the limitations of needing to be changed and washed, to be powered or laden with electronics or sensors, and to match the fashion sense of the user.

Wearable devices have been described including wrist-worn and finger-worn devices and have been successful in capturing user activity and other sensor data. However, wearable devices have not succeeded as input devices because they also do not adapt to the intentions and goals of the user in order to seamlessly accomplish a range of desired tasks as a training device. Conventional gesture detection systems are either a tactile input (like touch screens), detected with cameras, or are detected through a combination of beam and motion detection on a larger device.

When performing a physical activity such as sports and other types of performances it is not practical for a user to input data into a computing system. Physical activity involves accurate movement, lots of training, and often has restrictions on the type of clothing/equipment that can be worn. A user performing a physical activity cannot stop to input user data and cannot be encumbered by obtrusive input systems. Subtle differences in motion are sometimes the difference between a successful execution of an action and an unsuccessful execution of an action.

Concussions and other head injuries are a big issue in sports, especially for children. Head injuries are also an issue for members of the military. One of the most common injuries faced by military veterans is traumatic brain injury from LEDs. The importance of monitoring head injuries has gained awareness due to high profile incidents. Sports organizations are increasingly focusing on ensuring player safety when potential head injuries are suspected.

Many players want to stay in the game, even when injured. Coaches, fans, and team owners do not want star players sitting on the bench. Players sometimes seem healthy but symptoms of injury are not noticeable until later. Players that have sustained a head injury are at a higher risk of sustaining an even more severe injury. However, head injuries are highly individualized events and richer data sets are needed to determine whether a player has sustained an injury and/or is at risk of sustaining further injury.

In amateur sports there is an increasing need for solutions that indicate to coaches and physical therapists when an athlete has suffered a risky head blow. Often the athlete appears unaffected by a head collision, continues to play, only to collapse later suffering further injury.

It would be desirable to implement a wearable user input device and sensor system capable of detecting injury.

SUMMARY OF THE INVENTION

The present invention concerns a system for monitoring injuries comprising a plurality of wearable user input devices and a wireless transceiver. Each of the plurality of wearable user input devices may be configured to detect motion patterns of a user. Each of the plurality of wearable user input devices may be configured as performance equipment. The wireless transceiver may be configured to communicate the motion patterns to a user device. The user device may be configured to (i) develop and store reference patterns related to impacts, (ii) compare the detected motion patterns with the reference patterns, (iii) estimate a location and direction of an impact based on the comparison, (iv) accumulate data from the estimated impact with previously suffered impact data, (v) aggregate results based on the accumulated impact data and context information and (vi) generate feedback for the user based on the aggregated results.

The objects, features and advantages of the present invention include providing a wearable user input device and sensor system that may (i) recognize complex motion patterns, (ii) be self-powered, (iii) estimate a location and direction of an impact, (iv) compare observed patterns to reference patterns, (v) aggregate data from various sources, (vi) share resources with other user devices, (vii) be continuously available, (viii) adaptively learn reference patterns, (ix) provide feedback by comparing to reference patterns, (x) optimize/refine reference patterns over time, (xi) estimate a recovery time, (xii) alert users of potential injuries, (xiii) integrate with sensors in facilities and/or map-based data, (xiv) collect proximity data with respect to other users, boundaries of a playing surface and/or an object of contention, (xv) track an injury history of a user, (xvi) aggregate previous injury history with context data, (xv) determine unsafe scenarios, (xvi) iteratively determine forces and/or torques throughout the body, (xvii) measure neck strain and/or (xviii) recommend replacement of performance equipment.

BRIEF DESCRIPTION OF THE DRAWINGS

These and other objects, features and advantages of the present invention will be apparent from the following detailed description and the appended claims and drawings in which:

DETAILED DESCRIPTION OF EMBODIMENTS

Figure 1A:
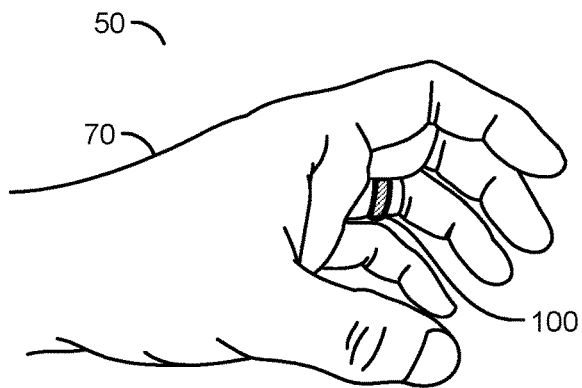
FIGS. 1a-c are diagrams illustrating an example embodiment.
Figure 1B:
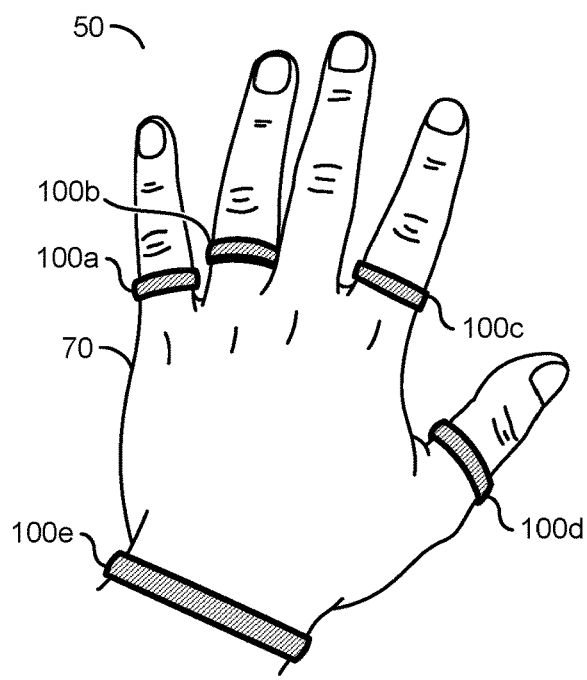
Figure 1C:
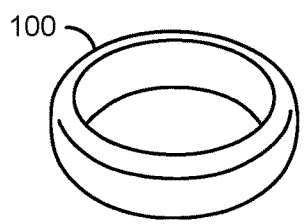

Referring to FIGS. 1a-c, diagrams of a system 50 are shown in accordance with an embodiment of the present invention. The system 50 generally comprises a user 70 and a block (or circuit) 100. The circuit 100 may be a wearable user input device. The wearable user input device 100 is shown as a ring. However, the wearable user input device 100 may be varied to meet the design criteria of a particular implementation. The wearable user input device 100 may have a minimal user interface. The wearable user input device 100 may be designed to be a subtle item. For example, the wearable user input device 100 may be indistinguishable from a conventional ring, wrist band and/or other wearable item.

Referring to FIG. 1b, the system 50 is shown implementing a plurality of wearable user input devices 100a-100e. The wearable user input devices 100a-100e may be worn on different locations. Wearing a plurality of the wearable user input devices 100a-100e may allow for a collection of user input from various locations on the body of the user 70, provide a greater amount of data and/or provide more accurate input. For example, the wearable user input devices 100a-100e worn on the hand of the user 70 may provide detailed information of the movement of the hand.

The wearable user input devices 100a-100e may be designed to fit various body parts of the user. For example, the wearable user input devices 100a-100d are shown as rings configured to be wearable on the fingers of the user 70. In another example, the wearable user input device 100e is shown as a wrist band configured to be worn on the wrist of the user 70. The type, number, and/or location of the wearable user input device 100 may be varied to meet the design criteria of a particular implementation.

The wearable user input device 100 may be ubiquitous, continuously available, and/or offer hands-free input of commands and/or data into mobile and/or network-based computing services. The wearable user input device 100 may allow for discreet input and/or sense subtle movements. For example, slight differences in gestures and/or movements may be detected that might otherwise be undetectable by the user 70 and/or others (e.g., a coach, a parent and/or a trainer). Subtle and/or slight differences in movement patterns may be the difference between a successful performance and an unsuccessful performance of an action. For example, a slight rotation of the wrist when swinging a golf club may result in a different angle of contact with a golf ball. Differentiating small differences in patterns of movements when performing an action may reduce the risk of injury.

Figure 2A:
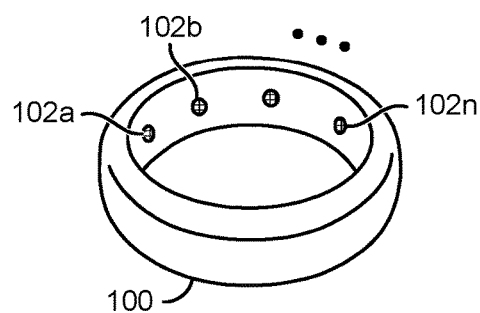
FIGS. 2a-c are diagrams illustrating a wearable user input device.
Figure 2B:
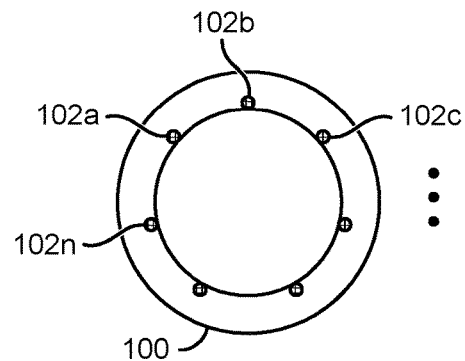

Referring to FIG. 2a and FIG. 2b, diagrams illustrating the wearable user input device 100 are shown. The wearable user input device 100 generally comprises sensors 102a-102n. The sensors 102a-102n may be designed to detect subtle finger/body motions and/or gesture patterns. For example, the sensors 102a-102n may be tri-axial accelerometers and/or pitch-tilt roll sensors. The sensors 102a-102n may measure motion and/or directional changes. Combinations of motions and/or directional changes may be recognized as gesture and/or movement patterns. More details on sensors and identifying gesture patterns may be found in "WristQue: A Personal Sensor Wristband", by Brian D. Mayton, IEEE International Conference on Body Sensor Networks (BSN), May 2013, which is hereby incorporated by reference in its entirety.

Figure 2C:
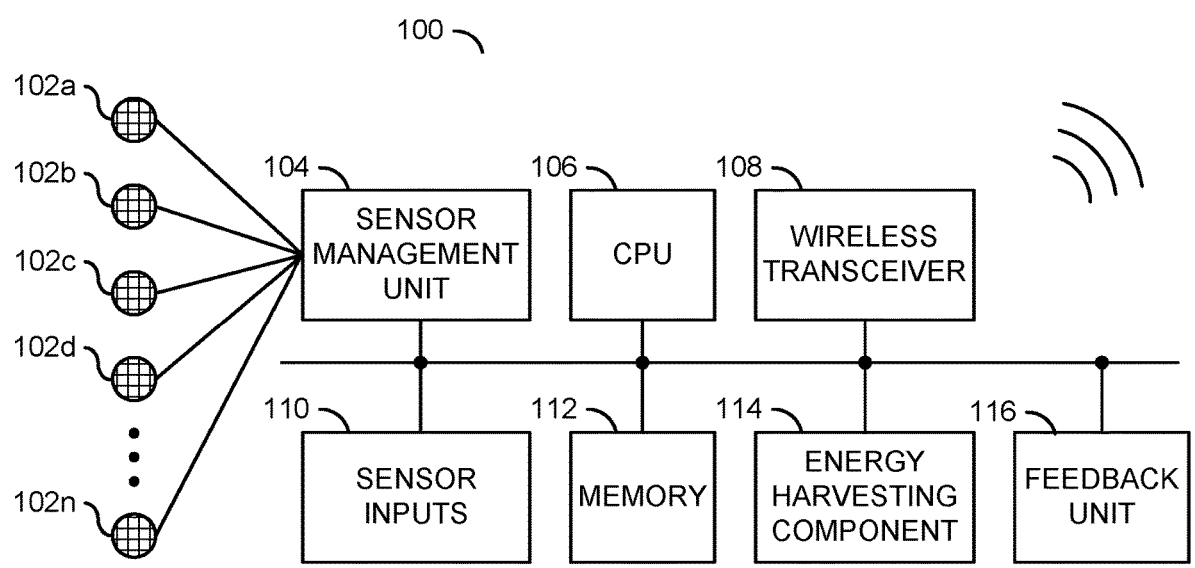

Referring to FIG. 2c, a block diagram of the wearable user input device 100 is shown. The wearable user input device 100 generally comprises the sensors 102a-102n, a block (or circuit) 104, a block (or circuit) 106, a block (or circuit) 108, a block (or circuit) 110, a block (or circuit) 112, a block (or circuit) 114, and a block (or circuit) 116. The circuit 104 may be a sensor management unit. The circuit 106 may be a central processing unit (CPU). The circuit 108 may be a wireless transceiver. The circuit 110 may be sensor inputs. The circuit 112 may be a memory. The circuit 114 may be an energy harvesting component. The circuit 116 may be a feedback unit. While the wearable user input device 100 is shown comprising the CPU 106 and/or the memory 112, the design of the wearable user input device 100 may be varied to meet the design criteria of a particular implementation. In one example, the wearable user input device 100 may not have the CPU 106 and/or the memory 112. The wearable user input device 100 may rely on another user input device for the functionality provided by the CPU 106 and/or the memory 112.

The wearable user input device 100 may be in the form of a continuously worn ring and/or other wearable item. In one example, the user 70 may wear the ring on a finger. In another example, the user 70 may wear the wearable user input device 100 as a wristband on the wrist. In yet another example, the wearable user input device 100 may be worn as a headband on the head of the user 70. In still another example, the wearable user input device 100 may be worn as a part of sports/performance equipment (e.g., a hockey glove, a shoulder pads, shin guards, shoes, skates, a stick, knee pads, a helmet, a bat, etc.)

The wearable user input device 100 may include an array of sensors 102a-102n around the inner surface. The sensors 102a-102n may detect pressure, activity, and/or directional motion. In one example, the sensors 102a-102n may be implemented as a 3-axis accelerometer, 3-axis gyroscope, and 3-axis magnetometer combined into a sensor fusion unit. The sensor fusion unit may detect direction, motion, and/or absolute orientation. In another example, the sensors 102a-102n may be implemented as a 12-axis sensor platform with ambient light detection, a barometer, and/or a thermometer in one unit. In another example, the sensors 102a-102n may be a sensor fusion unit configured to include electrocardiography (ECG) and/or capacitive sensors.

The sensor fusion unit may be configured with processing capabilities to provide additional data to determine context and/or motion of the user 70. Other examples of sensors may include pressure sensors to determine muscle relaxation/contraction, ECG sensors to determine heart rate variability, capacitive sensors to determine sweat levels, and/or motion sensors to determine emotional state/attitude based on jerky or calm movement of the hands. More details on sensor fusion units may be found in "The Role of Sensor Fusion and Remote Emotive Computing (REC) in the Internet of Things", by Kaivan Karimi, June 2013, which is hereby incorporated by reference in its entirety.

The wearable user input device 100 may be self-powered based on harvesting power from the motion of the user 70. Power may be harvested using the energy harvesting component 114. Sensor patterns from finger motions, body movement patterns and/or gestures may be associated with a finite set of available commands, patterns and/or classifications based on a user context. The user context may be determined automatically and/or adaptively based on a combination of personal, environmental and/or location-based data.

The sensor management unit 104 may receive input signals detected by the sensors 102a-102n. The sensors 102a-102n may be coupled to the sensor management unit 104. In one example, the sensor management unit 104 may gather motion data from each of the sensors 102a-102n. Motion data from one of the sensors 102a-102n may not be enough to determine a gesture and/or an action. The sensor management unit 104 may be configured to manage the data received from multiple sensors at the same time. The motion data gathered by the sensor management unit 104 may be used to detect a gesture/movement pattern.

The CPU 106 may be configured to provide processing capabilities to the wearable user input device 100. The CPU 106 may be connected to the other components by a common bus. The CPU 106 may store sensor data in the memory 112 and/or transmit sensor data to a remote device using the wireless transceiver 108.

The wireless transceiver 108 may be configured to send data from the wearable user input device 100 and/or receive data sent to the wearable user input device 100. The wireless transceiver may send/receive data to external devices and/or contact remote and/or cloud services. The wireless transceiver 108 may include support for wireless communication by one or more wireless protocols such as Bluetooth®, ZigBee®, IEEE 802.11, IEEE 802.15, IEEE 802.15.1, IEEE 802.15.2, IEEE 802.15.3, IEEE 802.15.4, IEEE 802.15.5, and IEEE 802.20.

The sensor inputs 110 may be configured to sense various types of input. For example, the additional sensor inputs 110 may include a tri-axial accelerometer and/or a pitch-tilt-roll sensor in the same component. For example, the additional sensor inputs 110 may measure motion and/or directional changes. In another example, the additional sensor inputs 110 may include an integrated 9-axis absolute orientation sensor fusion module. In one example, the integrated 9-axis absolute orientation sensor fusion module may be the Bosch BNO055 intelligent 9-axis "Absolute Orientation Sensor", which integrates a triaxial 12-bit accelerometer, a triaxial 16-bit gyroscope, a triaxial geomagnetic sensor, a 32-bit microcontroller, and sensor fusion algorithms.

The memory 112 may be configured to store data and/or instructions for the wearable user input device 100. The memory 112 may store context information. The context information may be used to determine the particular command to issue and/or the type of pattern/action to monitor based on a given gesture. The list of available commands and/or patterns may also be stored in the memory 112.

The energy harvesting component 114 may be configured to provide power for the wearable user input device 100. Use of the wearable user input device 100 may be based on motion. Accelerometers may be configured to translate motion into electrical signals allowing the wearable user input device 100 to be self-powered. The energy harvesting component 114 may capture energy from motion, heat, light, and/or through an external electromagnetic field, using energy harvesting methods. In one example, a small photovoltaic sensor may be configured to use light as a power source.

Energy captured by the energy harvesting component 114 may be stored by a battery and/or a capacitor functioning as a battery. The wearable user input device 100 may be in a low-power mode until the user 70 activates and/or wakes up the wearable user input device 100 through motion and/or gestures. In one example, the user 70 may intentionally activate and/or wake up the wearable user input device 100 through a prescribed motion such as tapping with the thumb and/or pressing down and holding. When the wearable user input device 100 is in an active state, the wireless transceiver 108 may begin transmitting subsequent motion, pressure and/or rotation signals via low-power wireless protocols.

The feedback unit 116 may provide corrective feedback to the user 70. The wearable user input device 100 may detect differences between observed patterns and reference patterns. For example, the user 70 may perform an action (e.g., throwing a ball). The observed motion of the action may be compared to a reference pattern of motion for the action. Corrective feedback may be presented to the user 70 based on differences between the observed motion and the reference pattern. Feedback provided by the feedback unit 116 may be comprised of haptic feedback, sound, and/or visual feedback. Feedback may be provided through the wearable user input device 100 and/or through an external computing device. Some of the sensors 102a-102n may be configured to provide feedback. The method of feedback provided by the feedback unit 116 may be varied based on the design criteria of a particular implementation.

Generating feedback may be based on context. For example, the context for generating feedback may be baseball swing training. Based on the context, relevant constraints may be formulated. Constraints may help determine and/or detect patterns, which may help generate relevant feedback to the user 70. Data from motion sensors may be processed together with a library and/or database of movement patterns under the constraint of performing a task using a particular piece of performance equipment (e.g., a bat). In one example, a constraint may be that two hands are used to swing a bat with one hand above the other hand. In another example, a constraint may be that while swinging the bat, the user will be standing.

Context information may be used to determine appropriate models (e.g., articulated models) for different tasks. Biomechanical models may have a high complexity. Using context information and/or constraints, the complexity of the biomechanical models may be reduced. For example, an articulated model may be selected based on the task and/or action performed. Generally, models may be selected based on not only having enough degrees of freedom to model the task/action but also providing enough constraints to reject noise and/or outliers. Context information may be used to determine the degrees of freedom and/or constraints.

Context information may be used to determine a vocabulary of tasks that are relevant. The relevant tasks may each be used to determine an appropriate biomechanical model. Once the context is known, recognition of the task/action may be easier to determine when executed by the user 70 during a performance.

Figure 3:
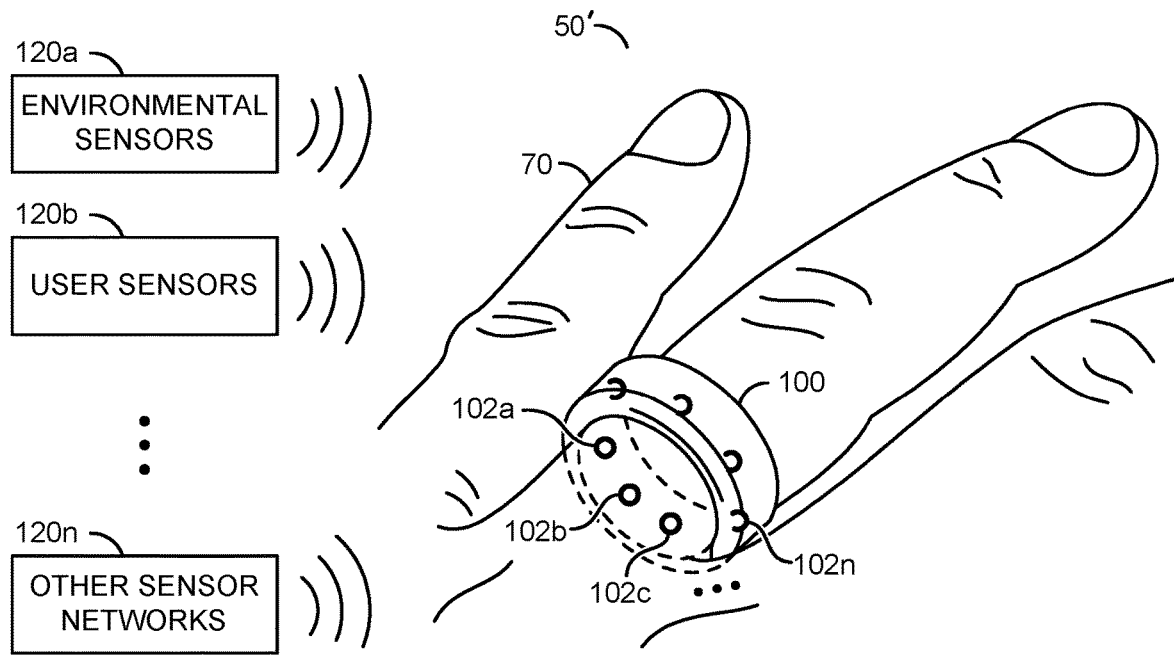
FIG. 3 is a diagram illustrating an example embodiment.

Referring to FIG. 3, a diagram illustrating an example embodiment of the system 50' is shown. The system 50' further comprises the blocks (or circuits) 120a-120n. The blocks 120a-120n may be various external sensors. For example, the external sensor 120a may be environmental sensors. In another example, the external sensors 120b may be user sensors. In yet another example, the external sensors 120n may be other sensor networks. The external sensors 120a-120n may include health sensors (e.g., to provide physiological data). The number and/or type of external sensors 120a-120n may be varied to meet the design criteria of a particular implementation.

The external sensors 120a-120n may be sensors on other self-powered devices (e.g., sensors on sports/performance equipment). The external sensors 120a-120n may be configured to communicate wirelessly. For example, the external sensors 120a-120n may send data to the wearable user input device 100. The wireless transceiver 108 may receive data from the external sensors 120a-120n. The sensor management unit 104 may interpret and aggregate data from the sensors 102a-102n, the sensor inputs 110, and/or the external sensors 120a-120n.

The wearable user input device 100 is shown being worn by the user 70. The sensors 102a-102n are shown making contact with the user 70 when the wearable user input device 100 is worn. The sensors 102a-102n may sense input from the user 70. The sensors 102a-102n arranged at various locations on the wearable user input device 100 may detect different motion data to send to the sensor management unit 104. Greater amounts of data may allow the wearable user input device 100 to more accurately predict and/or classify a gesture pattern and/or movement pattern.

Figure 4:
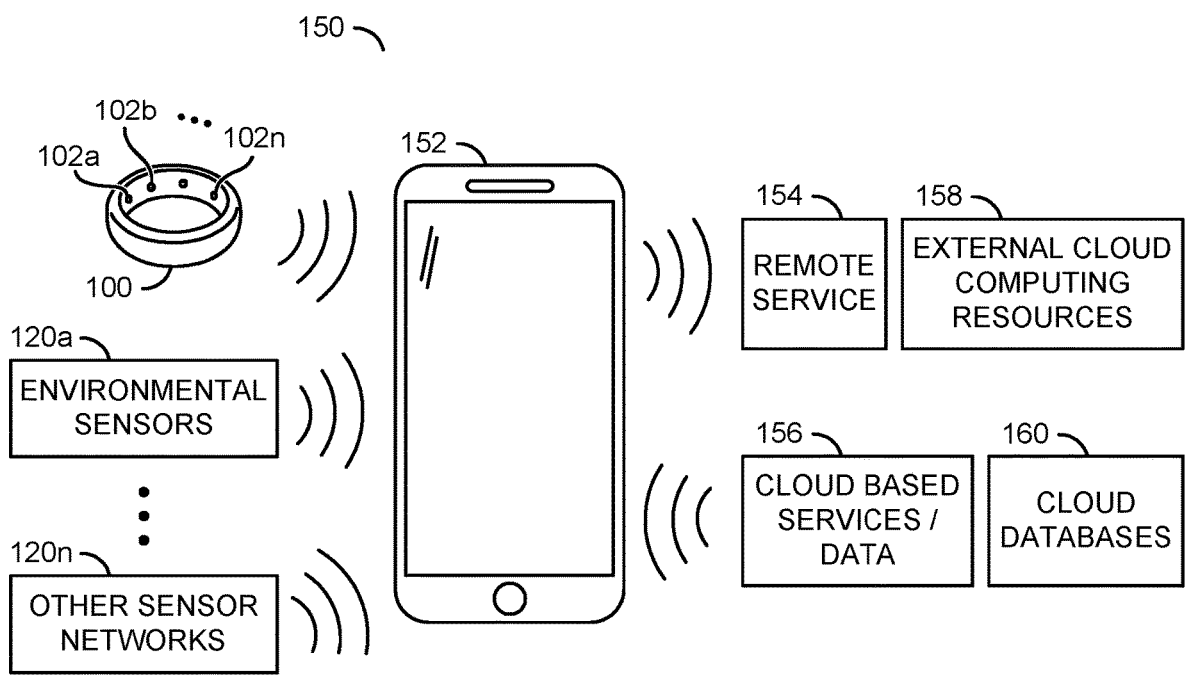
FIG. 4 is a diagram illustrating a wearable user input device communicating with a user device.

Referring to FIG. 4, a diagram illustrating a system 150 is shown. The system 150 may be the wearable user input device 100 communicating with a user device. The system 150 generally comprises the wearable user input device 100, the sensors 102a-102n, the external sensors 120a-120n, a block (or circuit) 152, a block (or circuit) 154, a block (or circuit) 156, a block (or circuit) 158, and a block (or circuit) 160. The circuit 152 may be a user input device. In one example, the user input device 152 may be a smartphone. In another example, the user input device 152 may be a tablet computer (or device). The block 154 may be remote services. The block 156 may be cloud based services/data. The block 158 may be external cloud based computing resources. The block 160 may be one or more cloud based databases.

The smartphone 152 may provide user I/O. For example, the smartphone 152 may have a user interface to allow the user 70 to send instructions to the wearable user input device 100, the remote services 154 and/or the cloud based services/data 156. The smartphone 152 may have a user interface to allow the wearable user input device 100 to send prompts and/or instructions to the user 70.

The wearable user input device 100 may leverage the processing power of the smartphone 152. The wearable user input device 100 may send data from the sensors 102a-102n via the wireless transceiver 108 to the smartphone 152. The processing power of the smartphone 152 may be used to process data received from the sensors 102a-102n.

The smartphone 152 may send data to the wearable user input device 100. For example, the additional processing power of the smartphone 152 may be used to recognize gesture patterns more accurately. In one example, the wearable user input device 100 may have the CPU 106 and the smartphone 152 may provide additional processing capabilities. In another example, the wearable user input device 100 may not have the CPU 106 and all the processing may be performed by the smartphone 152. The sensor inputs 110 may send data to the smartphone 152 via the wireless transceiver 108. Sensors in the smartphone 152 may supplement various sensor data from the sensor inputs 110 and/or the sensors 102a-102n.

The smartphone 152 may provide memory for the wearable user input device 100. In one example, the wearable user input device 100 may have the memory 112 and the smartphone 152 may provide additional memory and/or data storage capabilities (e.g., a memory card in the expansion slot of a smartphone). In another example, the wearable user input device 100 may not have any memory available, with all of the available memory being provided by the smartphone 152.

The wearable user input device 100 may transmit signals to the smartphone 152. The smartphone 152 may be configured to process signals to identify a pattern. The smartphone 152 may also associate the pattern with a best match to a fixed table of input commands and/or reference patterns. In one example, the reference pattern may be the user 70 performing a shot (e.g., a shot in hockey or a shot in soccer). In another example, the reference pattern may be the user 70 performing a pass (e.g., a pass in hockey or a pass in soccer).

Interpretation of the observed pattern received from the wearable user input device 100, and the table of available reference patterns that will be matched to the signal and/or observed pattern may be context dependent. In one example, context may be selected intentionally by the user 70 on the smartphone 152 (e.g., setting a practice mode and/or a competitive/game mode manually on the smartphone 152). In another example, the context may be determined automatically based on rules set up by the user 70 and/or adaptively determined over time based on user behavior.

For example, when a GPS location of the smartphone 152 indicates the user 70 is at a football field the context may then be determined to be a football training context. In another example, when a GPS location indicates the user 70 is at an ice rink, the context may then be determined to be a hockey game context. In another example, when the smartphone 152 is in motion outdoors at a particular speed (e.g., faster than 5 mph) the context may then be determined to be a running mode context.

The smartphone 152 may confirm commands with a voice prompt. For example, the voice prompt may be "tap the ring if you meant Football Practice mode". In another example, "change context" may be a defined command from the smartphone 152. In yet another example, double tapping the wearable user input device 100 may determine a context and/or pattern classification and the smartphone 152 may use voice prompts to help the user 70 select from a number of available contexts and/or classifications. Additional inputs for context and/or classification determination may be sensors onboard the smartphone 152. The sensors onboard the smartphone 152 may include location, date/time, calendar entries, recent communications via phone, text or email, motion, pitch/tilt/roll, compass bearing, ambient noise, vibration and motion (e.g., in an exercise context), lighting, temperature and/or barometric pressure (e.g., in indoor or outdoor context).

The cloud based services and/or data 156 may be accessed by the smartphone 152. The cloud based services and/or data may determine context. For example, the cloud based services and/or data may provide information including a places database to determine the nature of the location (e.g., restaurant, store, business, arena, park, sports field and/or other location), location-based data from sensor networks, and/or other geotagged data. The external cloud computing resources 158 may be used for processing data. The data processed by the cloud computing resources 158 may be stored in the cloud databases 160. Additionally, other sensor data from the external sensors 120a-120n such as health sensors may provide information to determine context.

The wearable user input device 100 may be configured to implement different contexts. An input gesture may map to one function/command/reference pattern in one context, and the same input gesture may map to a different function/command/reference pattern in a different context. For example, an observed input pattern may correspond to an action such as throwing (e.g., data from sensors detecting motion of the arm, wrist and/or shoulder). In the context of a baseball field, the observed input pattern of a throw may map to a reference pattern for pitching. However, in another example context of a football field the observed input pattern of a throw may map to a reference pattern for throwing a football. In another example, an input command "tap the ring with a finger" may map to a command for providing information on the heart-rate, distance traveled, current speed, or some other relevant exercise-related information.

Light level may be used to determine a context (e.g., different contexts if it is light or dark). In one example, light may be used as an input and/or part of a combination of input vectors. A light sensor (e.g., a small photovoltaic sensor and/or an infrared sensor) may be one of the sensor inputs 110. The user 70 may cover and/or uncover the light sensor to issue a command and/or initiate a particular context. For example, if the sensors 102a-102n and/or the sensor inputs 110 determine it is dark (e.g., a small amount of light input), and the orientation of the wearable user input device 100 is down it may indicate that the hand of the user 70 is concealed (e.g., in a glove). The wearable user input device 100 may then detect and/or observe movement patterns based on the context of a hand in a glove (e.g., a baseball glove). For example, when the hand of the user 70 is in a baseball glove, the user 70 may be playing baseball.

Generally, the precise detection of absolute motion and/or orientation may be difficult to obtain reliably. Movement patterns may be detected and learned. The movement patterns may be classified within a context. By associating the movement patterns within a context, machine learning techniques may classify the movement pattern even when precise data on motion, orientation, and/or position are unavailable. For example, if a context of golf is known the movement patterns of a swing may be classified as a hook. In another example, if a context of golf is known the movement patterns of a swing may be classified as a slice.

Figure 5:
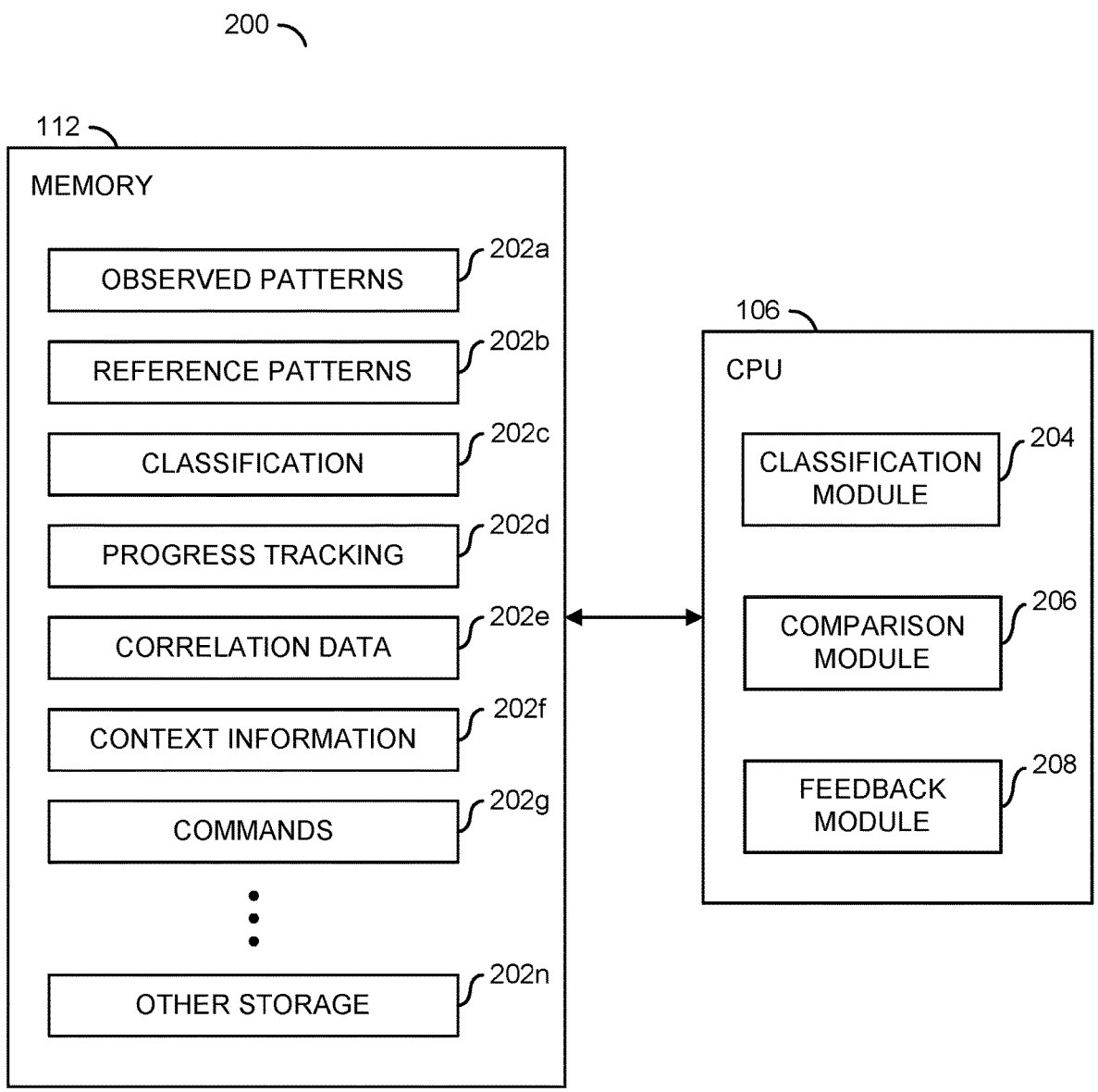
FIG. 5 is a diagram illustrating a detailed example of a memory and processor.

Referring to FIG. 5, a detailed example 200 of the memory 112 and the CPU 106 is shown. The memory 112 generally comprises blocks (or circuits) 202a-202n. The circuits 202a-202n may be memory storage. The CPU 106 generally comprises a block (or circuit) 204, a block (or circuit) 206 and a block (or circuit) 208.

The circuit 204 may be a classification module. The classification module 204 may classify observed patterns based on a closeness to reference patterns. The circuit 206 may be a comparison module. The comparison module 206 may compare observed patterns with reference patterns. The circuit 208 may be a feedback module. The feedback module 208 may provide feedback to the user 70 (e.g., through the feedback unit 116) based on detected differences with the reference patterns. For example, the feedback module 208 may comprise haptic, audio, and/or visual feedback to the user 70. The feedback from the feedback module 208 may be sent directly to the wearable user input device 100, a particular one or more of a plurality of wearable user input devices 100, and/or the user device 152.

The memory storage 202a-202n may represent data stored in the memory 112. For example, the memory storage 202a-202n may include examples such as observed patterns 202a, reference patterns 202b, classification data 202c, progress tracking 202d, correlation data 202e, context information 202f, commands 202g, and/or other storage 202n. The arrangement and/or type of data stored in the memory storage 202a-202n may be varied according to the design criteria of a particular implementation. In some embodiments, one or more of the memory storage 202a-202n may be stored in the user device 152, the cloud based services/data 156, the cloud databases 160, and/or the remote service 154.

The observed patterns 202a may be gestures and/or movement patterns of the user 70 detected by one or more of the user input devices 100, the sensors 102a-102n and/or the external sensors 120a-120n. The observed patterns 202a may be stored to allow for further processing (e.g., comparison, correlation, progress tracking, etc.) The observed patterns 202a may be detected when the user 70 performs an action.

The reference patterns 202b may be gestures and/or movement patterns observed by many users over time. For example, using machine learning techniques, a database of reference movement patterns may be developed. The reference patterns 202b may be an ideal and/or optimal movement pattern for performing a particular action. The reference patterns 202b may represent a safe performance of an action (e.g., a method of performing the action without causing injury and/or reducing the risk of injury).

The reference patterns 202b may be created by trainers and/or professionals (e.g., professional athletes performing the action). The reference patterns 202b may be developed by correlating the observed patterns 202a with success and/or failure of the actual performance result. In one example, a player who shoots and successfully scores a goal may represent a successful performance result. In another example, a player who shoots and sustains an injury may represent a failed performance result. Collecting data over time may lead to an improvement of the reference patterns 202b.

The classification data 202c may store a classification of the observed patterns 202a. The classification of the observed patterns 202a may be performed by the classification module 204. The classification data 202c may be based on how close the observed pattern 202a is to the reference pattern 202b. The classification data 202c may be based on context information. The classification data 202c may be based on information from one or more wearable user input devices 100, the sensors 102a-102n and/or the external sensors 120a-120n. The user may be able to verify and/or correct the classification data 202c.

The classification of the observed pattern 202a may determine the type of action being performed. Some actions may have similar movement patterns. To provide training and/or feedback, the observed patterns 202a may need to be correlated with the proper reference patterns 202b. For example, the observed pattern 202a may be detected and the context data may indicate the user 70 is playing hockey. The observed pattern 202a may indicate a large back swing was performed.

The classification module 204 may determine that the action performed is classified as a slap shot. The observed pattern 202a may be stored in the classification data 202c as a slap shot. A reference pattern for a slap shot stored as one of the reference patterns 202b may be used for comparison with the observed pattern 202a (e.g., by the comparison module 206).

The progress tracking 202d may store progress information about the user 70. Over time, the user 70 may perform many actions (e.g., the observed patterns 202a) that may be compared with the reference patterns 202b. The progress tracking 202d may store the level of success and/or failure of the user 70 (e.g., the performance result). In one example, the level of success and/or failure may be based on a comparison of the observed patterns 202a to the reference patterns 202b. In another example, the level of success and/or failure may be monitored by another person (e.g., a coach and/or a trainer providing feedback using the user device 152). The progress tracking 202d may provide a visualization, keep score, and/or match actual performance and usage to an assigned program and/or curriculum. The progress tracking may be performed by the feedback module 208.

The correlation data 202e may store a correlation of observed patterns and performance data to determine new reference patterns. New reference patterns may be created for specific sports, moves/actions, and/or athlete profiles. For example, different users may have various abilities, body types, and/or limitations. A reference pattern for one user may not be suitable for another user. For example, one reference pattern for one action may be optimized/refined for a high-end athlete such as a professional. A low-end athlete may sustain an injury if attempting to perform a reference pattern optimized/refined for a professional athlete. In another example, a reference pattern for the same action may be optimized/refined for a recreational athlete.

The context information 202f may store information about the context of a motion/action. The commands 202g may store information about various commands associated with various movement patterns/gestures (e.g., a confirmation/verification gesture). More information on gestures and/or contexts may be found in U.S. Ser. No. 14/220,378, filed Mar. 20, 2014, which is hereby incorporated by reference in its entirety.

Figure 6:
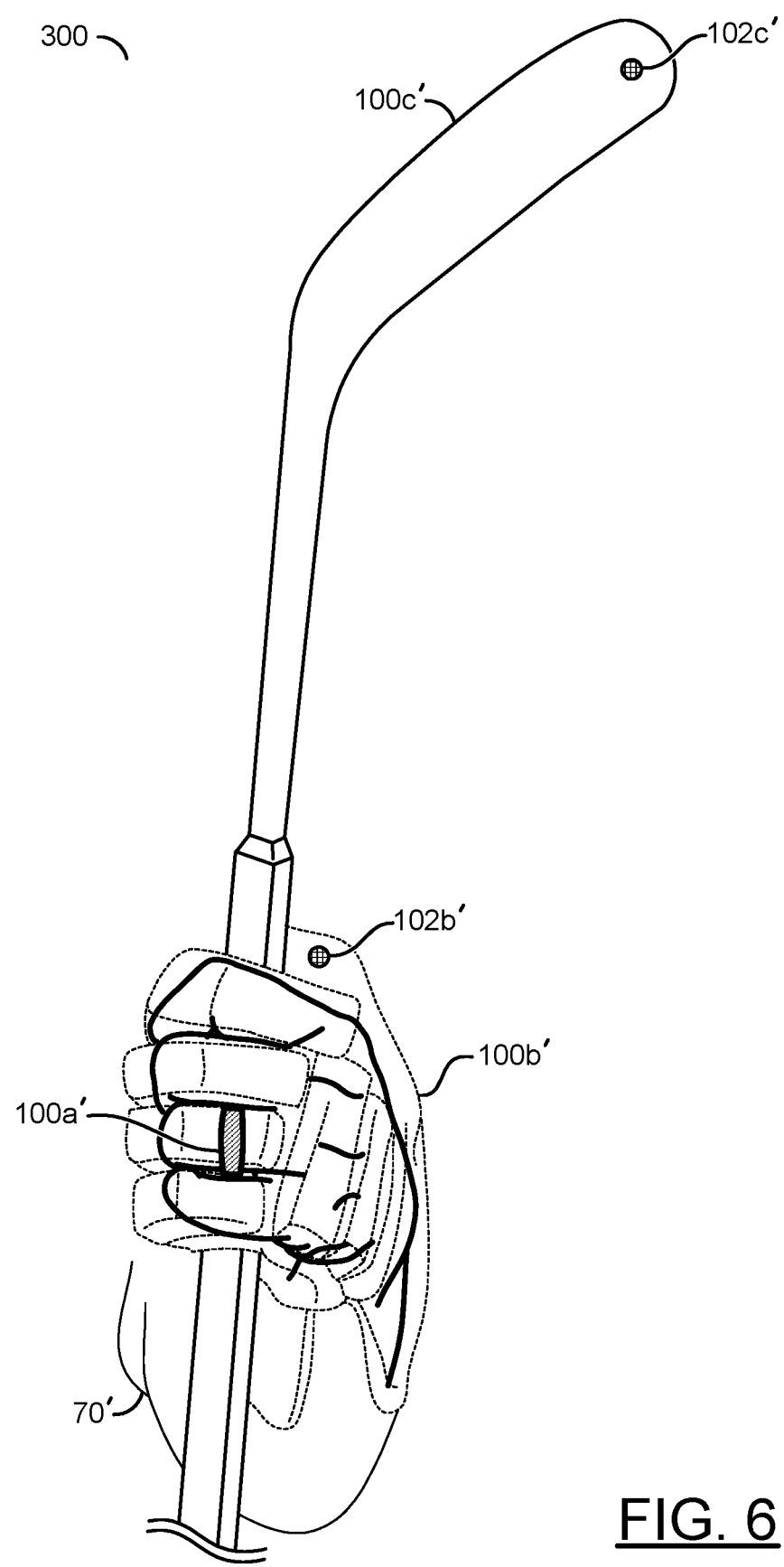
FIG. 6 is a diagram illustrating an example sports embodiment.

Referring to FIG. 6, an example sports embodiment 300 is shown. The example sports embodiment 300 may be a hand of a hockey player 70'. The hand of the hockey player 70' is shown wearing a plurality of wearable user input devices 100a'-100c'. The hockey player 70' may be wearing more wearable user input devices than shown in the example sports embodiment 300. Each of the wearable user input devices 100a'-100c' may have corresponding sensors. For example, the wearable user input device 100b' is shown comprising a corresponding sensor 102b' and the wearable user input device 100c' is shown comprising a corresponding sensor 102c'. However, each of the wearable user input devices 100a'-100c' may have a plurality of sensors. The number of sensors may correspond to the size/shape of the wearable user input devices (e.g., the performance equipment) and/or the range of motion that may be observed. For example, the number of sensors may be increased to ensure the collection of useful data.

In one example, the wearable user input devices may be performance equipment. The performance equipment may be items normally worn and/or used while playing a particular sport and/or during a performance. Generally, the hockey player 70' wears protective equipment (e.g., a helmet, shoulder pads, gloves, elbow pads, pants, shin pads, skates, etc.) Each piece of equipment worn by the hockey player 70' may be the performance equipment (e.g., one of the wearable user input devices 100). The type and/or amount of performance equipment worn may vary based on the sport being played. The amount of wearable user input devices worn and/or the number of sensors corresponding to each wearable user input device may be varied according to the design criteria of a particular implementation.

The hockey player 70' is shown wearing the ring 100a', the hockey glove 100b', and using the hockey stick 100c'. The ring 100a' may detect movement of the fingers of the hockey player 70'. The hockey glove 100b' may detect movement of the hand, wrist and/or forearm of the hockey player 70'. The hockey stick 100c' may detect the movement of the stick by the player 70' and/or interactions with a puck. For an example where the hockey player 70' performs the actions of shooting the puck, the ring 100a' may record the grip of the hand on the shaft of the stick, the hockey glove 100b' may record the motion and/or rotation of the hands and arm, and the hockey stick 100c' may record the flex, angle, and/or direction of the stick during and after (e.g., the follow-through) the shooting action is performed.

The data from the various sensors of the equipment may be combined to provide details of the motion of the hockey player 70'. The details provided may be the observed pattern. The observed pattern may be compared with a reference pattern. In some embodiments, the relative motion of the wearable user input devices may provide useful information (e.g., the fit and/or durability of the equipment). For example, if the foot of the hockey player 70' is moving too much inside the skate the hockey player 70' may be wearing a skate that is too large. In another example, if the hockey stick 100c' is determined to be flexing too much compared to the force applied by the player 70' the hockey stick 100c' may be damaged.

Figure 7:
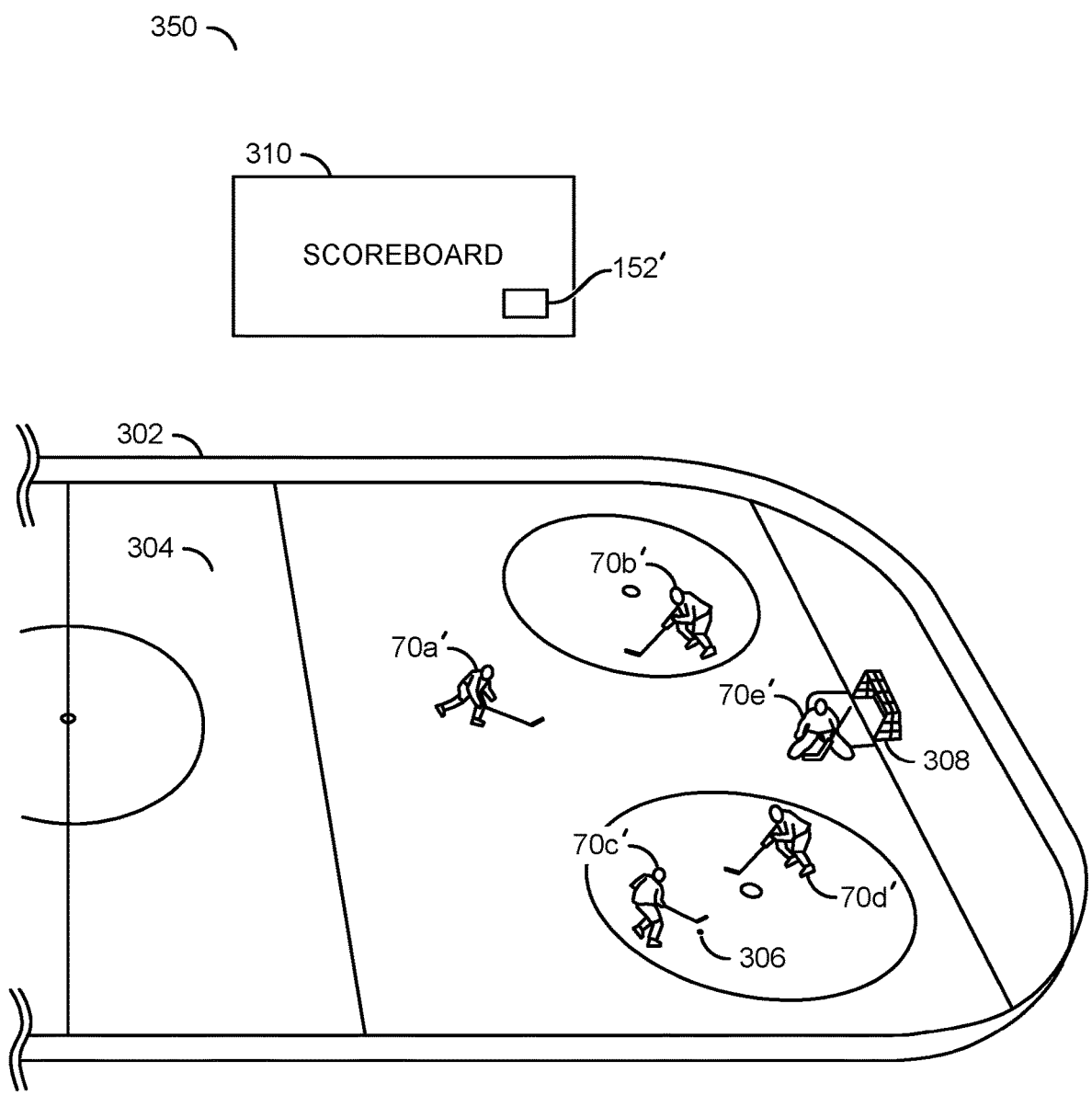
FIG. 7 is a diagram illustrating an example of a team indoor sport embodiment.

Referring to FIG. 7, an example team indoor sport embodiment 350 is shown. The example team indoor sport embodiment 350 may be a hockey game. The example hockey game 350 may be comprised of the players 70a'-70e', the user device 152', a boundary (e.g., boards) 302, a playing surface (e.g., ice) 304, an object of contention (e.g., puck) 306, a goal 308, and a facility fixture (e.g., a scoreboard) 310.

Practical considerations (e.g., in contact sports such as hockey, football, rugby, etc.) may prevent the players 70a'-70e' from carrying the user device 152'. For example, the user device 152' may be in the possession of another person (e.g., a trainer or a coach). In the example shown, the user device 152' is shown as part of the scoreboard 310. In other embodiments, the user device 152' may be part of a different facility fixture (e.g., television broadcast equipment, a computer network in the facility, etc.). For example, the scoreboard 310 may already be configured to track certain statistics (e.g., goals, shots, penalties). The user device 152' may be property of the sports facility and be configured to allow players and/or coaches to connect to the user device 152' and access collected data.

Each of the players 70a'-70e' may be wearing one or more wearable user input devices (as described in FIG. 6). The user device 152' may be configured to collect and/or process data received from the sensors of each of the players 70a'-70e'. Data processed by the user device 152' may be sent back to each of the players 70a'-70e' (e.g., in the form of feedback from the feedback module 208).

The boundary 302, the playing surface 304, the puck 306, the goal 308, and/or the scoreboard 310 may have sensors (e.g., the external sensors 120a-120n). The sensors on the players 70a'-70e', the external sensors 120a-120n, and/or the user device 152' may collect and/or process data to determine proximity data between the players 70a'-70e'. For example, the proximity data may provide positional data to a coach. In another example, the proximity data may provide feedback to the players 70a'-70e' (e.g., a warning to a player that is out of position, a warning to a player of a potential collision, etc.). The proximity data may be utilized in performances other than team sports. For example, proximity data may be utilized in a team performance (e.g., figure skating, synchronized swimming, etc.). In another example, proximity data may be utilized in a staged performance and/or a play. The proximity data may be useful to any group of users constituting a group pattern and/or interaction amongst users.

The proximity data may detect a proximity and/or orientation of each of the players 70a'-70e' with respect to the puck 306. The proximity data may determine a location on the playing surface 304 with respect to the boundary 302. The proximity data may determine the location of each of the players 70a'-70e'. The actions of the players 70a'-70e' may be determined with respect to the proximity data.

Through machine learning processes, patterns may be determined based on proximity data, actions of the players 70a'-70e', and/or data from the players 70a'-70e'. For example, the machine learning process may determine a pattern of a goal being scored when one of the players 70a'-70e' is out of position. In another example, the machine learning process may determine a pattern of a goal being scored while each of the players 70a'-70e' are in an expected position but while one of the players is fatigued. Coaches may use the data to develop strategies (e.g., positional play, when to change lines, etc.).

Other sports may include similar objects. For example, in basketball the boundary 302 may be court sidelines. In another example, in soccer the playing surface 304 may be a grass field. In yet another example, in baseball the object of contention 306 may be a ball. In still another example, in football the goal 308 may be an end zone. The type of sport and/or the objects used may be varied to meet the design criteria of a particular application.

Figure 8:
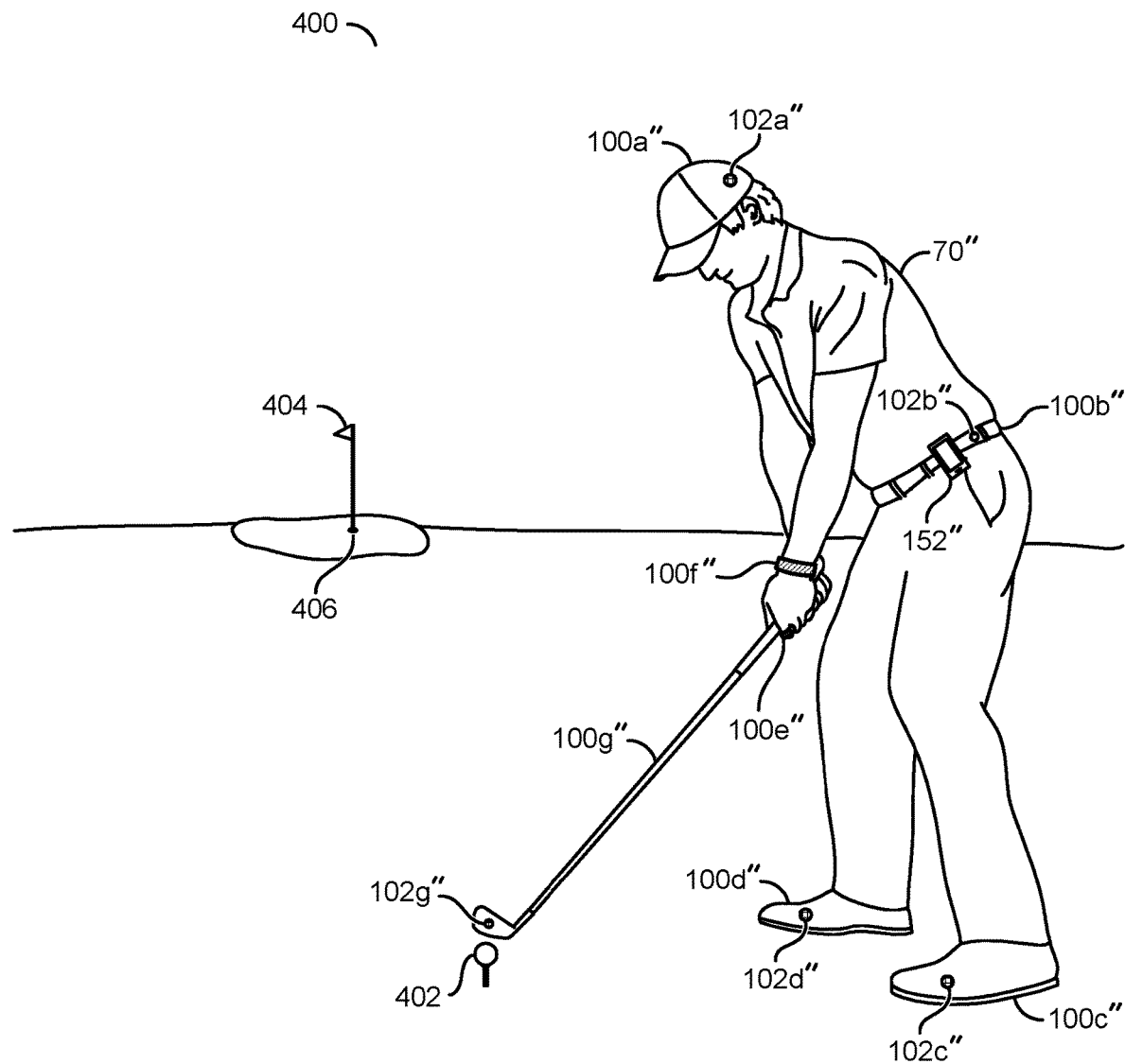
FIG. 8 is a diagram illustrating an example of an outdoor sport embodiment.

Referring to FIG. 8, an example 400 of an outdoor sport embodiment is shown. The example 400 comprises a golfer 70", a golf ball 402, a flagstick/pin 404, and a hole 406. The golfer 70" is shown wearing a plurality of wearable user input devices 100a"-100g". Each of the wearable user input devices 100a"-100g" may comprise a corresponding sensor 102a"-102g". However, each of the wearable user input devices 100a"-100g" may have a plurality of sensors. The number of sensors may correspond to the size/shape of the wearable user input devices and/or the range of motion that may be observed. For example, the number of sensors may be increased to ensure the collection of useful data. The golfer 70" is shown having the user device 152".

The wearable user input devices may be performance equipment. The performance equipment may be items normally worn and/or used while playing the sport. The golfer 70" is shown wearing a hat 100a", a belt 100b", a left shoe 100c", a right shoe 100d", a ring 100e", a wrist band 100f", and a golf club 100g". Each of the wearable user input devices 100a"-100g" may measure particular motions/actions of the golfer 70". The aggregated sensor data of the wearable user input devices 100a"-100g" may provide details on the action performed by the golfer 70".

For example, the hat 100a" may measure the head tilt of the golfer 70". The belt 100b" may measure the hip movement of the golfer 70". The left shoe 100c" and the right shoe 100d" may measure the direction of the feet of the golfer 70". The ring 100e" may measure the grip of the golfer 70". The wrist band 100f" may measure the wrist movement of the golfer 70". The golf club 100g" may measure the swing speed and form of the golfer 70". For example, the combined sensor data of the performance equipment 100a"-100g" may determine that the golfer 70" is making an error in movement pattern while performing a shot (e.g., the head is moving too much, the feet are pointed in the wrong direction, the grip is improper, etc.).

The aggregated sensor data of the wearable user input devices 100a"-100g" may be an observed pattern. The observed pattern may be classified as a particular action (e.g., a chip shot, a swing from the tee, a putt, etc.) by the classification module 204. The observed pattern may be compared to reference patterns for successful golf swings by the comparison module 206. The feedback module 208 may provide feedback to the golfer 70".

Feedback may be provided to the user device 152". Feedback may be provided to the performance equipment 100a"-100g" (e.g., haptic feedback, audio feedback, etc.) In some embodiments, the particular wearable user input device where the error in the observed pattern is detected may provide feedback. For example, if the golfer 70" is performing a swing and the observed pattern indicates the hips of the golfer 70" are not moving properly the belt 100b" may provide feedback (e.g., a slight vibration) to indicate an error. The golfer 70" may select the type and/or timing of the feedback (e.g., by using an interface on the user device 152"). For example, the golfer 70" may select a training mode that allows the wearable user input devices 100a"-100g" to provide feedback while performing a shot. In another example, the golfer 70" may select a competitive mode that prevents the wearable user input devices 100a"-100g" from providing feedback that may distract the golfer 70" (e.g., feedback may be gathered and later reported to the user device 152").

The golf ball 402, the flagstick/pin 404, and the hole 406 may have sensors (e.g., the external sensors 120a-120n). Data from the golf ball 402 may indicate the location of the ball to the golfer 70", a type of impact made by the golf club 100g", a distance traveled, a rotation of the golf ball 402, etc. The flagstick/pin 404 may determine a wind speed. The hole 406 may provide the golfer 70" information on distance and/or potential hazards between the golf ball 402 and the hole 406. For example, based on data from the external sensors 120a-120n (e.g., the golf ball 402, the flagstick/pin 404, and the hole 404) recommendations may be sent to the golfer 70" (e.g., on the user device 152"). A particular club selection, a swing speed, and/or a swing direction may be recommended. The recommendation may be the reference pattern. The golfer 70" may then attempt practice swings to match the reference pattern before performing a shot.

Information from the remote service 154, the cloud based services/data 156, the external cloud computing resources 158, and/or the cloud databases 160 may be acquired. For example, location and/or map-based data may be acquired. Stored reference patterns may be provided based on location data (e.g., GPS data). Statistics, observed patterns, and the success and/or failure of actions by the golfer 70" may be sent to the remote service 154, the cloud based services/data 156, the external cloud computing resources 158, and/or the cloud databases 160. Information from the golfer 70" may be used to optimize/refine the reference patterns (e.g., using machine learning techniques).

Figure 9:
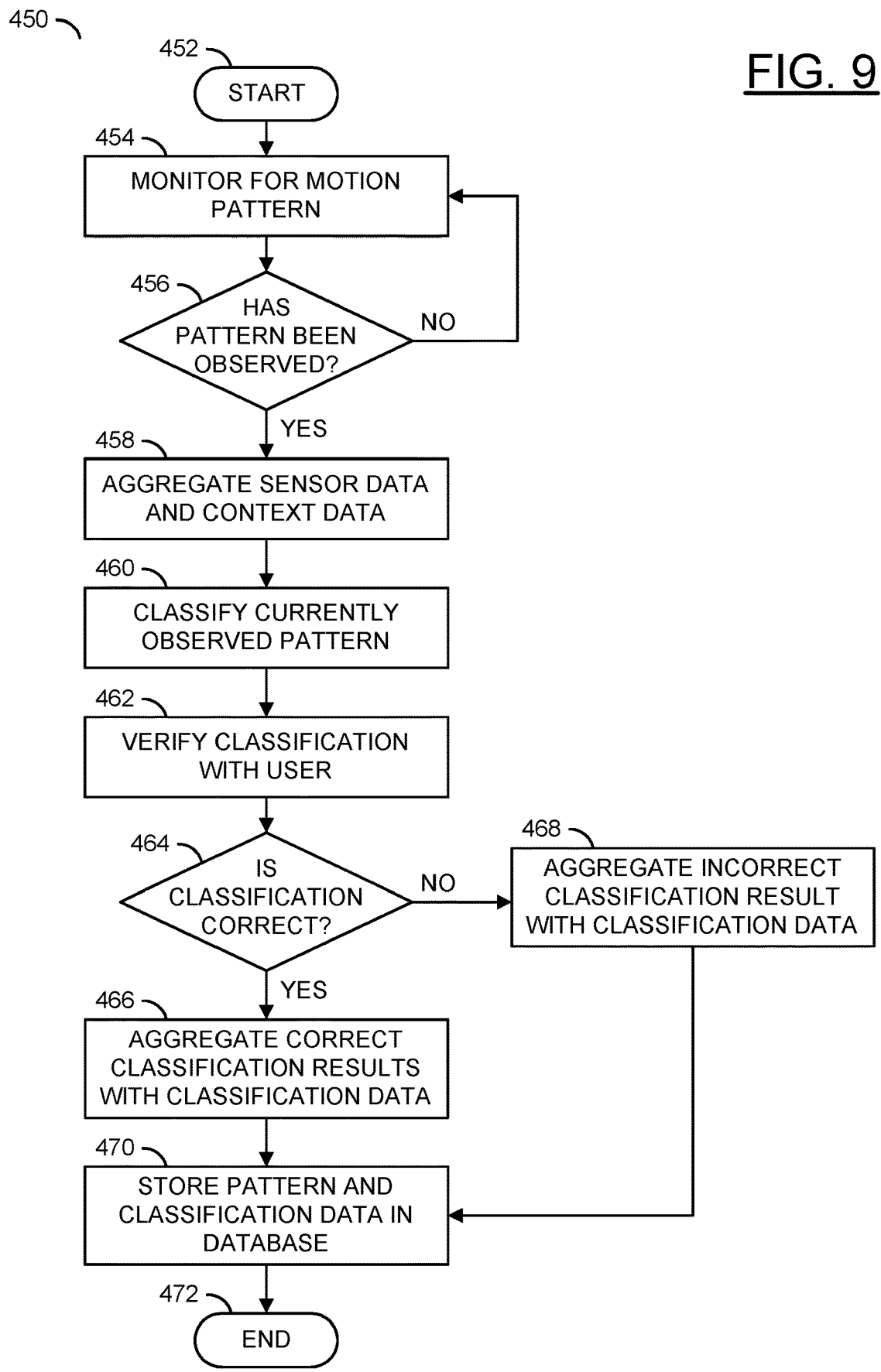
FIG. 9 is a flow diagram illustrating a machine learning method for classification of observed motion patterns.

Referring to FIG. 9, a flow diagram of a method (or process) 450 is shown. The method 450 may be a machine learning process for classification of observed motion patterns. The method 450 generally comprises a step (or state) 452, a step (or state) 454, a decision step (or state) 456, a step (or state) 458, a step (or state) 460, a step (or state) 462, a decision step (or state) 464, a step (or state) 466, a step (or state) 468, a step (or state) 470, and a step (or state) 472. The state 452 may start the method 450. The state 454 may monitor for a motion pattern. For example, a motion pattern may be an action. Next, the method 450 moves to the decision state 456.

If the decision state 456 determines a pattern has not been observed, the method 450 may return to the state 454. If the decision state 456 determines a pattern has been observed, the method 450 may move to the state 458. The state 458 may aggregate sensor data and context data (e.g., data from the sensors 102a-102n and/or the external sensors 120a-120n). Next, the state 460 may classify the currently observed pattern (e.g., using the classification module 204). The state 462 may verify the classification with the user. Next, the method 450 moves to the decision state 464.

If the decision state 464 determines the classification is correct, the method 450 may move to the state 466. The state 466 may aggregate the correct classification results with the classification data (e.g., the classification data 202c). Next, the method 450 moves to the state 470. If the decision state 464 determines the classification is not correct, the method 450 may move to the state 468. The state 468 may aggregate the incorrect classification result with the classification data (e.g., the classification data 202c). Next, the method 450 moves to the state 470. The state 470 may store the pattern and classification data in a database (e.g., the memory 112, the remote service 154, the cloud database 160, etc.) Next, the method 450 moves to the state 472, which ends the method 450.

Verification of the classification may be performed by the user and/or a coach/trainer. In one example, the user 70 may perform an action and the user may verify the classification by entering a command using the wearable user input device 100 (e.g., a pre-defined verification gesture). In another example, the user 70 may perform an action and the user may verify the classification with a voice command. In still another example, a coach/trainer may observe the user 70 perform an action and the coach/trainer may verify the classification of the action (e.g., using the user device 152). In yet another example, the currently observed pattern may be classified with a high enough level of confidence that no verification is performed.

The aggregation of data may be a machine learning process. When aggregating data for the reference patterns of movement, greater weight may be given to the data associated with the observed patterns of movement that correspond to a successful performance. In another example, when aggregating data for the reference patterns of movement, little weight, no weight and/or negative scaling factors may be given to data associated with the observed patterns of movement that do not correspond to a successful performance. As the aggregated results are stored in the database and more data is provided over time, the reference patterns may improve and/or reliably represent a greater number of actions.

Figure 10:
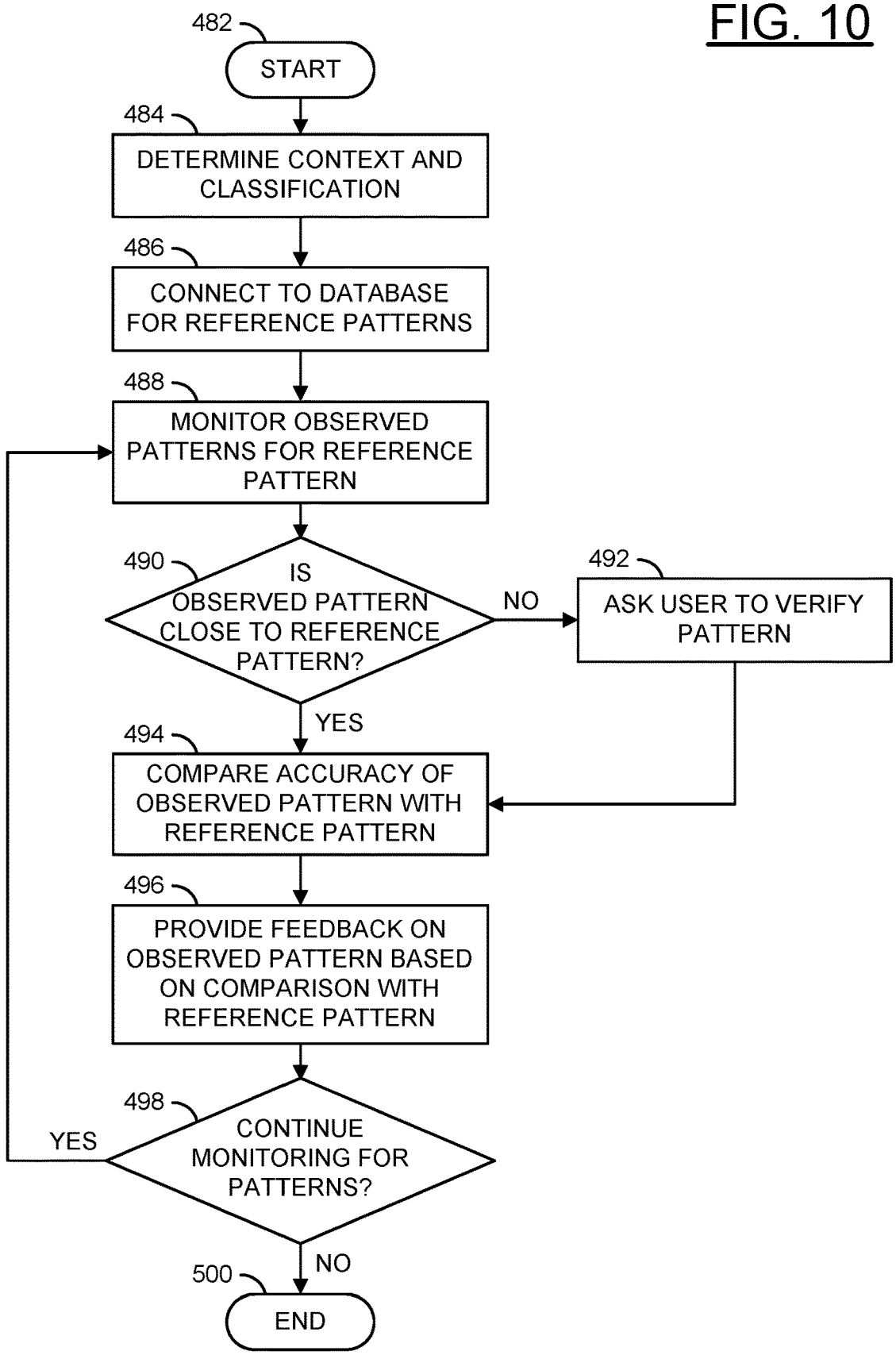
FIG. 10 is a flow diagram illustrating a method for comparing observed patterns to reference patterns.

Referring to FIG. 10, a flow diagram of a method (or process) 480 is shown. The method 480 may compare observed patterns to reference patterns. The method 480 generally comprises a step (or state) 482, a step (or state) 484, a step (or state) 486, a step (or state) 488, a decision step (or state) 490, a step (or state) 492, a step (or state) 494, a step (or state) 496, a decision step (or state) 498, and a step (or state) 500.

The state 482 may start the method 480. Next, the state 484 may determine context and classification of an action. The state 486 may connect to a database for reference patterns. The state 488 may monitor observed patterns for reference patterns. Next, the method 480 moves to the decision state 490.

If the decision state 490 determines the observed pattern is not close to the reference pattern, the method 480 moves to the state 492. The state 492 may ask the user to verify the pattern. Next, the method 480 moves to the state 494. If the decision state 490 determines the observed pattern is close to the reference pattern, the method 480 moves to the state 494. The state 494 may compare the accuracy of the observed pattern with the reference pattern (e.g., using the comparison module 206).

Next, the state 496 may provide feedback on the observed pattern based on the comparison with the reference pattern. Next, the method 480 moves to the decision state 498. If the decision state 498 determines to continue monitoring for patterns, the method 480 may return to the state 488. If not, the method 480 moves to the state 500, which ends the method 480.

The database of the reference patterns may be stored in the memory 112 (e.g., the reference patterns 202b), the remote service 154, and/or the cloud databases 160. Feedback may be provided by the feedback module 208. The amount/intensity of the feedback may be based on how close the observed pattern is to the reference pattern. The amount/intensity of the feedback may be based on a likelihood of injury to the user 70. The amount/intensity of the feedback may be varied to meet the design criteria of a particular implementation.

The observed pattern may be stored as one of the observed patterns 202a. The observed patterns 202a may be compared with the reference patterns 202b using the comparison module 206. If the observed patterns 202a are not close enough to be classified and/or compared to the stored reference patterns 202b the wearable user input device 100 and/or the user device 152 may verify the pattern the user 70 is attempting to perform. The user 70 may verify the pattern with a pre-defined input command using the wearable user input device 100 and/or using a voice command. For example, voice recognition may be utilized to verify the pattern.

The user device 152 may alert the user 70 of a low probability match to the reference pattern and display a confirmation prompt to the user 70. In another example, the user device 152 may send a voice alert of a low probability match to the user 70 and the user 70 may then respond with a voice response. The type of confirmation may be varied to meet the design criteria of a particular implementation.

Figure 11:
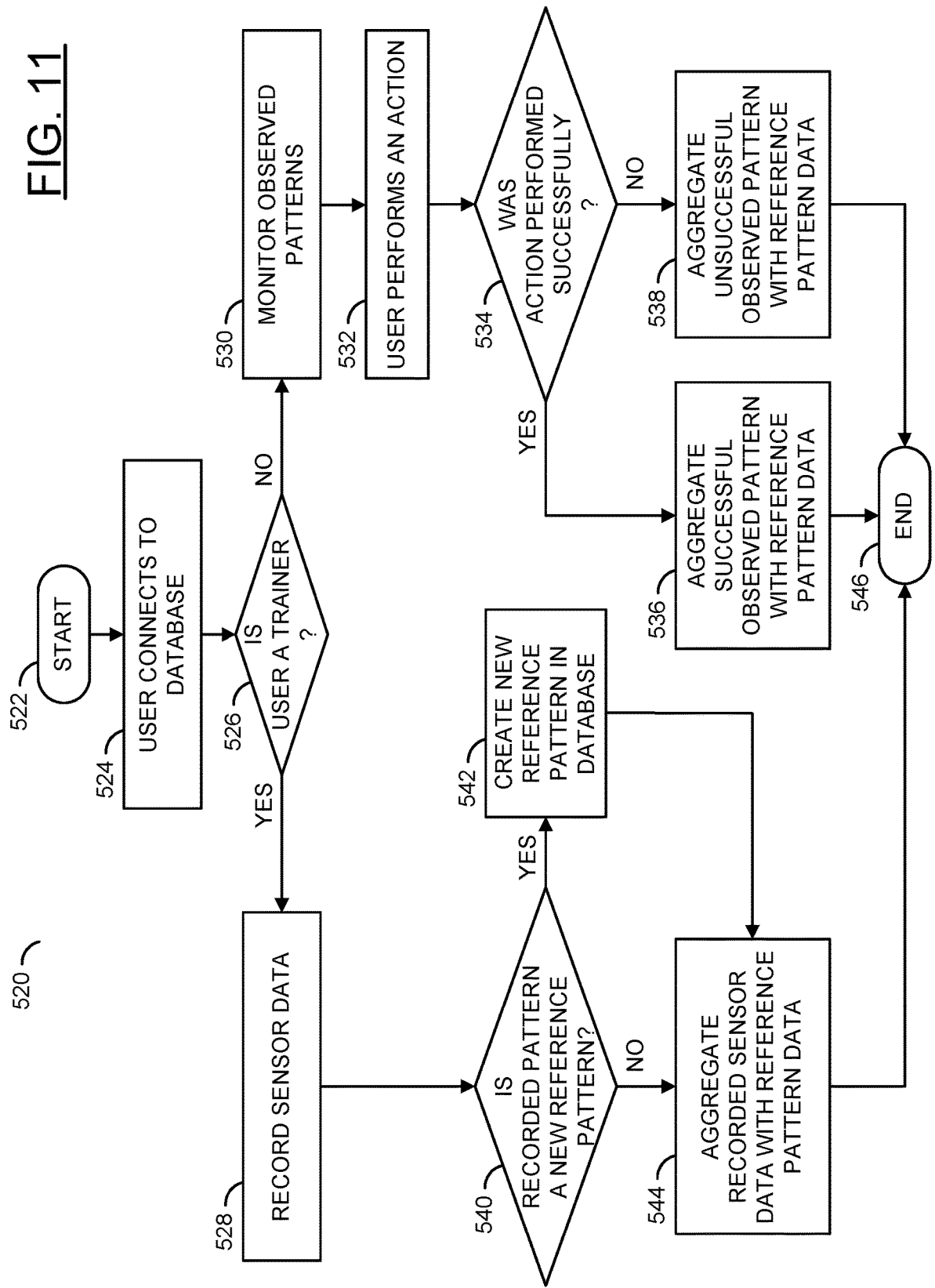
FIG. 11 is a flow diagram illustrating a machine learning method for determining reference patterns.

Referring to FIG. 11, a flow diagram of a method (or process) 520 is shown. The method 520 may be a machine learning method for determining reference patterns. The method 520 generally comprises a step (or state) 522, a step (or state) 524, a decision step (or state) 526, a step (or state) 528, a step (or state) 530, a step (or state) 532, a decision step (or state) 534, a step (or state) 536, a step (or state) 538, a decision step (or state) 540, a step (or state) 542, a step (or state) 544, and a step (or state) 546. The state 522 may start the method 520. In the state 524, the user 70 may connect to the database. Next, the method 520 moves to the decision state 526.

If the decision state 526 determines the user is a trainer, the method 520 moves to the state 528. The state 528 may record sensor data. Next, the method 520 moves to the decision state 540. If the decision state 526 determines the user is not a trainer, the method 520 moves to the state 530. The state 530 may monitor for observed patterns. Next, in the state 532 the user may perform an action. Next, the method 520 moves to the decision state 534.

If the decision state 534 determines the action was performed successfully, the method 520 moves to the state 536. The state 536 may aggregate the successful observed pattern with the reference pattern data 202b. Next, the method 520 moves to the state 546, which ends the method 520. If the decision state 534 determines the action was not performed successfully, the method 520 moves to the state 538. The state 538 may aggregate the unsuccessful observed pattern with the reference pattern data. Next, the method 520 moves to the state 546, which ends the method 520.

If the decision state 540 determines the recorded pattern is a new reference pattern, the method 520 moves to the state 542. The state 542 may create a new reference pattern in the database. Next, the method 520 moves to the state 544. If the decision state 540 determines the recorded pattern is not a new reference pattern, the method 520 moves to the state 544. The state 544 may aggregate the recorded sensor data with the reference pattern data 202b. Next, the method 520 moves to the state 546, which ends the method 520.

A trainer may have a user account in the cloud databases 160. The trainer may be a professional trainer having credentials for instructing users. For example, the trainer may be a weightlifting coach capable of demonstrating how to perform exercises with proper form to prevent injury. The trainer may be a trusted source for developing reference patterns. For example, greater weight may be given to the data associated with observed patterns of trainers when refining/optimizing the reference patterns using machine learning techniques.

Data from observed patterns from users may be aggregated to optimize/refine the reference patterns using machine learning techniques. Data may be aggregated from sensors (e.g., the sensors 102a-102n and/or the external sensors 120a-120n), the user device 152, the remote services 154 and/or the cloud based services/data 156. Users may not be a trusted source for developing reference patterns (e.g., data from a beginner may not be useful data). A user that is not a professional athlete/trainer may often fail while attempting to perform an action.

Data from failed attempts may not be used and/or given little weight when optimizing/refining the reference patterns using machine learning techniques. Data from failed attempts may be used as reference patterns that may be recognized as a potential injury risk. For example, the observed motion data may indicate the user 70 is performing a dangerous motion pattern and feedback may be presented to warn the user 70 to stop. In another example, the observed motion data may indicate the user 70 is performing a motion pattern that may cause injury to another player/performer and feedback may be presented to warn the user 70 to stop. In some embodiments, a third party (e.g., a coach) may observe the user performing an action and determine whether or not the action was performed successfully (e.g., by entering a performance result on the user device 152).

The learning/training of the input gestures, movements and/or reference patterns may be a machine learning process. The machine learning of input gestures, movements and/or reference patterns may improve through repetition. Generally, the performance of the user 70 may be compared with the reference patterns from the trainer/coach. However, over time the user 70 may develop an individualized profile to form a basis for comparison. For example, the current movements of the user 70 may be compared to prior motion data from the same user 70.

Comparing motion data to prior motion data from the same user 70 may be useful to indicate potential long-term injuries. For example, current motion data from the user 70 may indicate the user 70 is compensating for a minor injury. The user 70 may not consider the minor injury a problem, or the user 70 may hide an injury out of fear of losing a place on a team and/or miss an important game, but over time the user 70 may develop a serious condition.

Motion patterns detected when the user 70 is fatigued and/or exhausted may appear similar to motion patterns detected when the user 70 has a minor injury. For example, the user 70 may push off with less force when a leg is injured or when the same leg is tired. Feedback may be provided indicating the user 70 appears exhausted (e.g., indicating the user 70 should stop performing and/or perform at a slower pace to prevent injury).

In some embodiments, the individualized profile of the user 70 may be used to develop more efficient reference patterns. The user 70 may optimize/improve performance of the particular task. For example, if the performance of the user 70 is efficient and/or of higher quality than other performers, the observed motion data of the user 70 may be analyzed to develop a basis for new reference patterns. Determining whether the user 70 has developed a more efficient method for performing a particular task may be determined by analyzing performance metrics.

In some embodiments, the individualized profile of the user 70 may be used to determine a deterioration of performance due to various factors. For example, factors that affect a performance level of the user 70 may comprise game schedule, weather, field conditions, equipment deterioration, injury, amount of practice, warm up time, sleep patterns, etc. Performance results (e.g., game statistics, analysis by coaches, analysis by scouts, etc.) may be correlated with the various factors. The various factors and/or performance results may be correlated with the reference patterns 202b to provide granular analysis. For example, the individualized profile of the user 70 may be used to correlate fluctuations of performance results to the various factors.

Each input gesture may be defined as a vector of features (e.g., a feature vector). The feature vector may be expressed as a time series of sensor data. The patterns in the feature vector may be classified into a finite set of gestures/movements/actions. Classification may be implemented using supervised learning and/or cluster analysis. In one example, classification of gestures may be implemented using regression methods that fit weights to the features (e.g., some data may have more influence on the classification than other data). The recording of a gesture input (e.g., a gesture instance) may be time-stamped and the set of recorded gesture instances may form part of the feature vector.

A time-stamped input recording may form a set of gesture inputs. The feature vectors of a set of gesture inputs over a time interval may form a pattern. The pattern over a time interval may be classified as an input gesture, motion, action, and/or reference pattern. Performing the input gesture many times may improve the detection accuracy through machine learning. Machine learning and classification techniques for recognizing gestures from a pattern of input data may be implemented using "The Gesture Recognition Toolkit", by Nicholas Gillian, February 2014, which is hereby incorporated by reference in its entirety.

Similarly, determining context and/or classification may be a machine learning process. The context input and/or classification data set may be larger than the input set for determining a gesture/motion. For example, context information and/or classification information may include data from the user device 152, the external sensors 120a-120n, and/or the sensors 102a-102n. The feature vectors of a set of context and/or classification inputs over a time interval may form a pattern. The pattern over a time interval may be a context and/or a classification. The detection accuracy of a context and/or classification may improve detection accuracy through machine learning.

Figure 12:
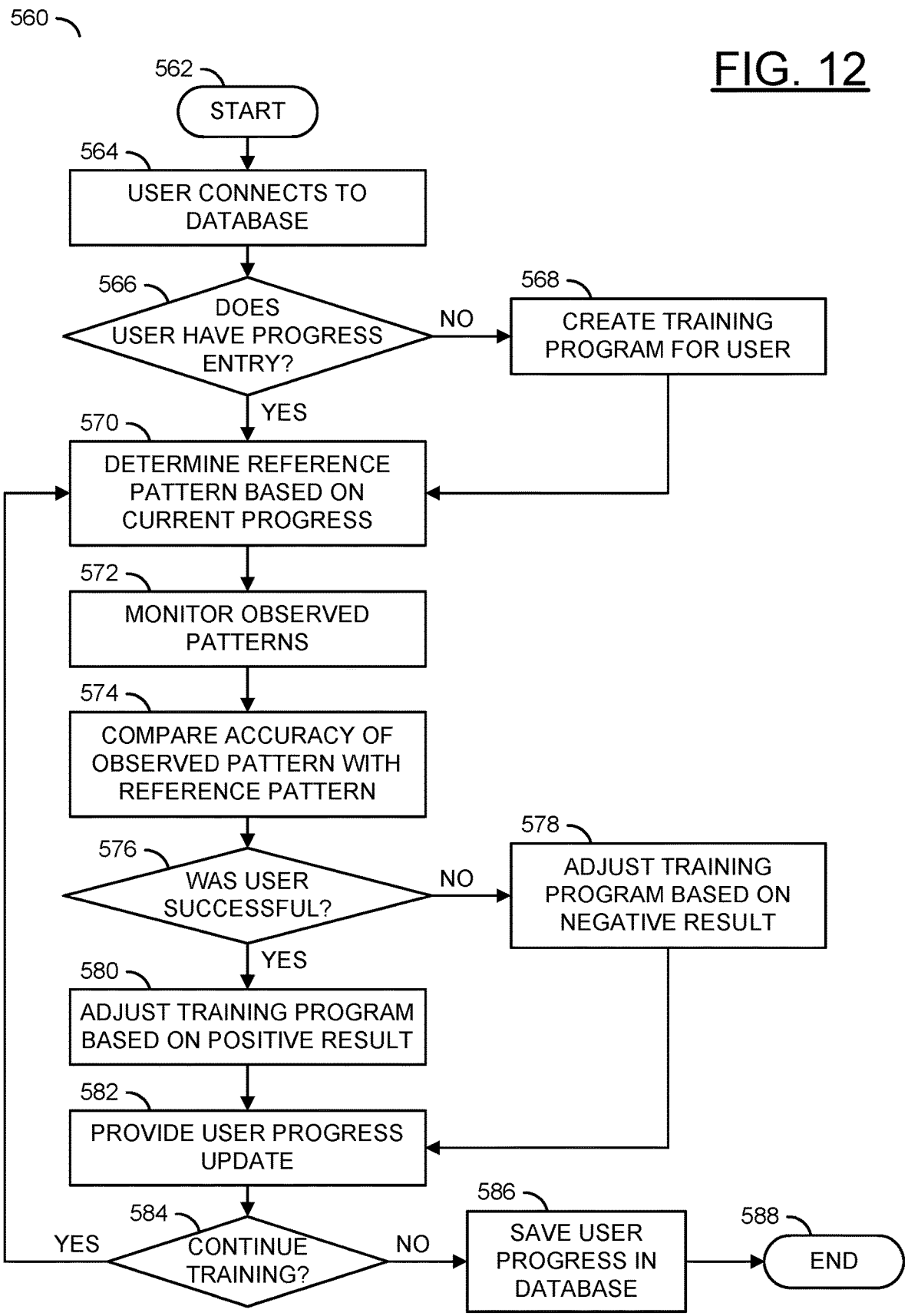
FIG. 12 is a flow diagram illustrating a method for user training and progress feedback over time.

Referring to FIG. 12, a flow diagram of a method (or process) 560 is shown. The method 560 may provide user training and progress feedback over time. The method 560 generally comprises a step (or state) 562, a step (or state) 564, a decision step (or state) 566, a step (or state) 568, a step (or state) 570, a step (or state) 572, a step (or state) 574, a decision step (or state) 576, a step (or state) 578, a step (or state) 580, a step (or state) 582, a decision step (or state) 584, a step (or state) 586, and a step (or state) 588. The state 562 may start the method 560. In the state 564, the user may connect to a database. Next, the method 560 moves to the decision state 566.

If the decision state 566 determines the user does not have a progress entry, the method 560 moves to the state 568. The state 568 may create a training program for the user. Next, the method 560 moves to the state 570. If the decision state 566 determines the user does have a progress entry, the method 560 moves to the state 570. The state 570 may determine a reference pattern based on the current progress of the user. Next, the state 572 may monitor observed patterns. The state 570 may compare the accuracy of the observed pattern with the reference patterns (e.g., using the comparison module 206). Next, the method 560 moves to the decision state 576.

If the decision state 576 determines the user was not successful, the method 560 moves to the state 578. The state 578 may adjust the training program based on the negative result (e.g., a failed performance result of the user 70 in performing the reference pattern). Next, the method moves to the state 582. If the decision state 576 determines the user was successful, the method 560 moves to the state 580. The state 580 may adjust the training program based on the positive result (e.g., a successful performance result of the user 70 in performing the reference pattern). Next, the state 582 may provide the user a progress update. Next, the decision state 584 determines whether to continue training. If so, the method 560 returns to the state 570. If not, the method moves to the state 586. The state 586 may save the user progress in the database (e.g., the cloud databases 160). Next, the method 560 moves to the state 588, which ends the method 560.

The user 70 may have an account (e.g., stored in the cloud databases 160). The account may track progress of the user 70. The user 70 may follow a training program and/or curriculum. For example, a coach/trainer may assign a training program and/or curriculum to the user 70. Data from the sensors 102a-102n, the external sensors 120a-120n, and/or the user device 152 may provide information to track progress of the user 70. In one example, the user may receive a visualization, a score, and/or a performance grade that may update over time. In another example, the coach/trainer may access the information on the tracked progress. The coach/trainer may determine which areas the user needs more practice in. The coach/trainer may also determine a safe training program based on data from the user 70. For example, the coach/trainer may see indications of an injury and determine that the training program should be at a lower intensity. In another example, the coach/trainer may determine the progress of a rehabilitation of an injured athlete.

Figure 13:
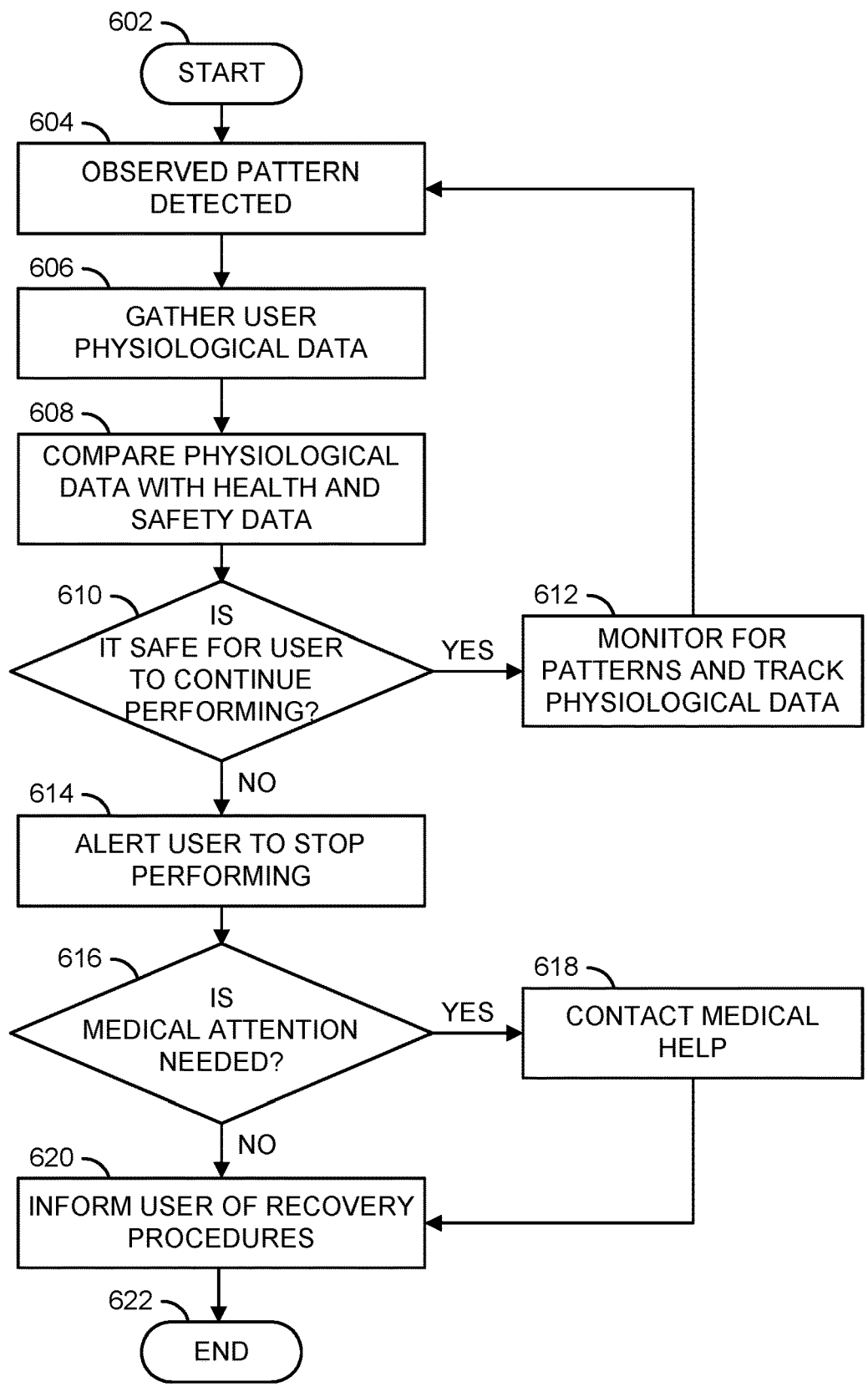
FIG. 13 is a flow diagram illustrating a method for determining user safety.

Referring to FIG. 13, a flow diagram of a method (or process) 600 is shown. The method 600 may determine user safety. The method 600 generally comprises a step (or state) 602, a step (or state) 604, a step (or state) 606, a step (or state) 608, a decision step (or state) 610, a step (or state) 612, a step (or state) 614, a decision step (or state) 616, a step (or state) 618, a step (or state) 620, and a step (or state) 622.

The state 602 may start the method 600. In the state 604, an observed pattern may be detected. Next, the state 606 may gather user physiological data. The state 608 may compare the physiological data with health and safety data. Next, the method 600 moves to the decision state 610.

If the decision state 610 determines it is safe for the user to continue performing, the method 600 moves to the state 612. The state 612 may monitor for patterns and track physiological data. Next, the method 600 returns to the state 604. If the decision state 610 determines it is not safe for the user to continue performing, the method 600 moves to the state 614. The state 614 may alert the user to stop performing. Next, the method 600 moves to the decision state 616.

If the decision state 616 determines medical attention is needed, the method 600 moves to the decision state 618. The state 618 may contact medical help. Next, the method 600 moves to the state 620. If the decision state 616 determines medical attention is not needed, the method 600 moves to the state 620. The state 620 may inform the user of recovery procedures. Next, the method 600 moves to the state 622, which ends the method 600.

The sensors 102a-102n, the external sensors 120a-120n, and/or the user device 152 may track physiological data of the user 70. Health and safety data may be acquired from the remote service 154 and/or the cloud databases 160. The health and safety data may be anonymized data relating to health statistics and/or guidelines for safety for athletes and/or performers. For example, the health and safety data may provide guidelines on how many pitches a baseball player should be limited to during a game and/or practice. The user 70 may receive a notification to stop pitching after a certain number of pitches have been thrown (e.g., based on observed patterns that indicate a pitch has been thrown).

Tracking the physiological data of the user 70 may ensure the safety of the user 70. For example, the heat may be tracked by the external sensors 120a-120n and hydration levels of the user 70 may be tracked. The user 70 may receive a notification if suffering from dehydration. The level of feedback may be based on the severity of the health situation. In one example, if a minor muscle pull is detected, a notification to stop running may be sent. The user 70 may receive a notification of a recovery procedure for a muscle pull injury (e.g., to put ice on the injury). In another example, if the user has sustained a severe injury such as a broken bone and/or a concussion medical help may be contacted.

Actions may be recorded by the wearable user input devices and compared to reference patterns to detect potential injuries. In one example, the wearable user input devices may detect the user 70 has collided with another player (e.g., based on a sudden stop in velocity). When a collision occurs, a comparison may be made to a reference pattern of a collision where a concussion was sustained. If the observed collision pattern matches the reference collision pattern of a concussion (e.g., an impact to the head and/or neck) the player may be advised to stop performing and/or seek medical help.

Figure 14:
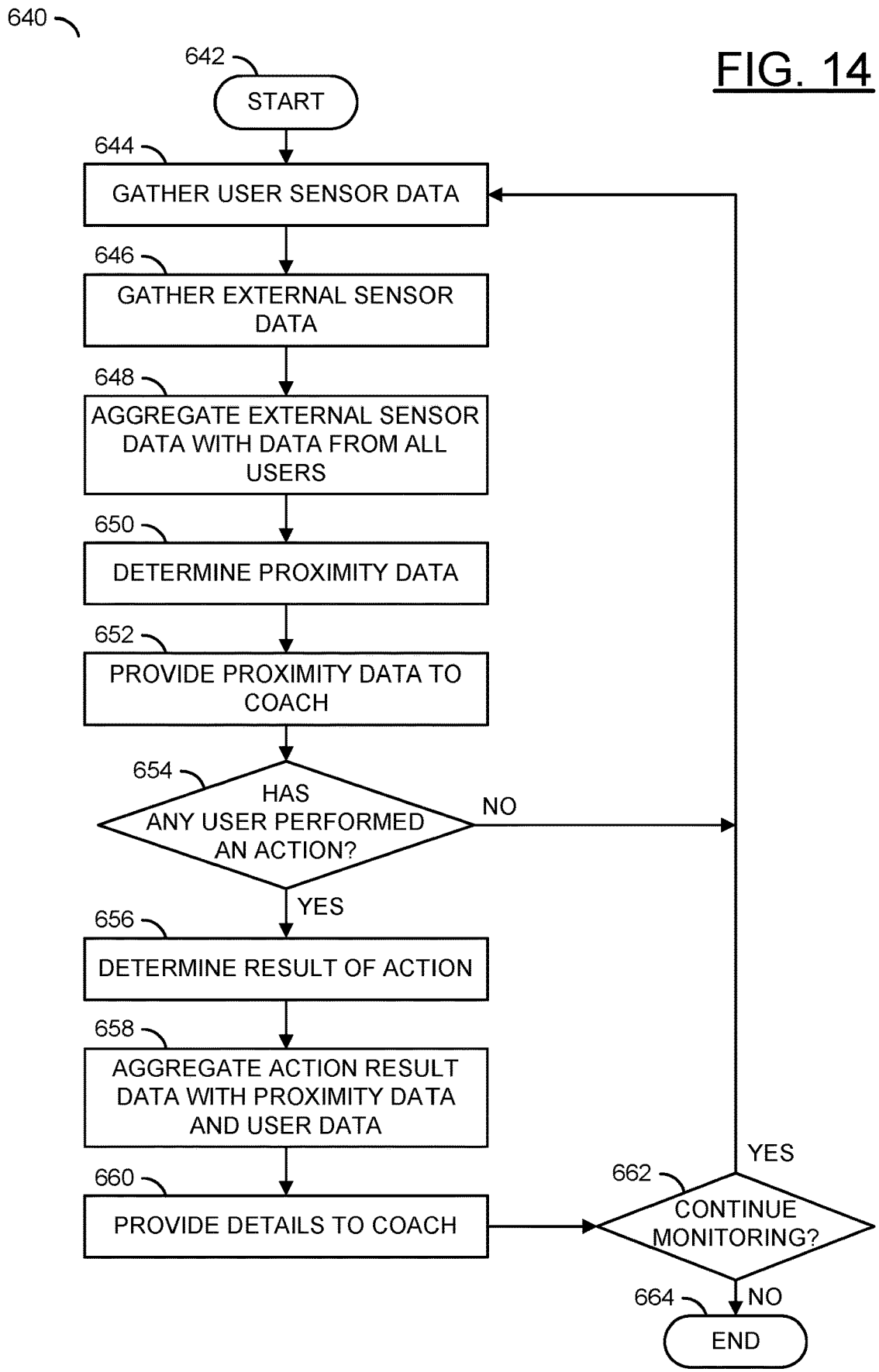
FIG. 14 is a flow diagram illustrating a method for tracking proximity data.

Referring to FIG. 14, a flow diagram of a method (or process) 640 is shown. The method 640 may track proximity data. The method 640 generally comprises a step (or state) 642, a step (or state) 644, a step (or state) 646, a step (or state) 648, a step (or state) 650, a step (or state) 652, a decision step (or state) 654, a step (or state) 656, a step (or state) 658, a step (or state) 660, a decision step (or state) 662, and a step (or state) 664.

The state 642 may start the method 640. The state 644 may gather user sensor data. Next, the state 646 may gather external sensor data. The state 648 may aggregate external sensor data with data from all users. Next, the state 650 may determine proximity data. The state 652 may provide proximity data to a coach. Next, the method 640 may move to the decision state 654.

If the decision state 654 determines that any user has performed an action, the method 640 moves to the state 656. If not, the method 640 returns to the state 644. The state 656 may determine the result of the action. Next, the state 658 may aggregate the action result data with the proximity data and the user data. The state 660 may provide details to the coach. Next, the method 640 moves to the decision state 662. If the decision state 662 determines to continue monitoring, the method 640 returns to the state 644. If not, the method 640 moves to the state 664, which ends the method 640.

The proximity data may be sent to the user device 152. The proximity data sent to the user device 152 may be sent as updates are detected. For example, the proximity data may be sent to the user device 152 of the coach. The coach may be able to see the positioning of players on the playing surface. The performance result data aggregated with the proximity data and/or user data may provide statistics (e.g., advanced statistics) for coaches and/or team managers. For example, coaches may have access to the proximity data, user data, and/or action performance result data from previous games and/or games of opponents to study instead of reviewing game tapes.

Figure 15:
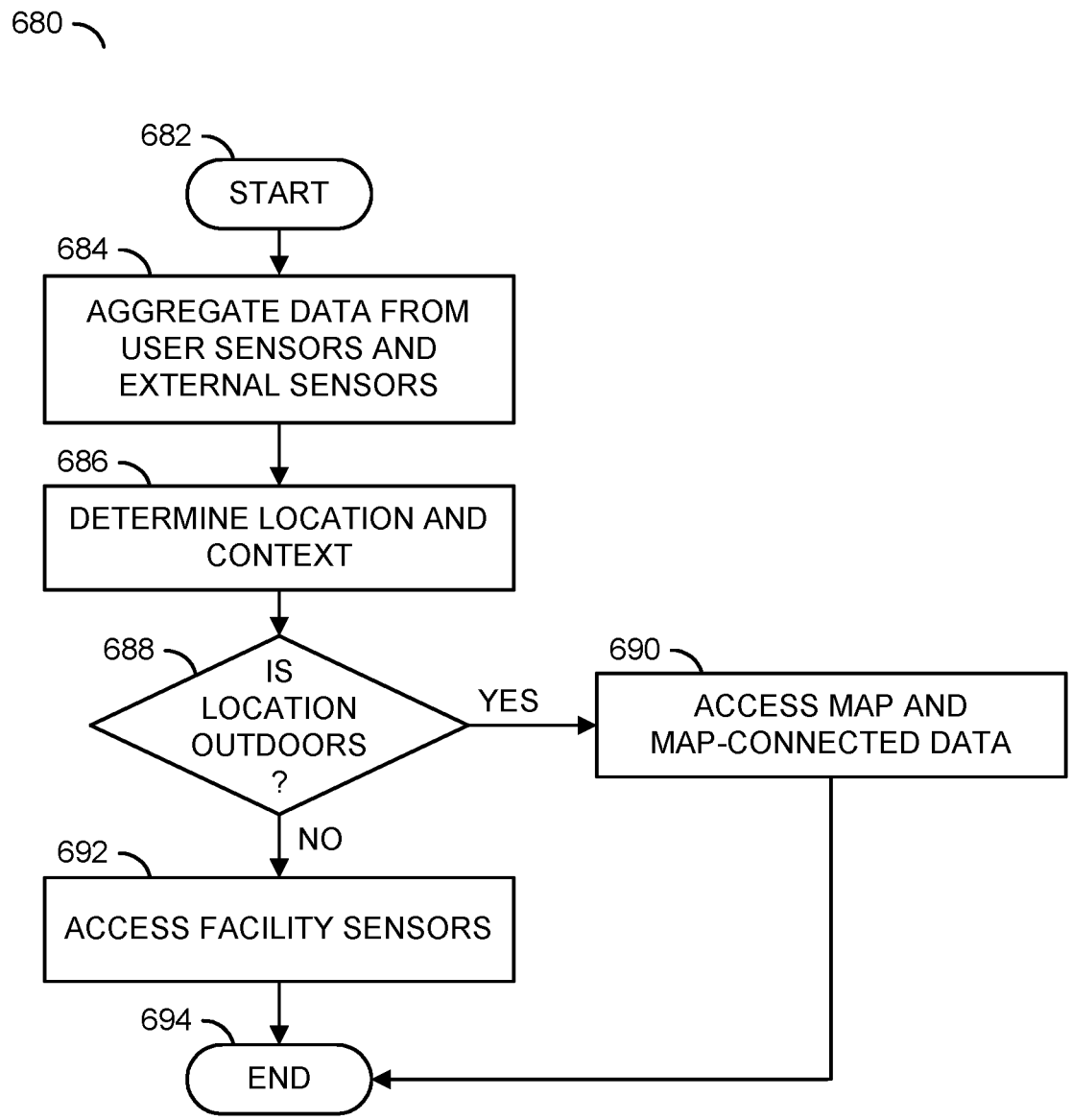
FIG. 15 is a flow diagram illustrating a method for accessing data based on location.

Referring to FIG. 15, a flow diagram of a method (or process) 680 is shown. The method 680 may access data based on location. The method 680 generally comprises a step (or state) 682, a step (or state) 684, a step (or state) 686, a decision step (or state) 688, a step (or state) 690, a step (or state) 692, and a step (or state) 694.

The state 682 may start the method 680. Next, the state 684 may aggregate data from user sensors and external sensors. The state 686 may determine location and context. Next, the method 680 moves to the decision state 688. If the decision state 688 determines the location is outdoors, the method 680 moves to the state 690. The state 690 may access map and map-connected data. Next, the method 680 moves to the state 694, which ends the method 680. If the decision state 688 determines the location is not outdoors, the method 680 moves to the state 692. The state 692 may access facility sensors. Next, the method 680 moves to the state 694, which ends the method 680.

Feedback may comprise recommendations and/or suggestions for the user 70. The feedback may be based on patterns and/or social profile features (e.g., stored in the cloud databases 160 and/or the remote service 154). For example, the feedback may suggest that people having the same personality profile of the user 70 learn faster and/or continue training/performing when provided with a particular curriculum and/or training style. Feedback may also suggest where the user 70 may fit best within a group and/or for which type of task the user 70 may be best suited. The type of feedback and/or the data used to generate the feedback may be varied according to the design criteria of a particular implementation.

The optimizing/refining process for classifications of patterns of movement, reference patterns, and/or correlations of reference patterns to experience levels may be an ongoing process. As new information is gathered, the new information is compared to previous information and/or added to sets of data. Analysis and/or interpretation of the comparisons and/or sets of data may produce classifications of movement patterns, reference patterns, and/or correlations of reference patterns to experience levels. Generally, as more information is gathered, more reliable detection, suggestions, and/or feedback may be available. The result of the optimizing/refining process may change over time as new data becomes available.

With data from many performances over time, optimal gestures and patterns of movement may be determined by correlating the observed motion data with actual performance results. Correlating the observed motion data with the actual performance results may lead to improved reference patterns. Perfect detection of motion patterns may not be needed. A combination of patterns of movement, constraints/heuristics and data from the external sensors 120a-120n may be used to classify the observed pattern. Context may be used to determine a vocabulary of tasks that may be relevant. Appropriate heuristics may be implemented to look for the relevant tasks (e.g., tasks in the vocabulary) based on the context. Reducing a number of tasks to look for may reduce a computational power needed, reduce complexity and/or reduce a potential for errors (e.g., recognizing and/or classifying an observed pattern incorrectly).

The wearable user input device 100 may receive and/or aggregate sensor input data from the sensors 102a-102n, the sensor inputs 110, and/or the external sensors 120a-120n. For example, the wearable user input device 100 may record pressure based and/or muscle movement as well as vibration and/or directional movement. The aggregated sensor input data may be used to determine potential user contexts, reference patterns, classification data, and/or proximity data. The user contexts may be used to associate a movement pattern with an appropriate classification for the given context. For example, sensor data input relating to location may determine the classification of the action performed (e.g., a kick at a football field may be a field goal attempt, while a kick at a soccer pitch may be a scoring attempt). In another example, sensor input data relating to velocity may determine a potential classification of jogging, running, skating, biking, etc.

In another example, pitch/tilt/roll sensors and/or a compass bearing sensor may determine a potential collision based on proximity data. In another example, environmental sensors (e.g., temperature sensors, barometric pressure sensors, light sensors, noise sensors, humidity sensors, weather sensors, etc.) may determine a potential context of outdoors/indoors, weather-related contexts, event participation context, etc. The environmental sensors may be used to determine the type of sport being played.

User data such as date, time of day, time of year, day of the week, and/or calendar entries may be used to determine a potential context of practice, recreational game, and/or competitive game. User data such as date, time of day, time of year, day of the week, and/or calendar entries may be used to as part of a training regimen with tracked progress. For example, a runner training for a marathon may increase distance and/or speed of practice runs as the date approaches the date of the event.

Sensor data based on location from available sensor networks may provide a context based on weather, location, traffic patterns, pedestrian patterns, transportation schedules and/or availability, event schedules, open/close times of stores/services, allergens, air quality, and/or pollution in the environment. For example, a warning may be sent to a jogger if air quality measurements indicate unsafe conditions for exercising. In another example, a warning based on information from traffic patterns may alert a bike rider to avoid a high traffic area.

Sensor data from personal sensors and/or physiological sensors (heart rate, heart rate variability, pulse, respiration patterns, blood pressure, perspiration, stress, blood glucose levels, peak respiratory flow, and/or other measurements related to medical conditions) may determine medical and/or health related data (e.g., the physiological data). The medical and/or health related data may be based on proximity in time and/or location to health sensor recordings and may enable the user to record events associated with personal health improvement programs and/or a rehabilitation regimen. The medical and/or health related contexts may be used to activate health sensor recording, activate messaging (e.g., reporting medical data to a doctor for real-time observation) and/or call for help.

The sensors 102a-102n, the external sensors 120a-120n, and/or sensors on the user device 152 may be implemented as a surface pressure sensor, body position sensor, speed sensor, vibration sensor, stride length sensor, directional bearing sensor (e.g., a GPS), available liquid levels, and/or other performance measures. For example, a vibration sensor may be an activity sensor comprised of a three-axis accelerometer often combined with a three-axis gyro and three-axis magnetometer.

The activity sensor may provide precise signals about motion, vibration, and acceleration. The activity sensor may provide information about absolute orientation, motion, and/or position. Other sensors may be implemented to collect data such as humidity, temperature, barometric pressure, rain/moisture, air quality/allergens/pollutants, proximity to vehicles, beacons and alerts, wind, solar radiation, sound/noise, proximity to people, and/or other environmental sensors. Sensors on the user may be implemented to collect physiological data such as heart rate, heart rate variability, blood pressure, skin conductance, hydration, ECG, pulse oximetry, respiration measures, blood glucose, lactic acid, activity/motion sensors, and/or other medical devices.

A wider range of actions/motions may be observed by using the wearable user input device 100 in combination with smart textiles and/or other devices. Actions/motions may be performed in close proximity to a textile with conductive elements that change an electric and/or magnetic field based on motion. The textile may provide a richer set of signals to the wearable user input device 100. The textile may be built into the performance equipment of the user 70 to ensure athletic motions are natural and/or unimpeded. In one example, some or all of the functions of the wearable user input device 100 may be embedded in the textile. In another example embodiment, the wearable user input device 100 may be made from a stretchable and/or bendable textile/material with piezoelectric properties. The piezoelectric properties of the stretchable and/or bendable textile/material may also record signals based on motion of the user 70.

The wearable user input device 100 may be self-powered through motion and/or heat harvesting by the energy harvesting component 114. In other example embodiments, the wearable user input device 100 may have a battery configured to be charged by holding the wearable user input device 100 in an electromagnetic field for a period of time. For example, the wearable user input devices/performance equipment may be stored in a sports bag and the sports bag may be stored in an electromagnetic field.

The sensors 102a-102n may be configured to detect large ranges of motion such as swinging an arm, kicking a leg, a running stride, a skating stride, etc. Larger ranges of motion may be learned by determining the tilt/pitch/roll sensor changes based on particular body movements. An aggregation of data from a plurality of wearable user input devices may be used to determine the movement of the body of the user 70. The wearable user input device 100 may be trained based on the individual capabilities, range of motion, and/or movement style of the user 70.

Accelerometers may approximate forces and impacts such as those to a football helmet. However, absolute force to a helmet may be a very rough indicator of injury. Generally, cumulative effects of many shocks/impacts are under-reported. Large impacts may be given disproportionate weight when comparing measured impacts with an actual injury.

The result of an impact/shock may be highly individualized and context dependent. To determine a result and/or measure brain health due to an impact/shock, contextual data may be taken into account in combination with data determined by the sensors 102a-102n. Learning from a richer set of context data may provide actual indicators of brain health.

The sensors 102a-102n may be multi-axis acceleration and orientation sensors. For example, the sensors 102a-102n may be a Bosch BMX0559 axis orientation sensors. Other multi-axis sensors may be used. For example, the sensors 102a-102n may be an Analog Devices MEMS iSensor having an integrated pressure sensor to measure 10 degrees of freedom. In another example, the multi-axis sensors 102a-102n may be a Freescale Xtrinsic sensor platform having 12 degrees of freedom measured in one sensor package. For example, the sensors 102a-102n may measure barometric pressure, temperature, light intensity, along with data based on 3D acceleration, 3D gyroscope, and/or 3D magnetometer information. The measurements and/or data may be combined with sensor fusion algorithms to develop an orientation output and/or other sensors being used for calibration and/or passed through to an output that includes orientation, incline, compass, gyro, accelerometer, thermometer, barometer and/or ambient light.

In yet another example, the sensors 102a-102n may be a U-BRAIN MicroSmart from the Usuda Research Institute & Systems Corporation having 15 degrees of freedom (e.g., three of the axes may be additional acceleration sensors tuned to a different range of motion). The type of multi-axis sensor implemented may be varied according to the design criteria of a particular implementation. The multi-axis sensors 102a-102n may be miniaturized and/or configured to transmit data to remote computing devices (e.g., the user device 152 and/or the external cloud computing resources 158).

Multi-axis acceleration calculation may have errors due to drift in absolute tracking. However, in a health and safety application absolute position and/or rotation may not be necessary. The wearable user input 100 may determine a pattern with respect to a context and/or constraints. Based on the pattern of motion and/or the context, damage due to an impact and/or a healing time may be determined.

The sensors 102a-102n and/or the external sensors 120a-120n may provide useful information to determine motion patterns of the user 70 and/or context information. The motion patterns and/or the context information may be used to develop rich data sets to determine a force of impact to the head of the user 70 and/or other body parts. The motion patterns and/or context information may be compared with actual patterns that have resulted in injury (e.g., the reference patterns 202b) using machine learning techniques. Based on a comparison of the observed motion patterns, the context information and/or the reference patterns 202b, personalized information related to a head impact may be developed. The user 70 may receive personalized head injury monitoring and/or management based on the observed motion patterns, the context information and/or comparisons with the reference patterns 202b.

Observed motion patterns alone may not provide sufficient information to determine whether the user 70 has sustained a head injury. For example, a large impact to the head may not lead to a concussion and the user 70 may be safe to resume performing. In another example, a small impact may result in a concussion and feedback indicating the user 70 should stop performing may be provided. For example, based on an accumulation of hits to the head the generated feedback may indicate the user 70 should stop performing. Observed motion patterns compared with the reference patterns 202b and the context information may provide sufficient information to generate useful feedback for the user 70.

To learn the personalized impact of shocks/impacts to the head, contextual data may be observed. The context data may be comprised of performance data from the rest of play. For example, recent history of the performance of the user 70 (e.g., a reduction in reaction time and/or decreased balance may indicate the user 70 has sustained a concussion). The context data may be comprised of other performance and/or cognitive data sources outside of a performance. For example, baseline cognitive testing, school grades, attention data, performance data from online learning management systems used in schools, data from health records, patterns of behavior change, and/or patterns of data found in social media sources, including measures of attitude and attention.

Based on data from the reference patterns 202b and/or actual injury results, specific plays and/or scenarios during a performance may be tagged as being dangerous and/or unsafe (e.g., likely to lead to a head injury, having a higher incidence of injury, etc.). Coaches may teach players that particular plays and/or scenarios are more injurious than others (e.g., an unsafe scenario). For example, coaches may teach young players to not make contact with a vulnerable player (e.g., not hit a player into the boards from behind in hockey). Coaches may be given data to indicate certain players are more prone to getting injured in certain plays. Generally, coaches may teach players to avoid unsafe scenarios based on the aggregated proximity data. For example, a coach may limit the number of pitches a player known to have a shoulder injury may throw. In another example, the coach may limit a recovering player to non-contact practice and/or performing alone. The result may be a more accurate representation of injury data, better decisions by coaches and/or players as to when to play and in which position to play.

Figure 16:
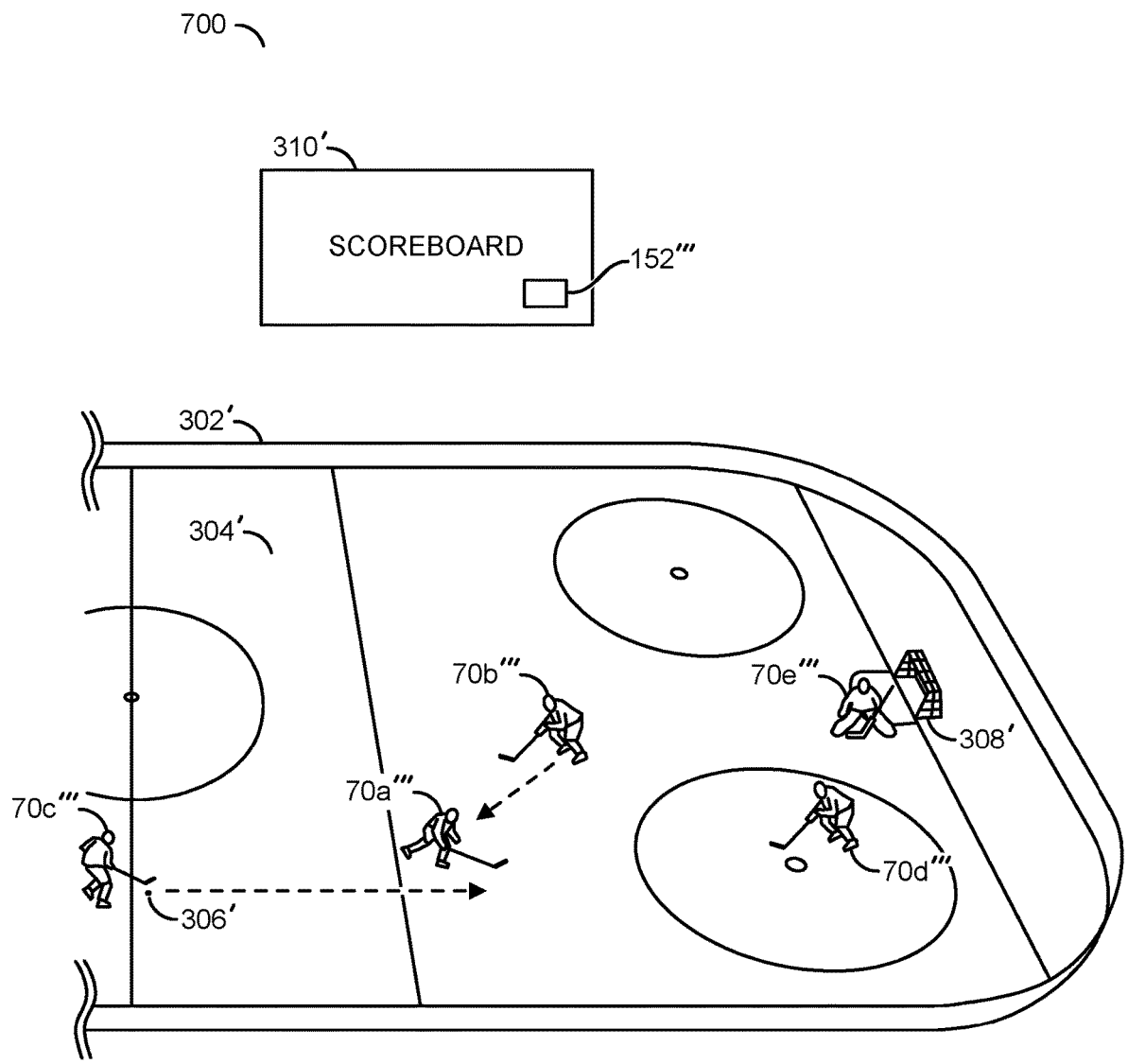
FIG. 16 is a diagram illustrating an example of sensor data recognizing an unsafe scenario.

Referring to FIG. 16, an example of sensor data recognizing an unsafe scenario 700 is shown. The example unsafe scenario 700 may be a representation of a so-called "suicide pass" in hockey. The example unsafe scenario 700 may comprise players 70a'''-70e''', a user device 152''', a boundary (e.g., boards) 302', a playing surface (e.g., ice) 304', an object of contention (e.g., puck) 306', a goal 308', and a facility fixture (e.g., a scoreboard) 310'. The example unsafe scenario 700 may be configured similarly to the example team indoor sport embodiment 350 (e.g., described association with FIG. 7).

The player 70c''' is shown passing the puck 306' to the player 70a'''. The player 70a''' is shown looking backwards to receive the puck 306' while skating forwards up the playing surface 304'. Since the player 70a''' is looking backwards, the player 70a''' may be unaware of the player (e.g., an opposing player) 70b'''. The player 70b''' may be anticipating the player 70a''' receiving the puck 306' and initiating contact. Generally, the player 70b''' making contact with the player 70a''' is permitted (e.g., part of the rules of play) and may not lead to injury. However, since the player 70a''' is looking behind and unaware of the player 70b''', the player 70a''' may be in a vulnerable position. If the player 70b''' makes contact with the player 70a''' while the player 70*a*''' is unaware of the player 70*b*''' (e.g., a blind side hit), a likelihood of the player 70*a*''' sustaining a head injury may increase.

Proximity data from the players 70*a*'''-70*e*''' and/or the external sensors 120*a*-120*n* (e.g., external sensors arranged along the boards 302' and/or the playing surface 304') may be used to detect an observed scenario. For example, the proximity data may indicate the player 70*b*''' may be about to collide with the player 70*a*'''. The observed motion patterns of the player 70*a*''' may indicate the player 70*a*''' may not be aware of the player 70*b*''' (e.g., based on rotation information from the head and/or neck of the player 70*a*'''). The observed scenario may be compared to the reference patterns 202*b* (e.g., based on previously stored proximity data and/or actual injury data). The observed scenario may be determined to be the unsafe scenario 700.

Feedback may be generated by the user device 152''' when the unsafe scenario 700 is detected. For example, the user device 152''' may communicate to the sensors 102*a*-102*n* in the wearable user input devices worn by the players 70*a*'''-70*e*'''. The sensors 102*a*-102*n* may generate feedback (e.g., haptic feedback). For example, the player 70*c*''' may receive feedback as a warning not to pass the puck 306' to the player 70*a*'''. In another example, the player 70*a*''' may receive feedback as a warning of an approaching opponent. In yet another example, the player 70*b*''' may receive feedback as a warning that the player 70*a*''' may be in a vulnerable position. Based on the feedback the players 70*a*'''-70*e*''' may have a chance to avoid the unsafe scenario 700 and/or make adjustments to reduce a severity of a potential injury. The feedback generated by analyzing the proximity data may be used to prevent head injuries.

The proximity data may be used to determine a play being dangerous and/or a player being in a vulnerable position. For example, the external sensors 120*a*-120*n* may be implemented as a camera network to localize the players 70*a*'''-70*e*'''. Context may be used to determine proximity and/or provide feedback (e.g., whether a player is in practice, a competitive game, a scrimmage game, etc.) In some embodiments, the players 70*a*'''-70*e*''' may be wearing a wearable user input device comprising a heads-up display. For example, a visor of a wearable user input helmet may comprise a display output. The display output may present a message and/or notification (e.g., feedback) to the player. For example, a notification may be displayed warning one player that another player is in a vulnerable position.

Coaches, referees/officials and/or player safety representatives may use the proximity data to determine potentially unsafe scenarios. The proximity data may indicate particular scenarios are unsafe. For example, an unsafe scenario may be a scenario (e.g., a play) where there is a higher incidence of injury. The proximity data may be used as context information. For example, if the observed motion data of the player 70*a*''' indicates a head impact has occurred, the proximity data may be used to determine a severity of the injury (e.g., based on a velocity of the player 70*b*''' and/or other actual injuries detected in similar observed scenarios).

In some embodiments, coaches and/or parents may teach young players to avoid scenarios known to be unsafe (e.g., teach the player 70*a*''' to look for opposing players while receiving a pass, teach the player 70*b*''' to limit a force of a collision with the player 70*a*''', etc.). In some embodiments, referees/officials may call penalties/fouls and/or stop play when an unsafe scenario is detected. For example, rule violations and/or fouls may be identified even when the referee/official does not otherwise detect the violation. In some embodiments, player safety representatives and/or league officials may apply punishments (e.g., suspensions) to players to deter unsafe scenarios. In some embodiments, medical personnel may be notified when an unsafe scenario occurs (e.g., to improve response time).

Preventing head injuries may be an optimal solution. However, contact in sports may be unavoidable and/or part of the game. Identifying head injuries, the severity of the injury and/or a recovery time of an injured player may reduce long-term risk to athletes and/or performers. For example, players may collapse during and/or shortly after a performance due to a head injury. In another example, players may suffer long-term health effects due to continuous/repeated impacts (e.g., many impacts to the head over a longer period of time). Identifying head injury due to a large impact and/or accumulated impacts may be important.

Head injuries may have a number of important considerations and/or factors. A factor of a head injury may consist of brain trauma due to rotational forces (e.g., non-focal injuries). A factor of a head injury may consist of a risk of neck injury (e.g., whiplash). A factor of a head injury may be long-term risk (e.g., a cumulative effect of many impacts). The cumulative effect from many impacts may include minor and/or small impacts that do not cause any apparent damage.

Brain trauma due to rotational forces may be a significant factor in determining a severity of a head injury. Generally, modern helmets (e.g., football helmets, hockey helmets, boxing helmets, etc.) do very little to reduce rotational forces. The brain may be very sensitive to rotational blows.

Measuring head impacts may not be sufficient to determine a risk of neck injury. Trauma to the neck may be a function of posture. A biomechanical model may be developed for the neck and/or force estimates may be calculated at the head and neck base. The biomechanical model may be configured to generate a set of signals reflecting the risk of neck trauma.

To determine long-term risk, a model may be developed to determine the cumulative effect of impacts. For example, the player may only be exposed to no more than a particular amount of cumulative damage over a given time period T. Micro-traumas may be measured to determine the cumulative impacts.

Figure 17:
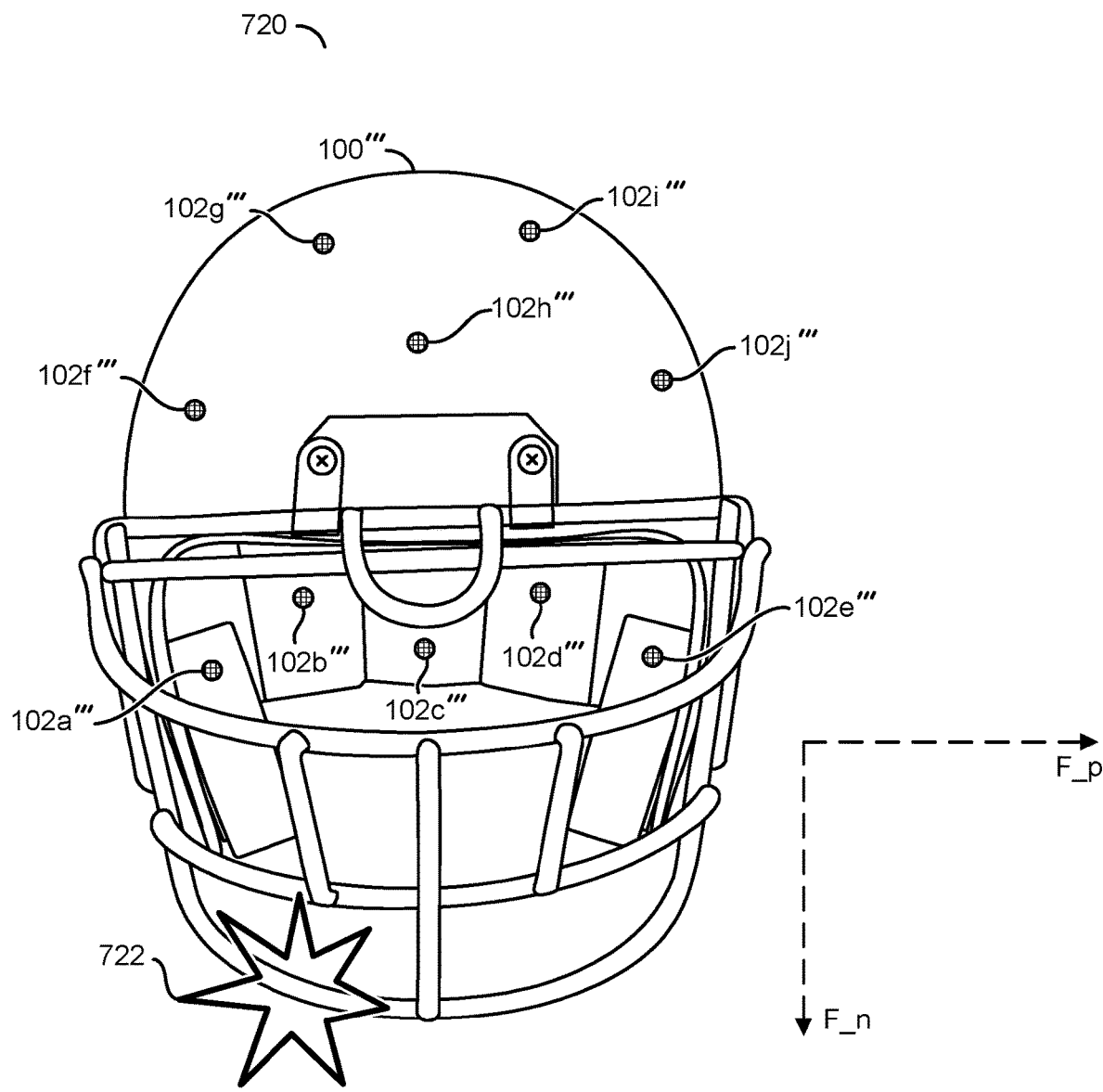
FIG. 17 is a diagram illustrating an example embodiment of a wearable user input helmet.

Referring to FIG. 17, an example embodiment 720 of a wearable user input helmet 100''' is shown. The wearable user input helmet 100''' may comprise the sensors 102*a*'''-102*j*'''. The wearable user input helmet 100''' is shown receiving an impact 722. The wearable user input helmet 100''' may be configured to measure direct and/or rotational impact force. The wearable user input helmet 100''' may be implemented as a football helmet, a hockey helmet, a baseball helmet, a boxing helmet, a military (e.g., combat) helmet, a hard hat, etc.

The applied force/impact 722 may have two components. One component of the applied force/impact 722 (e.g., F_n) may be normal to a surface receiving the force/impact 722. Another component of the applied force/impact 722 (e.g., F_p) may be parallel to the surface receiving the force/impact 722. The perpendicular component (e.g., F_n) of the applied force/impact 722 may not cause rotational motion. The parallel component (e.g., F_p) may cause rotational motion. The parallel component F_p may further cause shear forces in the wearable user input helmet 100'''. Shear forces in the wearable user input helmet 100''' may propagate as stress throughout the wearable user input helmet 100'''.

The sensors 102*a*'''-102*j*''' may be embedded in the surface of the wearable user input helmet 100'''. In some embodiments, the embedded sensors 102*a*'''-102*j*''' may be set of strain gages. For example, the strain gages 102a'''-102j''' may be three-element rosette gages. Each of the three-element rosette gages 102a'''-102j''' may comprise three separate gages arranged in three different directions (e.g., each of the gages may measure a minimum and/or normal stresses at each point).

The sensors 102a'''-102j''' may cover the surface of the wearable user input helmet 100'''. At each location of the sensors 102a'''-102j''' measurements may be performed. The stresses at the location of each of the sensors 102a'''-102j''' may be recovered. If the force/impact 722 having an unknown force and/or an unknown direction is applied to the wearable user input helmet 100''', the force and/or direction may be estimated based on data from the sensors 102a'''-102j'''.

Based on the estimated force and/or direction, the parallel force F_p of the impact/force 722 may be determined. For example, the strain gages 102a'''-102j''' may be used to estimate the parallel force F_p. The parallel force F_p may be used to determine and/or assess rotational acceleration injuries. In some embodiments, the normal force F_n and/or the parallel force F_p of the impact/force 722 may be determined. For example, data from the sensors 102a'''-102j''' may be used to determine shear forces propagating as stress throughout the wearable user input helmet 100'''. The normal force F_n and/or the parallel force F_p may be estimated based on comparisons of the observed patterns of motion (e.g., data from the sensors 102a'''-102j''') with the reference patterns 202b. In some embodiments, a propagation model using a neural network may be implemented. The neural network may be implemented using the user device 152, the remote service 154 and/or the external cloud computing resources 158. The input to the neural network may be the three strains measured at each location of the strain sensors 102a'''-102j''' (e.g., the input may be a 3N vector, where N represents the number of strain sensors embedded in the wearable user input helmet 100'''). The reference patterns 202b may be determined using controlled experiments.

Shear forces propagating as stress throughout the wearable user input helmet 100''' may be used to determine wear/degradation of the wearable user input helmet 100'''. Generally, as time passes protective equipment may need replacement to ensure sufficient protection for the user 70. For example, bicycle helmets should be replaced after the helmet hits the ground. Similarly, protective sporting equipment should be replaced after sustaining a particular amount of damage (e.g., a damage threshold). In some embodiments, data from the sensors 102a'''-102j''' may be used to determine when to replace the wearable user input helmet 100''' (e.g., when the helmet 100''' no longer provides sufficient protection) and feedback may be generated (e.g., a notification sent to the user device 152) to indicate to the user 70 that the wearable user input helmet 100''' may no longer provide sufficient protection.

Shear forces may be measured in other types of performance equipment (e.g., shin pads, protective gloves, elbow pads, protective girdles, cups, shoulder pads, chest protectors, protective pants, etc.). Similar wear/damage detection and/or notifications may be provided for each type of performance equipment. The type of performance equipment, and/or the damage threshold used to determine a level of degradation may be varied according to the design criteria of a particular implementation.

In some embodiments, the sensors 102a'''-102j''' may be inertial sensors. For example, the inertial sensors 102a'''-102j''' may be embedded in the wearable user input helmet 100'''. Rotational acceleration of the head due to the impact/force 722 may be measured and/or estimated using data from the inertial sensors 102a'''-102j'''. Generally, inertial sensors may not determine wear/damage to the performance equipment in the same fashion as sensors that directly measure strain.

In some embodiments, the sensors 102a'''-102j''' may be a combination of inertial sensors and/or strain sensors. The number and/or type of the sensors 102a'''-102j''' in the wearable user input helmet 100''' may be varied according to the design criteria of a particular implementation. A combination of inertial and/or strain sensors may be configured to estimate the forces at a mechanical interface between a head and neck of the user 70 (e.g., a head-neck interface). The forces at the head-neck interface of the user 70 may be estimated by modeling a free body diagram of the head of the user 70, along with the perpendicular force F_p and the normal force F_n of the impact 722 at the head-neck interface.

Determining a sum of forces and sum of torques may yield accelerations and rotations measured by the inertial sensors 102a'''-102j'''. Using inverse dynamics, the forces at the head-neck interface may be estimated. To determine and/or estimate accelerations due to the impact/force 722 a mass and/or moment of inertia of the head of the user 70 may be needed. For example, the mass of the head of the user 70 may be estimated based on anthropometric studies and/or size of the wearable user input helmet 100'''. In another example, a model of the body of the user 70 may be developed based on context information (e.g., medical information, self-reported information, etc.). The source of the data may be varied according to the design criteria of a particular implementation.

Figure 18:
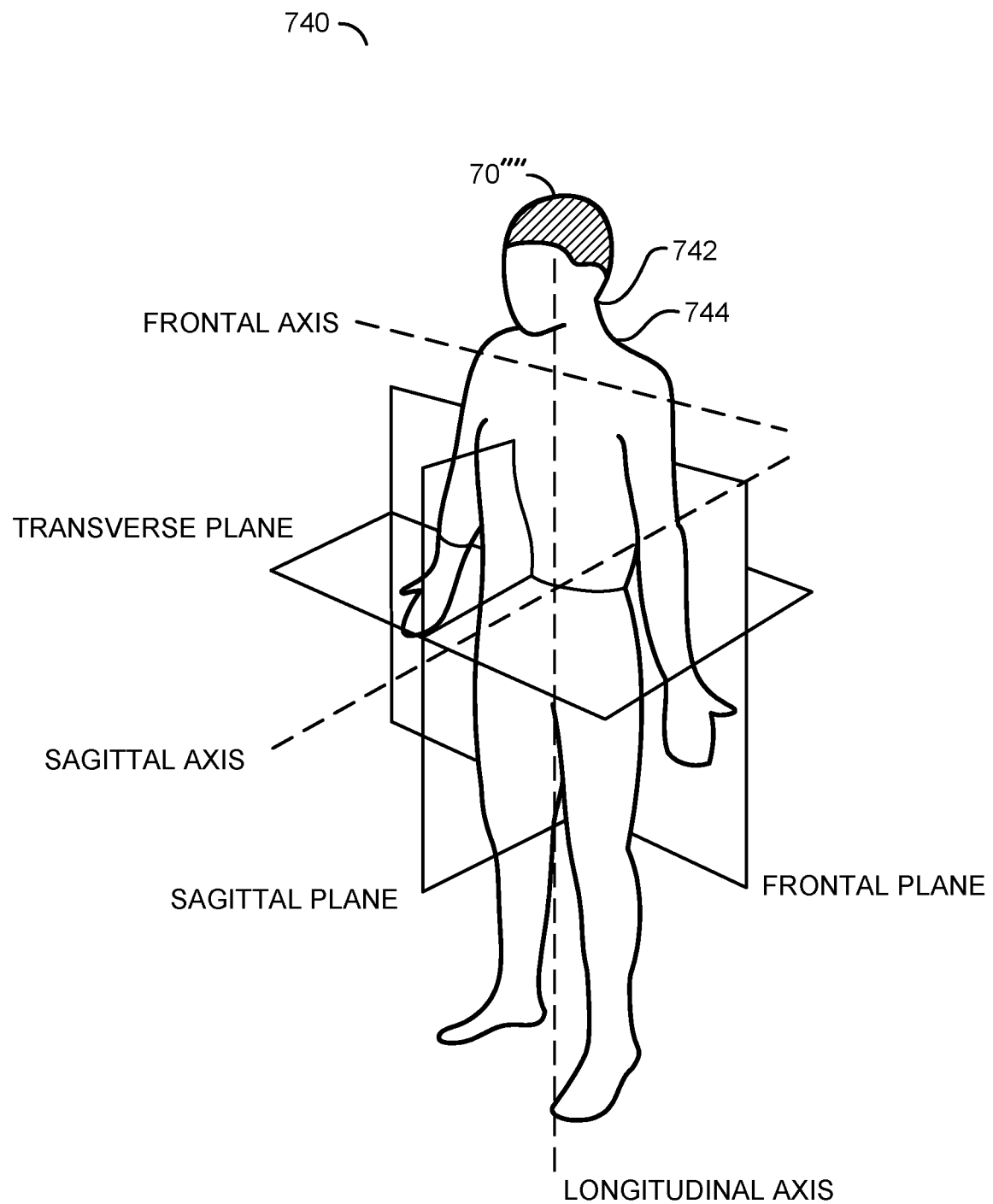
FIG. 18 is a diagram illustrating axes of an example body model.

Referring to FIG. 18, axes of an example body model 740 of a user 70'''' are shown. The example body model 740 indicates various axes and planes of the body of the user 70''''. A frontal axis, a sagittal axis and a longitudinal axis of the body of the user 70'''' are shown. A frontal plane (e.g., a coronal plane), a traverse plane and a sagittal plane of the body of the user 70'''' are shown. A head-neck interface 742 and a neck-body interface 744 of the body of the user 70'''' are shown.

Current research on head injuries has determined that quick rotations of the head of the user 70'''' about the sagittal axis may be the most dangerous. Rotations about the frontal axis may be less dangerous (but still dangerous). For example, a 'nodding' motion (e.g., rotation about the frontal axis) may be the least dangerous. In another example, a 'left-right shake' motion (e.g., rotation about the longitudinal axis) may be more dangerous. In yet another example, a 'side-to-side bobble' (e.g., rotation about the sagittal axis) may be the most dangerous. Generally, rotations about various axes have different contributions to head injuries caused by an impact (e.g., the impact 722). To account for the differing contributions, various weights (or scale factors) may be associated with rotations about each type of rotation.

Weights (or scale factors) associated with each type of rotation and/or force may be varied and/or trained over time. More information may be learned from the received data and/or context information. For example, the context information may be updated/refined as more medical research information becomes available (e.g., and passes peer review). Based on the refined context data, the weights associated with each type of rotation and/or force may be updated and/or refined.

For example, there may be some type of damage (e.g., currently unknown) from particular rotations and/or forces that has not yet been recognized. In another example, some rotations and/or forces may be more prevalent and/or damaging in some sports over others due to types of motions performed, collisions that occur and/or types of protective gear available. In some embodiments, the weighting may be determined based on biomechanical studies. In other embodiments, weighting may be inferred from past injury data from several subjects. Data may be continually updated and/or refined. The amount of weighting and/or the associations of the weighting may be varied according to the design criteria of a particular implementation.

To determine a risk of a head injury, a weight (or scale factor) may be given to a value associated with the observed motion patterns (e.g., the rotations of the head of the user 70""). The weight may be a scalar value based on a level of importance and/or a contribution of a type of movement to a potential head injury. For example, a greater weight may be associated with patterns of movement indicating a rotation about the longitudinal axis. In another example, a lesser weight may be associated with patterns of movement indicating a rotation about the frontal axis.

In some embodiments, components of the estimated parallel force $F\_p$ of the impact 722 may be weighted according to torques about the sagittal, frontal and/or longitudinal axis of the head of the user 70"". In some embodiments, the perpendicular force $F\_n$ may also contribute to the torques (e.g., when the force $F\_n$ is not directed towards the center of rotation). Based on the comparison of the observed motion patterns (e.g., used to determine the estimated force of the impact 722) and the reference patterns 202b a risk signal may be generated (e.g., feedback representing a risk of diffuse and/or directional axonal injury).

Figure 19:
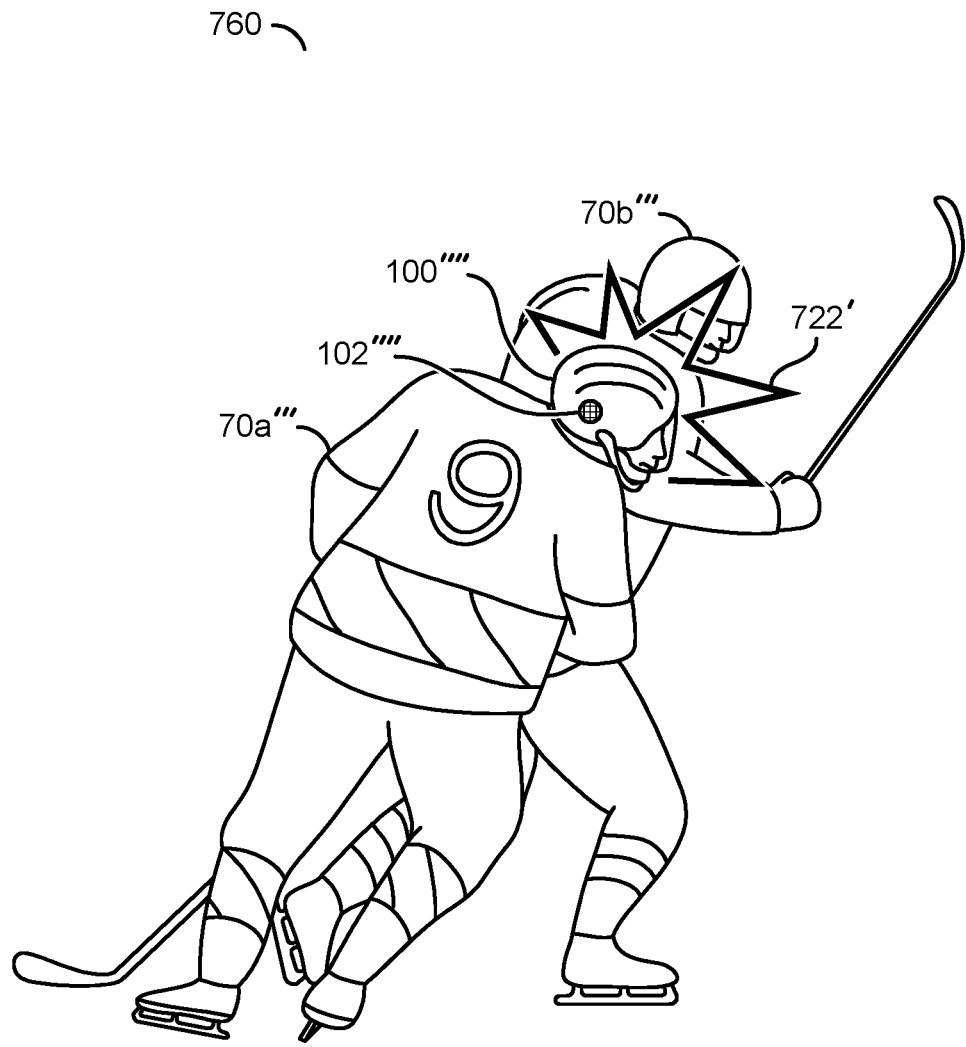
FIG. 19 is a diagram illustrating an example of a head trauma with rotational force.

Referring to FIG. 19, an example of a head trauma with rotational force 760 is shown. The user 70a''' is shown receiving an impact 722' from the user 70b'''. For example, the impact 722' may be a result of the unsafe scenario 700 described in association with FIG. 16.

The user 70a''' is shown wearing the wearable user input device 100"". The wearable user input device 100"" is shown having a sensor 102"". While only the sensor 102"" is shown, the wearable user input device 100"" may comprise more sensors (e.g., as described in association with FIG. 17). The user 70a''' may be wearing other wearable user input devices. For example, the skates, stick, pants, jersey, and/or other protective gear may be other types of wearable user input devices. The player 70b''' may also be wearing one or more wearable user input devices (e.g., used to determine proximity data). The number of sensors and/or the number/type of wearable user input devices worn may be varied according to the design criteria of a particular implementation.

The user 70b''' may be making contact to the head of the user 70a'''. For example, the head of the user 70a''' may be the principle point of impact of the impact/force 722'. The head of the user 70a''' is shown rotating due to the impact 722'. The body of the user 70a''' is shown facing one direction, while the head of the user 70a''' is shown facing another direction due to the impact 722'. The head trauma with rotational force 760 may likely result in a head injury (e.g., a concussion).

Generally, padding in conventional helmets may provide little protection and/or do very little to mitigate effects of rotational blows as shown in the example head trauma 760. Rotational forces and/or rapid acceleration/deceleration may result in lesions to the brain. The lesions may be a result of a diffuse and/or directional axonal injury (DAI). In one embodiment, a risk for DAI may be estimated as being proportional to a magnitude of the net torque due to the computed force of the impact 722'. In another embodiment, the system may produce three separate signals for DAI risk based on each net torque component (e.g., about the sagittal, frontal and longitudinal axis).

Impacts to the head (e.g., the impact 722') may be determined when the wearable user input device 100 is a helmet (e.g., the helmet 100""). However, the user 70 may still sustain head trauma in sports and/or activities where the participants do not wear helmets. The multi-axis sensors 102a-102n in combination with other data sources (e.g., the external sensors 120a-120n) may be trained to identify patterns of movement that correlate to head impact even if the wearable user input device 100 is worn on other parts of the body. For example, the wearable user input device 100 may be wrist-worn, clothing-embedded, and/or a body patch-worn sensor fusion system. Multiple wearable user input devices (e.g., the wearable user input devices 100a-100e) may be used to identify impact patterns based on movements of other body parts that correspond to a head injury.

Figure 20:
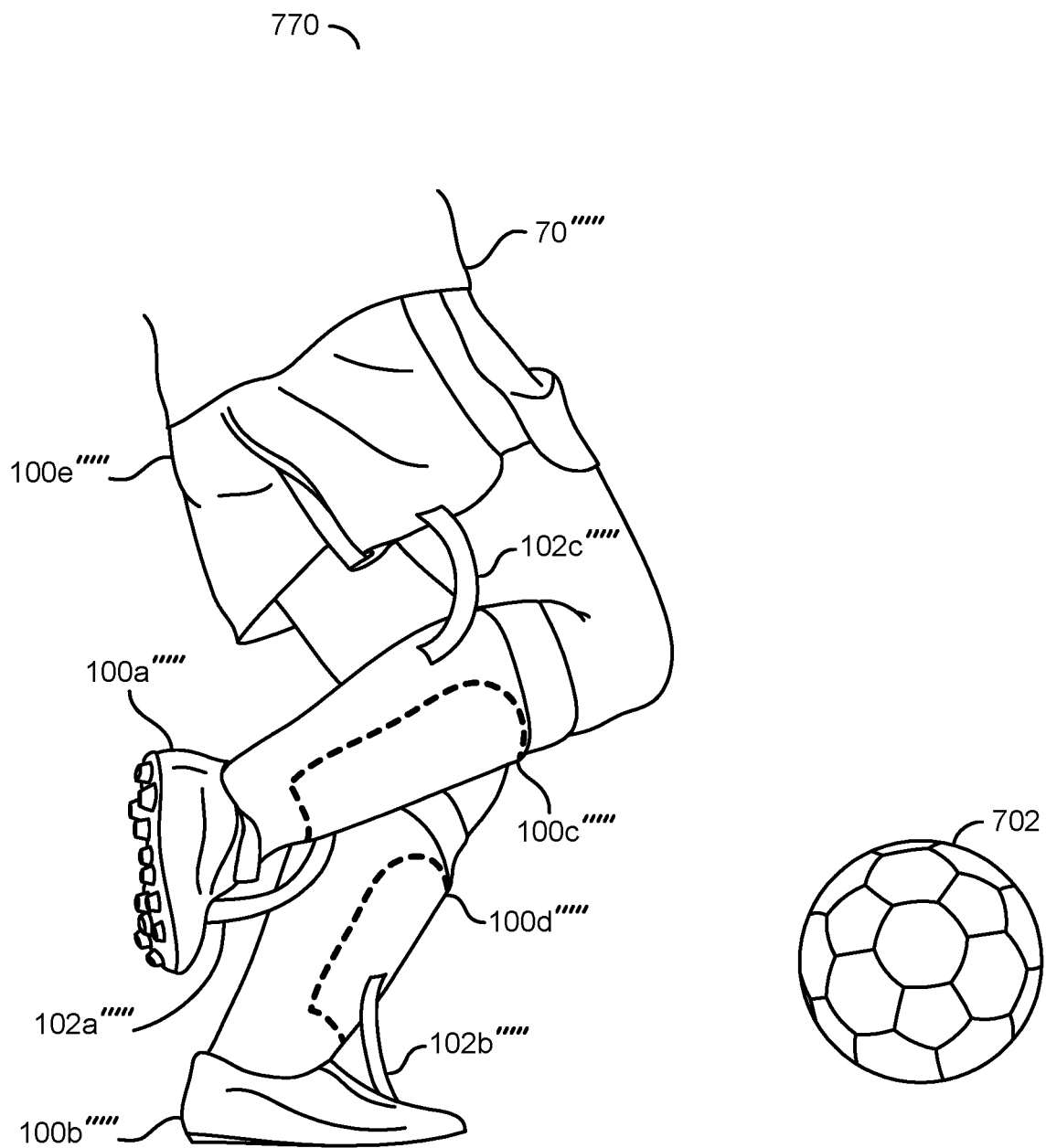
FIG. 20 is a diagram illustrating an example embodiment of sensors measuring joint angles.

Referring to FIG. 20, an example embodiment of sensors measuring joint angles 770 is shown. The user 70"" is shown playing soccer (e.g., kicking the ball 702). The user 70"" is shown wearing various types of wearable user input devices 100a''''-100e''''. Generally, soccer players do not wear helmets. The user 70"" may be wearing soccer cleats 100a''''-100b'''', shin guards 100c''''-100d'''' and/or shorts 100e''''. Each of the wearable user input devices 100a''''-100e'''' may have corresponding sensors (e.g., inertial sensors and/or strain gages as described above).

Sensors 102a''''-102c'''' are shown attaching between various joints of the user 70"". The sensors 102a''''-102c'''' may be configured to measure joint angles of the user 70"". In one example, the sensor 102a'''' may be attached between the right soccer cleat 100a'''' and the right shin guard 100c'''' and measure the joint angle of the right ankle of the user 70"". In another example, the sensor 102b'''' may be attached between the left soccer cleat 100b'''' and the left shin guard 100d'''' and measure the joint angle of the left ankle of the user 70"". In yet another example, the sensor 102c'''' may be attached between the right shin guard 100c'''' and the shorts 100e'''' and measure the joint angle of the knee of the user 70"". The number of sensors worn and/or the joints measured may be varied according to the design criteria of a particular implementation.

The sensors 102a''''-102c'''' may be inertial sensors. The sensors 102a''''-102c'''' may be a fiber optic flexible angular displacement sensor. For example, the sensors 102a''''-102c'''' may be a combination of inertial sensors, strain gages and/or flexible angular displacement sensors. The combination and/or type of sensors may be varied according to the design criteria of a particular implementation.

The angular displacement sensors 102a''''-102c'''' may be configured to measure and/or estimate joint-angles. The joint-angle estimate may not need to be an accurate measurement. For example, the angular displacement sensors 102a''''-102c'''' may be configured as a zero-crossing signal (e.g., indicate when a measured angle is zero).

A zero-crossing signal may be implemented to reset a relative position of two inertial sensors embedded in different links (e.g., the right clear 100a'''' and the right shin guard 100c'''') sharing a joint (e.g., the ankle of the user 70""). Resetting the relative position of two inertial sensors sharing a joint may be used to control and/or mitigate effects of drift of tracked data by the various sensors of the wearable user input devices 100a''''-100e''''.

Developing a model of the user 70''''' using inertial sensors and/or angular displacement strips (e.g., the sensors 102a'''''-100c''''') may provide a system that yields joint angles, link velocities and/or accelerations. In some embodiments, the user 70''''' may wear force sensors embedded in the shoes (e.g., the soccer cleats 100a'''''-100b''''') configured to measure the ground reaction forces.

The model of the user 70''''' based on data from ground reaction forces, joint angle measurements, link velocities and/or accelerations may provide forces at each link (e.g., joint of the user 70'''''). In some embodiments, the system may iteratively compute the forces at each link by working upward from the feet and ankles. The system may calculate the forces at the neck-body interface 744. For example, the computations may be performed by the user device 152, the remote service 154 and/or the external cloud computing resources 158.

Figure 21:
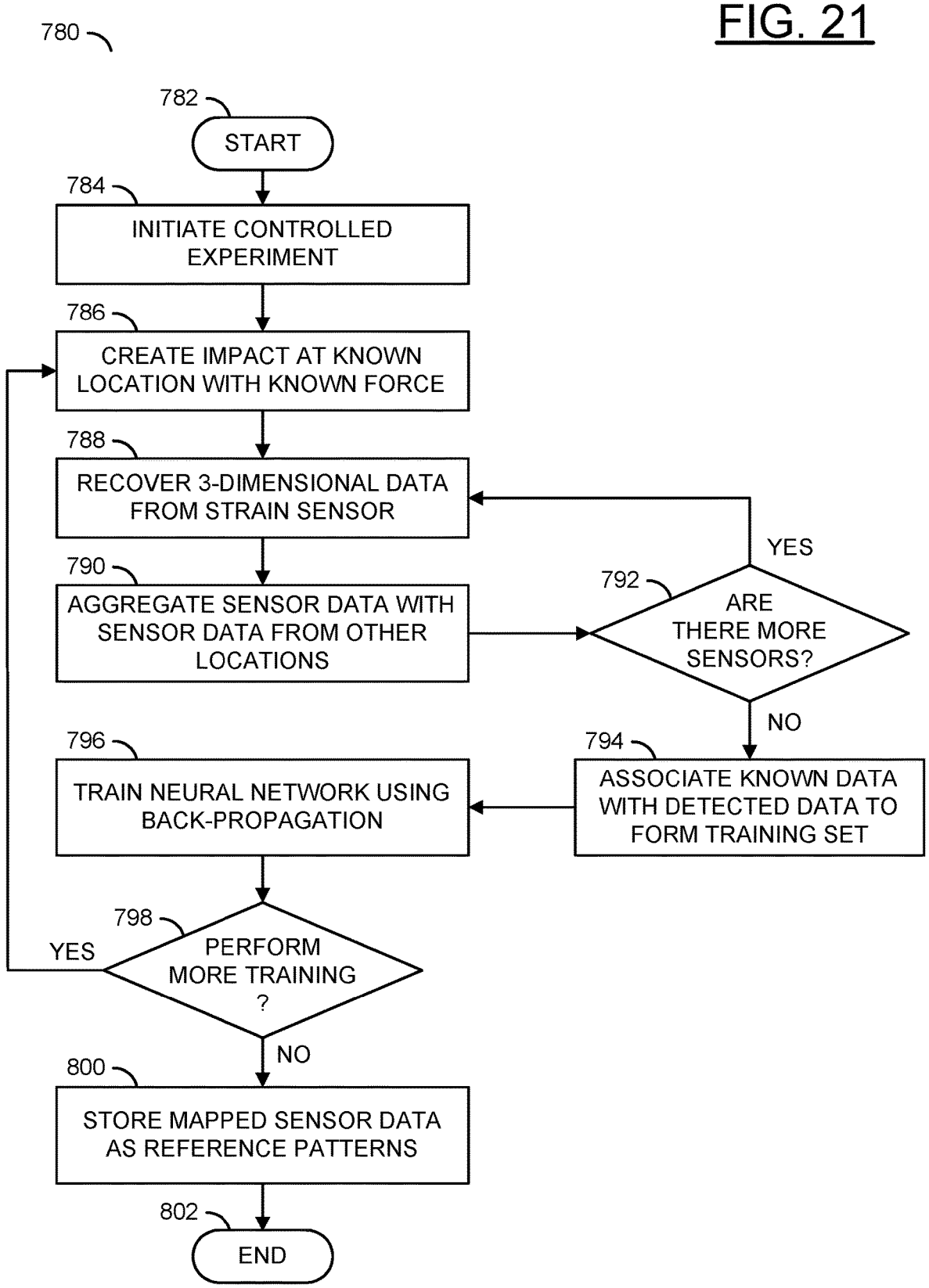
FIG. 21 is a flow diagram illustrating a method for training a neural network to develop references patterns for detecting forces.

Referring to FIG. 21, a flow diagram of a method (or process) 780 is shown. The method 780 may train a neural network to develop references patterns for detecting forces. The method 780 generally comprises a step (or state) 782, a step (or state) 784, a step (or state) 786, a step (or state) 788, a step (or state) 790, a decision step (or state) 792, a step (or state) 794, a step (or state) 796, a decision step (or state) 798, a step (or state) 800, and a step (or state) 802.

The state 784 may start the method 780. The state 784 may initiate a controlled experiment. Next, the state 786 may create an impact (e.g., the impact 722) at a known location with a known force (e.g., to the wearable user input helmet 100'''). The state 788 may recover 3-dimensional data from the strain sensor (e.g., one of the strain sensors 102a'''-102j'''). The state 790 may aggregate sensor data with sensor data from other locations. Next, the method 780 may move to the decision state 792.

If the decision state 792 determines there are more sensors, the method 780 may return to the state 788. If the decision state 792 determines there are not more sensors, the method 780 may move to the state 794. The state 794 may associate known data with detected data to form a training set. The state 796 may train the neural network using back-propagation. Next, the method 780 may move to the decision state 798.

If the decision state 798 determines to perform more training, the method 780 may return to the state 786. If the decision state 798 determines not to perform more training, the method 780 may move to the state 800. The state 800 may store mapped sensor data as the reference patterns 202b. Next, the method 780 may move to the state 802, which ends the method 780.

In some embodiments, a propagation model may be built using the neural network. The input to the neural network may be the three strains measured at each sensor location (e.g., the location of the sensors 102a'''-102j'''). The input may be the 3N vector.

Controlled experiments may be performed to develop the reference patterns 202b. For example, a known force (e.g., the impact 722) may be applied having a known direction at various known locations of the wearable user input device (e.g., the helmet 100'''). The parallel components (e.g., F_p) of the known forces and the associated known locations may constitute a training set.

The neural network may be trained using various methods based on the training sets. For example, the neural network may implement a back-propagation algorithm. In some embodiments, the neural network may be trained with a number (e.g., two layers). More layers may be added to the neural network as needed. The number of neural network layers and/or the method used to train the neural network may be varied according to the design criteria of a particular implementation.

The neural network may be considered trained when capable of reliably estimating the location and/or direction of a received force. Based on the training, a mapping function may be developed. The mapping function may map readings of the sensors 102a'''-102j''' to a surface location (e.g., on the wearable user helmet 100''') and/or a surface force. The surface force may be described having a magnitude and direction along a surface of the wearable user input helmet 100'''. The output of the neural network may be a 5-dimensional vector (e.g., a magnitude, two components representing a direction, and two components representing a location along the surface of the wearable user input helmet 100'''). In some embodiments, the two output components representing the direction along the surface of the wearable user input helmet 100''' may be normalized. The normalized direction may reduce the dimensionality of the output vector (e.g., a 4-dimensional vector).

Figure 22:
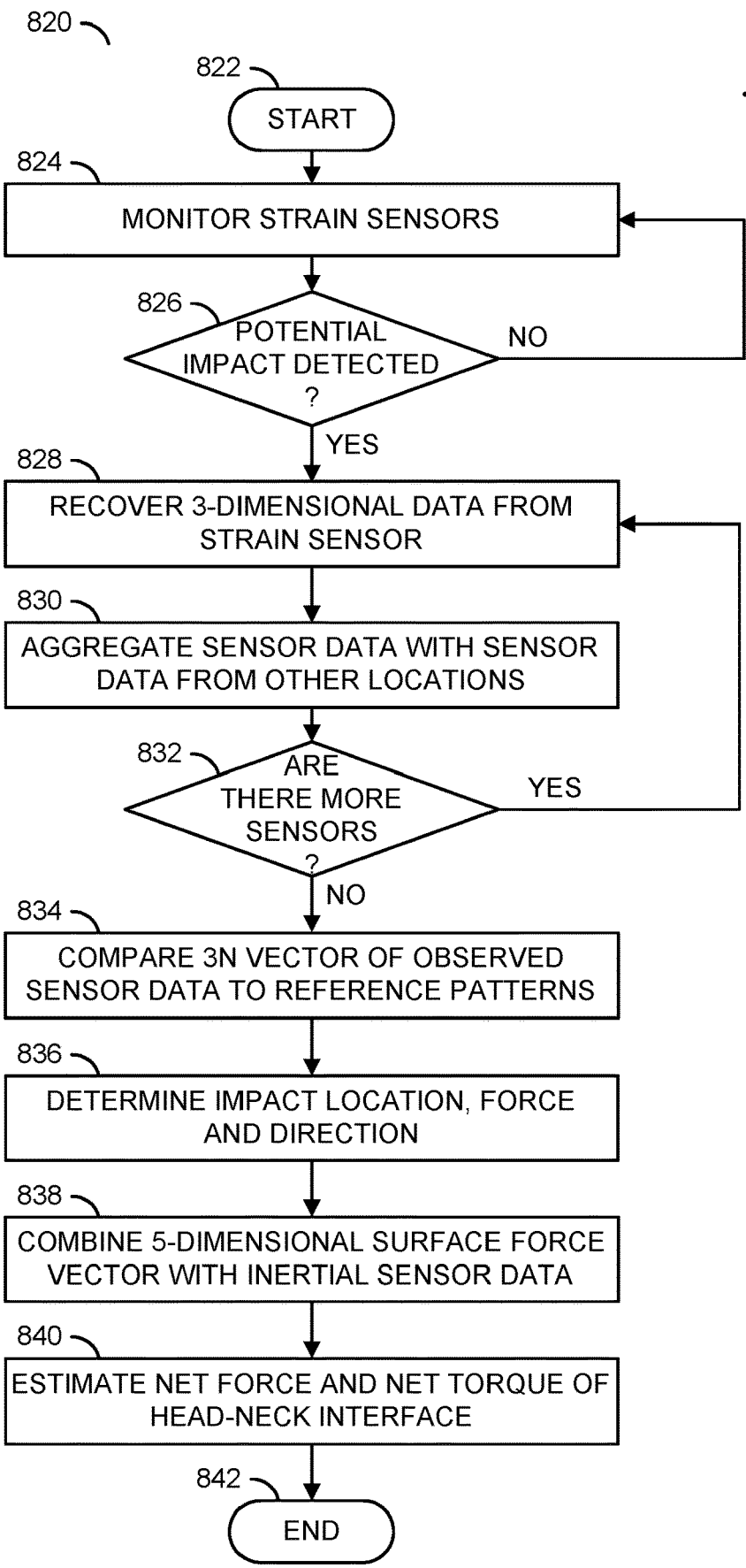
FIG. 22 is a flow diagram illustrating a method for estimating net forces from an impact.

Referring to FIG. 22, a flow diagram of a method (or process) 820 is shown. The method 820 may estimate net forces from an impact. The method 820 generally comprises a step (or state) 822, a step (or state) 824, a decision step (or state) 826, a step (or state) 828, a step (or state) 830, a decision step (or state) 832, a step (or state) 834, a step (or state) 836, a step (or state) 838, a step (or state) 840, and a step (or state) 842.

The state 822 may start the method 820. The state 824 may monitor the strain sensors (e.g., the strain sensors 102a'''-102j'''). Next, the method 820 may move to the decision state 826. If the decision state 826 determines a potential impact has not been detected, the method 820 may return to the state 824. If the decision state 826 determines a potential impact has been detected, the method 820 may move to the state 828.

The state 828 may recover the 3-dimensional data from the strain sensor (e.g., one of the strain sensors 102a'''-102j'''). The state 830 may aggregate sensor data with sensor data from other locations. Next, the method 820 may move to the decision state 832. If the decision state 832 determines there are more sensors, the method 820 may return to the state 828. If the decision state 832 determines there are not more sensors, the method 820 may move to the state 834.

The state 834 may compare the 3N vector of observed sensor data to the reference patterns 202b. The state 836 may determine an impact location, force and/or direction (e.g., using the neural network implemented on the user device 152, the remote service 154 and/or the external cloud computing resources 158). Next, the state 838 may combine the 5-dimensional surface force vector with inertial sensor data. The state 840 may estimate a net force and a net torque of the head-neck interface 742. Next, the method 820 may move to the state 842, which ends the method 820.

Data from the combination of inertial sensors and/or strain sensors 102a'''-102j''' may be used to estimate forces at the head-neck interface 742. The sum of forces and the sum of torques at the head-neck interface 742 may determine accelerations and/or rotations measured by the inertial sensors. Inverse dynamics may be used to estimate the forces at the head-neck interface 742.

The reference patterns 202b may be the impact having a known location and a known force (e.g., from the controlled experiment). Based on the reference patterns 202b, data from the sensors 102a'''-102j''' may be used to develop the mapping function. When the wearable user input helmet 100''' is used during a performance, the observed motion patterns (e.g., observed data from the sensors 102*a*'''-102*j*''') may be compared to the reference patterns 202*b* (e.g., mapped using the mapping function). The 5-dimensional vector output may be based on the comparison of the observed motion data and the reference patterns 202*b*. The 5-dimensional vector output may be an estimate of the location and/or direction of the impact 722.

Figure 23:
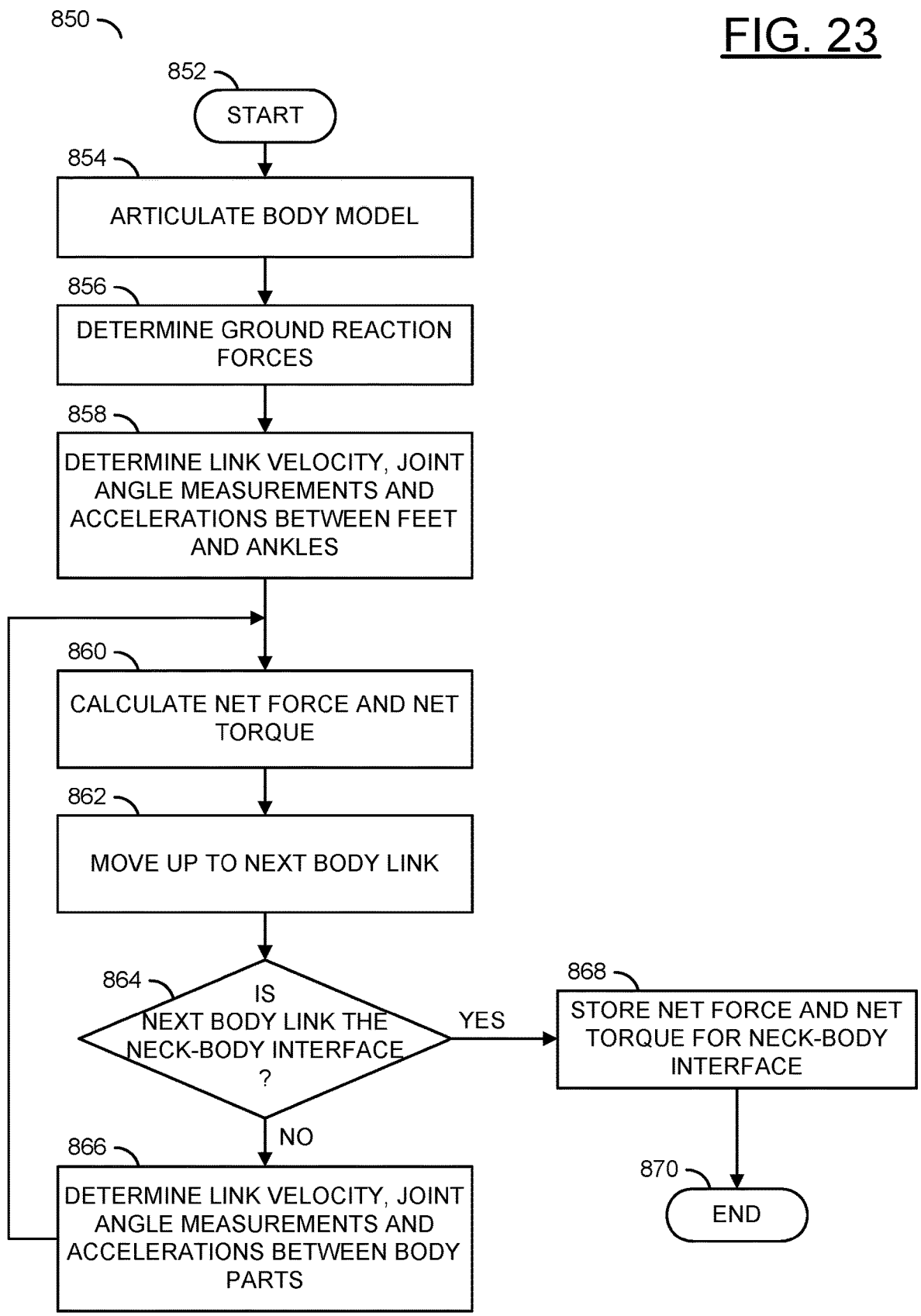
FIG. 23 is a flow diagram illustrating a method for calculating net force and net torque at a neck-body interface.

Referring to FIG. 23, a flow diagram of a method (or process) 850 is shown. The method 850 may calculate a net force and a net torque at the neck-body interface 744. The method 850 generally comprises a step (or state) 852, a step (or state) 854, a step (or state) 856, a step (or state) 858, a step (or state) 860, a step (or state) 862, a decision step (or state) 864, a step (or state) 866, a step (or state) 868, and a step (or state) 870.

The state 852 may start the method 850. The state 854 may articulate a body model of the user 70. The state 856 may determine ground reaction forces. The state 858 may determine link velocity, joint angle measurements and/or accelerations between the feet and ankles of the user 70 (e.g., using the sensors 102*a*'''''-102*c*'''''). Next, the state 860 may calculate the net force and/or the net torque (e.g., of the link). The state 862 may move up to the net body link. Next, the method 850 may move to the decision state 864.

If the decision state 864 determines the next body link is not the neck-body interface 744, the method 850 may move to the state 866. The state 866 may determine the link velocity, joint angle measurements and/or accelerations between body parts. Next, the method 850 may return to the state 860. If the decision state 864 determines the next body link is the neck-body interface 744, the method 850 may move to the state 868. The state 868 may store the net force and net torque for the neck-body interface 744 (e.g., in the memory 112). Next, the method 850 may move to the state 870, which ends the method 850.

Using an articulated model of the human body, forces may be estimated at various links (e.g., joints) of the user 70. The forces may be estimated at a particular link given accelerations and/or known forces. The forces may be estimated iteratively throughout the various links of the body. For example, the ground reaction forces may be measured using the soccer cleats 100*a*'''''-100*b*'''''. Based on the ground forces and data from the other wearable user input devices, the forces may be calculated throughout the body of the user 70 to determine a risk of neck injury.

A particular body part of the user (e.g., the user 70''''') may be isolated and a free-body diagram may be modeled. Data from the sensors (e.g., 102*a*'''''-102*c*''''') may provide data measurements of linear and/or angular accelerations. Using the linear and/or acceleration data the net force and/or net torque applied to the body part may be estimated. The net force may be a result of many biomechanical forces, which may be difficult to disentangle exactly. Generally, the estimated net force and/or net torque may provide sufficient information.

The articulated model may be used to estimate forces at the neck-body interface 744. A complex articulated model may provide detailed information. Generally, the articulated model may not be complex. For example, the articulated model may be designed with enough complexity to provide estimated neck-body forces. The articulated model may be configured to be specific to a particular sport and/or body type (e.g., weight, limb length, stature, etc.). The type of articulated model may be varied according to the design criteria of a particular implementation.

Figure 24:
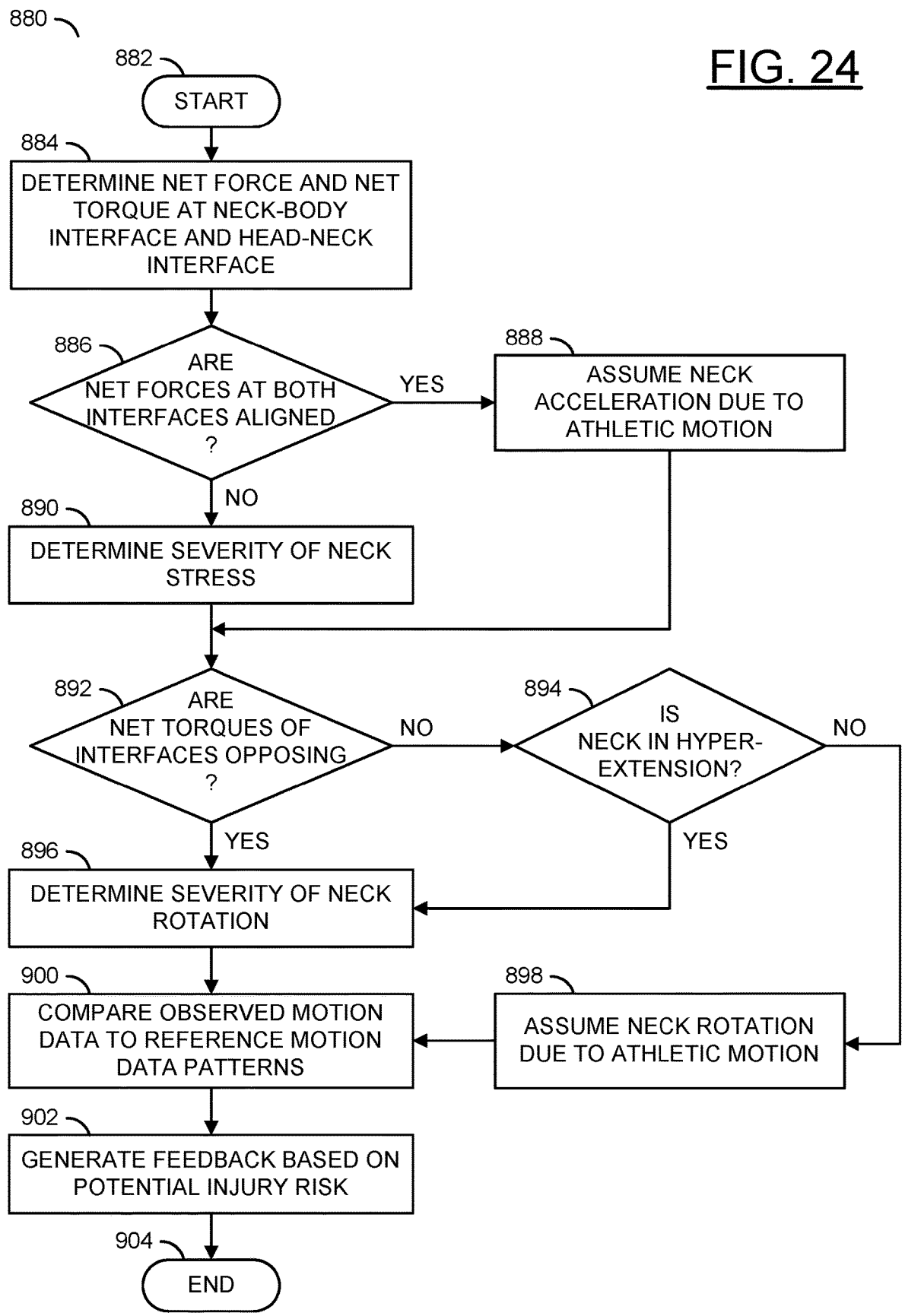
FIG. 24 is a flow diagram illustrating a method for measuring a potential risk of injury.

Referring to FIG. 24, a flow diagram of a method (or process) 880 is shown. The method 880 may measure a potential risk of injury. The method 880 generally comprises a step (or state) 882, a step (or state) 884, a decision step (or state) 886, a step (or state) 888, a step (or state) 890, a decision step (or state) 892, a decision step (or state) 894, a step (or state) 896, a step (or state) 898, a step (or state) 900, a step (or state) 902, and a step (or state) 904.

The state 882 may start the method 880. The state 884 may determine the net force and/or the net torque at the neck-body interface 744 and the head-neck interface 742. For example, the net force and/or net torque of the head-neck interface 742 may be determined using the method 820 (e.g., described in association with FIG. 22). In another example, the net force and/or net torque of the neck-body interface 744 may be determined using the method 850 (e.g., described in association with FIG. 23). Next, the method 880 may move to the decision state 886.

If the decision state 886 determines the net forces at both interfaces are aligned, the method 880 may move to the state 888. The state 888 may assume the neck acceleration is due to an athletic motion. Next, the method 880 may move to the decision state 892. If the decision state 886 determines the net forces at both interfaces are not aligned, the method 880 may move to the state 890. The state 890 may determine a severity of the neck stress. Next, the method 880 may move to the decision state 892.

If the decision state 892 determines the net torques of the interfaces are not opposing, the method 880 may move to the decision state 894. If the decision state 892 determines the net torques of the interfaces are opposing, the method 880 may move to the state 896. The state 896 may determine the severity of neck rotation. Next, the method 880 may move to the state 900.

If the decision state 894 determines the neck is in hyper-extension, the method 880 may move to the state 896. If the decision state 894 determines the neck is not in hyper-extension, the method 880 may move to the state 898. The state 898 may assume the neck rotation is due to an athletic motion. Next, the method 880 may move to the state 900. The state 900 may compare the observed motion data to the reference motion data patterns 202*b*. The state 902 may generate feedback based on a potential injury risk. Next, the method 880 may move to the state 904, which ends the method 880.

A net force (e.g., fh) and a net torque (e.g., th) may be determined for the head-neck interface 742. A net force fb and a net torque tb may be determined for the neck-body interface 744. For example, the net force fh and the net torque th may be determined using the strain gages in the wearable user input helmet 100''' (e.g., as described in association with FIG. 22). In another example, the net force fh and the net torque th may be determined using the flexible angular displacement sensors 102*a*'''''-102*c*'''''. The techniques and/or sensors used to estimate the net forces and/or net torques may be varied according to the design criteria of a particular implementation.

Large values of fh and fb may not necessarily imply that there is risk of neck injury. For example, both forces aligned in the same direction may indicate the neck is accelerating due to running, jumping and/or another athletic motion. In another example, the forces that are large and of equal magnitude but in opposite direction may indicate the neck is under severe stress. Opposing values of th and tb may indicate when the neck is about to go into hyper-extension or hyper-flexion. Even non-opposing torques may cause neck injury.

The severity of stress to the neck and/or rotation of the neck may be determined using context information. For example, medical research may determine may provide new insights into causes of neck trauma. The context information may be updated as new information becomes available. For example, a threshold may be used to trigger feedback generation (e.g., of a risk of injury). The threshold may change as new information becomes available. The threshold of stress and/or rotation causing neck injury may be varied according to the design criteria of a particular implementation.

In some embodiments, the head-neck interface 742 and the neck-body interface 744 may be assumed to be parallel to the ground and aligned. The assumption may create a model where the torques while standing perfectly upright are zero. In other embodiments, the neck-body interface 744 may be assumed to be parallel to the ground, but not the head-neck interface 742 (e.g., the torques at rest will not be zero). The assumptions used may be varied according to the design criteria of a particular implementation.

Figure 25:
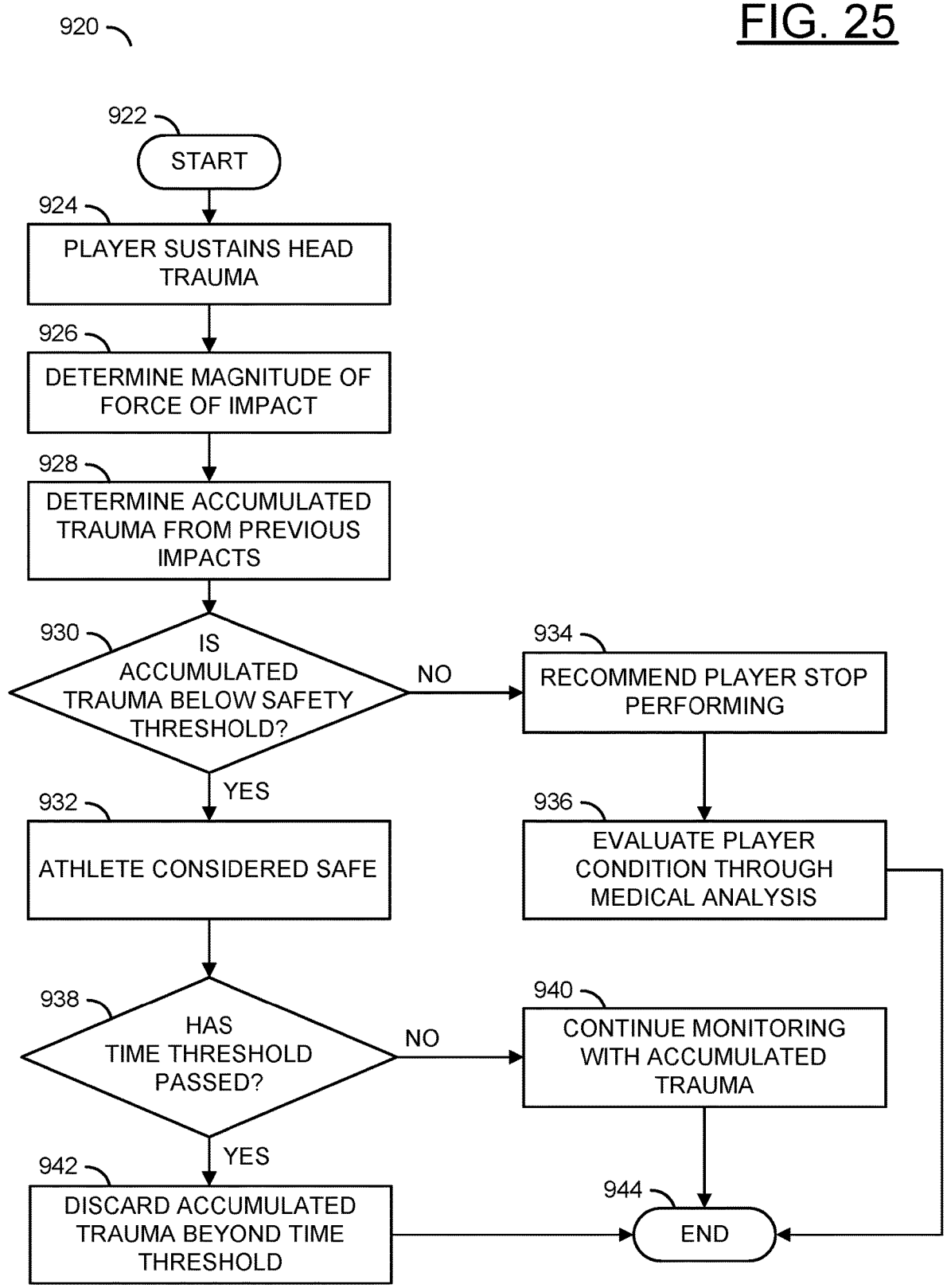
FIG. 25 is a flow diagram illustrating a method for measuring cumulative micro-traumas.

Referring to FIG. 25, a flow diagram of a method (or process) 920 is shown. The method 920 may measure cumulative micro-traumas. The method 920 generally comprises a step (or state) 922, a step (or state) 924, a step (or state) 926, a step (or state) 928, a decision step (or state) 930, a step (or state) 932, a step (or state) 934, a step (or state) 936, a decision step (or state) 938, a step (or state) 940, a step (or state) 942, and a step (or state) 944.

The state 922 may start the method 920. In the state 924, the player (e.g., the user 70) may sustain a head trauma. The state 926 may determine a magnitude of a force of an impact (e.g., the impact 722). The state 928 may determine accumulated trauma from previous impacts. Next, the method 920 may move to the decision state 930.

If the decision state 930 determines the accumulated trauma is below a safety threshold, the method 920 may move to the state 932. In the state 932, the athlete may be considered safe. Next, the method 920 may move to the decision state 938. If the decision state 930 determines the accumulated trauma is not below a safety threshold, the method 920 may move to the state 934. The state 934 may recommend the player stop performing (e.g., provide a notification to the user device 152, generate haptic feedback using the wearable user input device 100, etc.). The state 936 may evaluate a condition of the player through medical analysis. Next, the method 920 may move to the state 944, which ends the method 920.

If the decision state 938 determines a time threshold has not passed, the method 920 may move to the state 940. The state 940 may continue monitoring with the accumulated trauma data. Next, the method 920 may move to the state 944, which ends the method 920. If the decision state 938 determines the time threshold has not passed, the method 920 may discard accumulated trauma data from beyond the time threshold. Next, the method 920 may move to the state 944, which ends the method 920.

The wearable user input device 100 may be configured to track an accumulation of impact information (e.g., the estimated impact). For example, the estimated impact may be a micro-trauma. Micro-traumas may be an impact sustained/received by the user 70. Micro-traumas may not cause significant injury in isolation and/or immediately detectable symptoms to the user 70.

A cumulative effect of head micro-traumas may be an important factor in a long-term deterioration of cognitive functions. For example, one micro-trauma to the head of the user 70 may not be enough for the user 70 to be considered unsafe (e.g., the user 70 is below the safety threshold). In another example, an accumulation of two or more micro-traumas to the head of the user 70 may be enough for the user 70 to be considered unsafe (e.g., the user 70 is above the safety threshold). The amount of force and/or rotation for an impact to be considered a micro-trauma may be varied according to the design criteria of a particular implementation.

In some embodiments, a blow to the head (e.g., the impact 722) may have a probability of doing damage. For example, the probability of damage may be defined by an equation:

$$p\{\text{injury}\}=1-e^{-ks} \quad \text{(EQ1)}$$

A value (e.g., k) may be a constant value where k>0. A value (e.g., s) may be a magnitude of the rotational force of the blow. In some embodiments, a similar analysis may be performed to determine a non-rotational force of the blow. According to the equation EQ1, a probability of damage is zero if the magnitude of the force s is zero. According to the equation EQ1, the probability of damage approaches 1 if the magnitude of the force s becomes large.

The user 70 may suffer a sequence of traumas (e.g., micro-traumas) over a period of time (e.g., s1, s2, . . . , sn). Each of the traumas may have an associated probability of causing an injury. A probability for injury due to the sequence of traumas may be determined by an equation:

$$P=1-(1-p1)(1-p2)\ldots(1-pn)=1-e^{-k(s1+s2+\ldots+sn)} \quad \text{(EQ2)}$$

A value (e.g., c) may be a risk threshold. For example, if p>c then the user 70 may be considered unsafe (e.g., should be benched, should stop performing, should seek medical attention, etc.). The value c may be varied according to the design criteria of a particular implementation. The user 70 may be considered safe if the accumulated trauma complies with a bound based on an equation:

$$(s1+s2+\ldots+sn)<-(1/k)\log(1-c) \quad \text{(EQ3)}$$

The user 70 may be considered safe when compliant with the equation EQ3 (e.g., the safety threshold). In some embodiments the user 70 may be considered compliant with the equation EQ3 if the user 70 is within the safety threshold for a rolling window of time (e.g., a time threshold of 30 days). The user device 152, the remote service 154 and/or the cloud databases 160 may track the accumulated micro-traumas of the user 70. The amount of time to store tracked information (e.g the time threshold) about micro-traumas and/or the safety threshold may be varied according to the design criteria of a particular implementation.

For example, estimated data from accumulated micro-traumas older than 30 days may be discarded as new daily measurements are entered. In other embodiments, a sum of micro-traumas (e.g., s1+s2+s3 . . . +sn) in the equation EQ3 may be replaced by a time integral over a signal s(t). The signal s(t) may measures a magnitude of force over time.

A probabilistic model (e.g., as described by the equations EQ1, EQ2 and/or EQ3) may be one method/model of determining accumulated data from estimated impacts. The method/model of determining accumulated data from estimated impacts may be refined and/or replaced based on data from the medical field (e.g., context data). For example, the method/model may be refined/replaced as the medical field gains more understanding about the effect of micro-traumas and/or head impacts.

The user 70 may be considered safe if the user 70 is within the safety threshold. For example, if the user 70 is considered safe, feedback may be generated (e.g., using the wearable user input devices 100) to indicate the user 70 may continue performing. If the user 70 is not within the safety threshold, feedback may be generated recommending the user 70 stop performing. For example, if the user 70 is not within the safety threshold a notification may be sent to a user device of a coach and/or trainer (e.g., the user device 152) to bench the user 70. In another example, if the user 70 is not within the safety threshold a notification may be sent recommending the user 70 seek medical attention. For example, the wearable user input devices 100 and/or the user device 152 may determine a potential risk of injury to the user 70 and the user 70 should seek further medical analysis from a trained professional.

Figure 26:
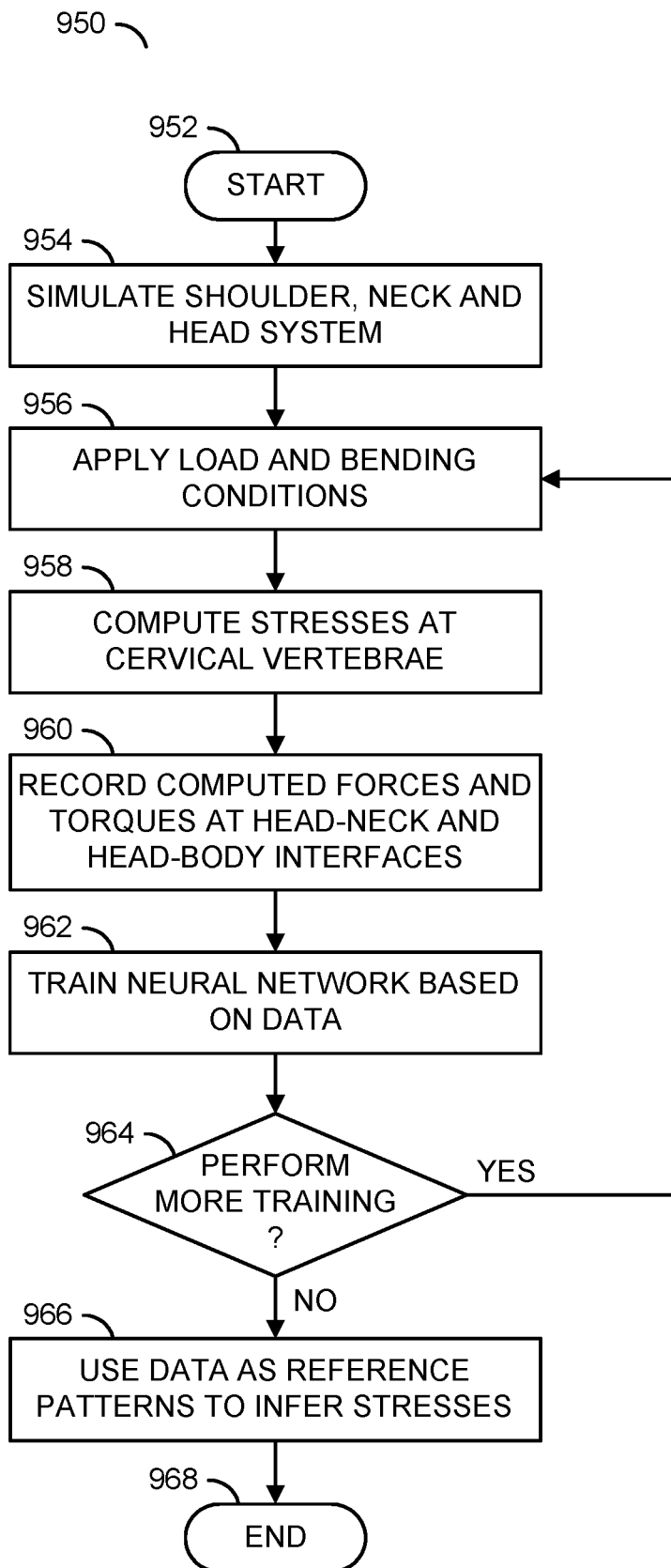
FIG. 26 is a flow diagram illustrating a method for training a neural network to develop reference patterns for detecting neck injuries.

Referring to FIG. 26, a flow diagram of a method (or process) 950 is shown. The method 950 may train the neural network to develop reference patterns for detecting neck injuries. The method 950 generally comprises a step (or state) 952, a step (or state) 954, a step (or state) 956, a step (or state) 958, a step (or state) 960, a step (or state) 962, a decision step (or state) 964, a step (or state) 966, and a step (or state) 968.

The state 952 may start the method 950. The state 954 may simulate a shoulder, neck and head system. Next, the state 956 may apply load and/or bending conditions. The state 958 may compute stresses at a cervical vertebrae. Next, the method 960 may record computed forces and/or torques at the head-neck interface 742 and the neck-body interface 744.

The state 962 may train the neural network based on the data (e.g., the recorded forces/torques). Next, the method 950 may move to the decision state 964. If the decision state 964 determines to perform more training, the method 950 may return to the state 956. If the decision state 964 determines not to perform more training, the method 950 may move to the state 966. The state 966 may use the data as the reference patterns 202b to infer stresses (e.g., neck strain of the user 70). Next, the method 950 may move to the state 968, which ends the method 950.

A mechanical model may be developed to determine a risk metric for neck injury. The mechanical model may be configured to estimate impact to determine a neck strain of the user 70. For example, a mechanical model of the neck of the user 70 may be developed using controlled experiments. In some embodiments, the mechanical model may determine forces and/or motions at each (e.g., 7) cervical vertebrae of the user 70. For example, finite element analysis may be implemented to determine the biomechanics of the neck of the user 70.

Based on the mechanical model used to determine the risk metric for neck injury, the reference patterns 202b may be developed. The neural network may be trained based on the mechanical model. For example, the neural network may be trained to determine the reference patterns 202b.

The neural network may be trained by simulating a shoulder-neck-head system of the user 70 under different loading conditions and/or bending motions. Stresses at the cervical vertebrae may be computed for each of the loading conditions and/or bending motions (e.g., using controlled experiments) by determining forces and/or torques. The computed forces and/or torques may be stored (e.g., by the user device 152, the remote services 154 and/or the cloud databases 160). The stored forces and/or torques may be the forces and/or torques at the head-neck interface 742 and/or the neck-body interface 744.

Data from the head-neck interface 742 and/or the neck-body interface 744 may be used to train the neural network. The neural network may compute an inverse problem. The computation of the inverse problem may infer the stresses at the cervical vertebrae given the forces and/or torques at the head-neck interface 742 and the head-body interface 744.

The inference of the stresses at the cervical vertebrae using the forces and/or torques at the head-neck interface 742 and the neck-body interface 744 may be stored as the reference patterns 202b. For example, the mapping of the forces and/or torques of the head-neck interface 742 and the head-body interface 744 to the stresses of the cervical vertebrae may be represented by the reference patterns 202b.

The wearable user input devices 100 may be configured to generate a signal representing risk. The signal may be generated to indicate the cervical vertebrae most at risk. In some embodiments, the signal and/or a separate feedback signal may be generated based on hyperextension and/or hyperflexion of the entire neck of the user 70. The type of feedback generated may be varied according to the design criteria of a particular implementation.

In some embodiments the trained neural network may estimate the stresses at the cervical vertebrae. Other methods and/or models may be used to map the stresses of the cervical vertebrae to the reference patterns 202b. The methods and/or models used may be varied according to the design criteria of a particular implementation.

Figure 27:
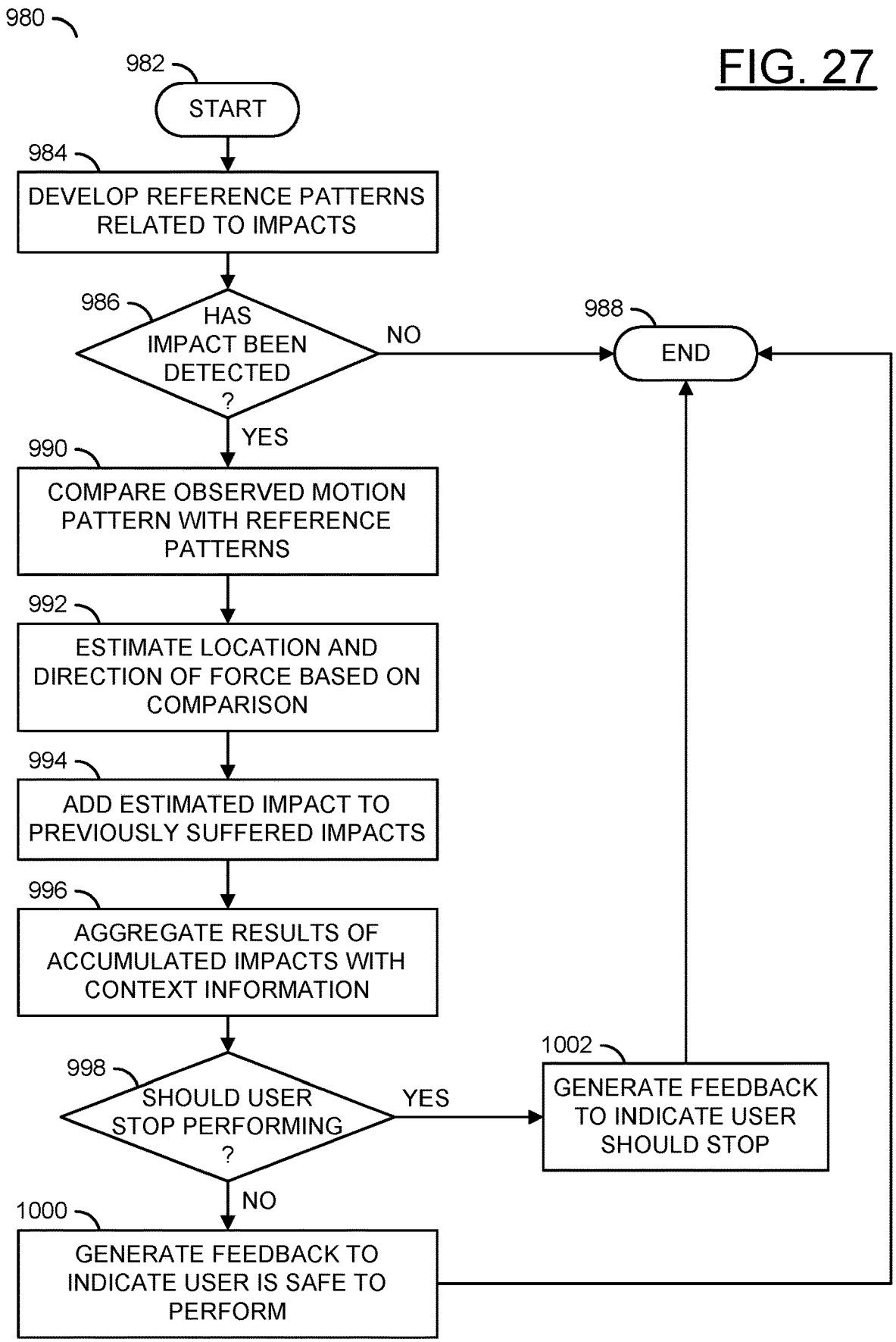
FIG. 27 is a flow diagram illustrating a method for generating feedback based on impacts and context information.

Referring to FIG. 27, a flow diagram of a method (or process) 980 is shown. The method 980 may generate feedback based on impacts and context information. The method 980 generally comprises a step (or state) 982, a step (or state) 984, a decision step (or state) 986, a step (or state) 988, a step (or state) 990, a step (or state) 992, a step (or state) 994, a step (or state) 996, a decision step (or state) 998, a step (or state) 1000, and a step (or state) 1002.

The state 982 may start the method 980. The state 984 may develop the reference patterns 202b related to impacts. Next, the method 980 may move to the decision state 986. If the decision state 986 determines an impact has not been detected, the method 980 may move to the state 988, which ends the method 980. If the decision state 986 determines an impact has been detected, the method 980 may move to the state 990.

The state 990 may compare the observed motion pattern with the reference patterns 202b. The state 992 may estimate a location and/or direction of force based on the comparison. Next, the state 994 may add the estimated impact to previously suffered impacts. The state 996 may aggregate results of the accumulated impact data with context information. Next, the method 980 may move to the decision state 998.

If the decision state 998 determines the user 70 should not stop performing, the method 980 may move to the state 1000. In the state 1000, feedback may be generated (e.g., by the wearable user input device 100, the user device 152, etc.) to indicate the user 70 is safe to perform. Next, the method 980 may move to the state 988, which ends the method 980. If the decision state 998 determines the user 70 should stop performing, the method 980 may move to the state 1002. In the state 1002, feedback may be generated (e.g., by the wearable user input device 100, the user device 152, etc.) to indicate the user 70 should stop performing. Next, the method 980 may move to the state 988, which ends the method 980.

Impact data (e.g., forces and/or torques) alone potentially may not provide sufficient data to determine head injury and/or whether the user 70 may be safe or unsafe. For example, spinal and/or neck injuries may be dependent on posture. In another example, recent injury history may contribute to head injuries (e.g., the accumulated impact data). In still another example, a head injury may be caused by a single, large impact.

Previously suffered impacts may be an injury history of the user 70. The wearable user input devices (e.g., the helmet 100'''), the user device 152, the remote service 154, and/or the cloud databases 160 may store data from the previously suffered impacts as previously suffered impact data. Previously suffered injury history may be a cumulative effect of concussive forces and/or a pattern of injuries over time. An accumulation of blows may cause damage. In some examples, the blows and/or the accumulation of blows may be above the safety threshold.

In some embodiments, an aggregate history of previously suffered impacts may be a simple sum and/or average (e.g., an expected-case analysis). In other embodiments, previously suffered impacts may be aggregated based on min-max and/or other worst-case analysis methods. For example, some injuries may be due to repetition (e.g., an expected-case analysis provides useful information) and other injuries may be due to a small number of bad/dangerous motions/impacts (e.g., a worst-case analysis provides useful information). Feedback may be generated based on analysis of the aggregate history of previously suffered impacts to indicate the user 70 should be benched (e.g., removed from play and/or stop performing). For example, the user 70 may be removed from play unless cleared by a medical professional (e.g., a physical therapist). The type of analysis used to determine injury may be varied according to the design criteria of a particular implementation.

Context information may be used to determine whether the user 70 is safe and/or unsafe to perform. Feedback may be generated based on the estimated impact, previously suffered impact data, and/or context information. Context information may provide further information about the health of the user 70.

Context information may comprise cognitive data sources. Cognitive data sources may be used to determine mental symptoms of the head injury (e.g., symptoms not easily determined/visible based on a physical examination). For example, the user 70 may appear physically healthy, but the head injury may cause lingering mental symptoms (e.g., headaches, memory loss, a so-called "mental fog" often associated with concussions, etc.). Context information may be used to ensure the user 70 is symptom free before returning to action.

Context information may comprise baseline cognitive testing (e.g., tests performed when healthy compared to tests performed after sustaining an injury), school grades (e.g., a decrease in grades may indicate a head injury and/or memory loss), proximity data, attention data, data from learning management systems, geographical information (e.g., distance from appropriate medical/neurological facilities may indicate greater caution should be observed in dealing with a potential injury), health records, data from social media sources, measurements of attention, changes in behavior, and/or measurements of attitude. Context information may comprise research (e.g., medical research) and may be updated/refined as new information becomes available. The type of contextual information may be refined over time. For example, continuing medical research may determine other types of relevant information to determine head injuries and/or length of recovery. The type of context information may be varied according to the design criteria of a particular implementation.

Context information may allow the user 70 to receive personalized head injury monitoring and/or management. For example, each user may have different recovery times and/or present with different symptoms. Based on data from the accumulated impact data, the estimated impact and/or the context information a medical professional may determine treatment options. In some embodiments, the medical professional may use data from the wearable user input devices (e.g., using data stored in the cloud databases 160) to make a remote diagnosis.

In some embodiments, context information may be data from other users. For example, other users wearing the wearable user input devices (e.g., the wearable user input helmet 100''') may have suffered injuries. Data from various users with various body types, prior medical history and/or various types of received blows may be aggregated. Patterns may be determined based on the aggregated information from other users. The patterns may be used to update treatment options, improve/refine a diagnosis, estimate recovery time, etc.

The determination of the safety of the user 70 may be based on the accumulated force over time and/or the context information. The amount of accumulated force over time and/or the context information may be compared to thresholds. The thresholds may decay over time and/or determine healing curves. For example, a number of accumulated blows to the user 70 and/or the force of the blows may be used to estimate a healing curve (e.g., a recovery time). The healing curve may provide an indication of when the user 70 may be likely to resume performing.

In some embodiments, the recovery time may be proportional to accumulated impact (e.g., each impact increases the estimated recovery time by a fixed amount). In other embodiments, a monotonically increasing function of accumulated impacts may determine the recovery time (e.g., each impact increases the estimated recovery time by increasing amounts). For example, estimated recovery time may be increased more heavily as the accumulated damage increases according to the equation:

$$f(x)=a \cdot e^{cx} \qquad (EQ4)$$

Values (e.g., a and c) may be positive constant values. A value (e.g., x) may be an accumulated impact value.

In some embodiments, estimated recovery time may be based on the accumulated impact data and the context information. For example, the context information may be similar injuries suffered by others. In another example, the injury history and/or previous recovery time of past injuries of the user 70 may be considered (e.g., to avoid repeating a previous concussion episode). Using the previously suffered impact data may provide personal head injury monitoring and/or management. The type of context information used to determine the estimated recovery time may be varied according to the design criteria of a particular implementation.

The wearable user input device 100 may be used to generate feedback based on the aggregated results (e.g., the force/torques of an impact, the accumulated impact data, the aggregated physical impact data, the context data, the determined recovery time, whether a performer should stop performing, etc.) of users playing sports. For example, the wearable input device may be the wearable input helmet 100'''. In some embodiments, the wearable user input device may be worn by military personnel (e.g., a military helmet, a combat helmet, etc.). In other embodiments, the wearable user input device may be worn by construction workers (e.g., a hard hat). The wearable user input devices may be used in any field/application where injuries and/or injury monitoring may occur (e.g., sports, military, work, rehabilitation centers, etc.). The type of application may be varied according to the design criteria of a particular implementation.

The functions performed by the diagrams of FIGS. 9-15 and 21-27 may be implemented using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU), video digital signal processor (VDSP) and/or similar computational machines, programmed according to the teachings of the specification, as will be apparent to those skilled in the relevant art(s). Appropriate software, firmware, coding, routines, instructions, opcodes, microcode, and/or program modules may readily be prepared by skilled programmers based on the teachings of the disclosure, as will also be apparent to those skilled in the relevant art(s). The software is generally executed from a medium or several media by one or more of the processors of the machine implementation.

The invention may also be implemented by the preparation of ASICs (application specific integrated circuits), Platform ASICs, FPGAs (field programmable gate arrays), PLDs (programmable logic devices), CPLDs (complex programmable logic devices), sea-of-gates, RFICs (radio frequency integrated circuits), ASSPs (application specific standard products), one or more monolithic integrated circuits, one or more chips or die arranged as flip-chip modules and/or multi-chip modules or by interconnecting an appropriate network of conventional component circuits, as is described herein, modifications of which will be readily apparent to those skilled in the art(s).

The invention thus may also include a computer product which may be a storage medium or media and/or a transmission medium or media including instructions which may be used to program a machine to perform one or more processes or methods in accordance with the invention. Execution of instructions contained in the computer product by the machine, along with operations of surrounding circuitry, may transform input data into one or more files on the storage medium and/or one or more output signals representative of a physical object or substance, such as an audio and/or visual depiction. The storage medium may include, but is not limited to, any type of disk including floppy disk, hard drive, magnetic disk, optical disk, CD-ROM, DVD and magneto-optical disks and circuits such as ROMs (read-only memories), RAMs (random access memories), EPROMs (erasable programmable ROMs), EEPROMs (electrically erasable programmable ROMs), UVPROM (ultra-violet erasable programmable ROMs), Flash memory, magnetic cards, optical cards, and/or any type of media suitable for storing electronic instructions.

The elements of the invention may form part or all of one or more devices, units, components, systems, machines and/or apparatuses. The devices may include, but are not limited to, servers, workstations, storage array controllers, storage systems, personal computers, laptop computers, notebook computers, palm computers, personal digital assistants, portable electronic devices, battery powered devices, set-top boxes, encoders, decoders, transcoders, compressors, decompressors, pre-processors, post-processors, transmitters, receivers, transceivers, cipher circuits, cellular telephones, digital cameras, positioning and/or navigation systems, medical equipment, heads-up displays, wireless devices, audio recording, audio storage and/or audio playback devices, video recording, video storage and/or video playback devices, game platforms, peripherals and/or multi-chip modules. Those skilled in the relevant art(s) would understand that the elements of the invention may be implemented in other types of devices to meet the criteria of a particular application.

While the invention has been particularly shown and described with reference to the preferred embodiments thereof, it will be understood by those skilled in the art that various changes in form and details may be made without departing from the scope of the invention.

The invention claimed is:

1. A method for monitoring user safety in a vehicle, comprising the steps of:
   (A) detecting motion patterns of a respective user using a plurality of wearable user input devices;
   (B) monitoring a user status using said plurality of wearable user input devices;
   (C) monitoring vehicle information using a plurality of vehicle sensors;
   (D) communicating said motion patterns, said user status and said vehicle information to a user device using a wireless transceiver;
   (E) developing and storing a vocabulary of reference patterns based on said motion patterns, said user status and said vehicle information;
   (F) correlating said motion patterns, said user status and said vehicle information with said reference patterns in said vocabulary;
   (G) normalizing said motion patterns, said user status and said vehicle information to approximate an event template;
   (H) comparing said normalized motion patterns, said user status and said vehicle information with said correlated reference patterns; and
   (I) generating feedback for said user based on said comparison, wherein steps (E)-(I) are performed by said user device.

2. The method according to claim 1, wherein said vehicle information comprises impact detection.

3. The method according to claim 1, wherein said vehicle information comprises traffic pattern data.

4. The method according to claim 1, wherein said vehicle sensors are configured to communicate with emergency services.

5. The method according to claim 1, wherein said user status comprises health, attitude and behavior of said user.

6. The method according to claim 5, wherein said health, attitude and behavior are used to determine a drowsiness level of said user.

7. The method according to claim 1, wherein said feedback indicates said user should take a break.

8. The method according to claim 1, wherein said feedback indicates said user is in an unsuitable condition to perform a task.

9. The method according to claim 1, wherein said feedback indicates an alternate travel path.

10. The method according to claim 1, wherein said feedback is used to determine vehicle design improvement.

11. The method according to claim 1, wherein said feedback is used to determine transportation signage.

12. The method according to claim 1, wherein said event template approximates a traffic scenario.

13. A system for monitoring user training for a sport comprising:
   a plurality of wearable user input devices each configured (i) to detect motion patterns of a user and (ii) monitor a user status;
   an equipment sensor configured to monitor equipment motion of sports equipment; and
   a wireless transceiver configured to communicate said motion patterns, said user status and said equipment motion to a user device, wherein said user device is configured to (i) develop and store a vocabulary of reference patterns based on said motion patterns, said user status and said equipment motion, (ii) correlate said motion patterns, said user status and said equipment motion with said reference patterns in said vocabulary, (iii) normalize said motion patterns, said user status and said equipment motion to approximate an event template, (iv) compare said normalized motion patterns, said user status and said equipment motion with said correlated reference patterns and (v) generate feedback for said user based on said comparison.

14. The system according to claim 13, wherein (i) said sports equipment comprises a golf club, (ii) said equipment motion comprises a golf swing and (iii) said reference patterns in said vocabulary comprise a training swing for said golf club.

15. The system according to claim 14, wherein said feedback is configured to prevent injuries when playing said sport.

16. The system according to claim 13, wherein said reference patterns are generated by monitoring said motion patterns, said user status and said equipment motion of a trainer.

* * * * *